United States Patent
Cheng et al.

(10) Patent No.: US 12,234,314 B2
(45) Date of Patent: Feb. 25, 2025

(54) ZWITTERIONIC POLYMERS FOR BIOMEDICAL APPLICATIONS

(71) Applicant: THE BOARD OF TRUSTEES OF THE UNIVERSITY OF ILLINOIS, Urbana, IL (US)

(72) Inventors: Gang Cheng, Chicago, IL (US); Huifeng Wang, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 928 days.

(21) Appl. No.: 17/047,716

(22) PCT Filed: Apr. 19, 2019

(86) PCT No.: PCT/US2019/028296
§ 371 (c)(1),
(2) Date: Oct. 15, 2020

(87) PCT Pub. No.: WO2019/204712
PCT Pub. Date: Oct. 24, 2019

(65) Prior Publication Data
US 2021/0163657 A1    Jun. 3, 2021

Related U.S. Application Data

(60) Provisional application No. 62/659,939, filed on Apr. 19, 2018.

(51) Int. Cl.
| | | |
|---|---|---|
| *C08G 18/10* | (2006.01) | |
| *A61L 27/18* | (2006.01) | |
| *A61L 29/06* | (2006.01) | |
| *A61L 31/06* | (2006.01) | |
| *C08G 18/08* | (2006.01) | |
| *C08G 18/32* | (2006.01) | |
| *C08G 18/38* | (2006.01) | |
| *C08G 18/48* | (2006.01) | |
| *C08G 18/73* | (2006.01) | |

(52) U.S. Cl.
CPC .......... *C08G 18/0833* (2013.01); *A61L 27/18* (2013.01); *A61L 29/06* (2013.01); *A61L 31/06* (2013.01); *C08G 18/10* (2013.01); *C08G 18/3206* (2013.01); *C08G 18/3275* (2013.01); *C08G 18/3821* (2013.01); *C08G 18/4833* (2013.01); *C08G 18/73* (2013.01); *C08G 2210/00* (2013.01)

(58) Field of Classification Search
CPC . C08G 18/3275; C08G 18/0833; C08G 18/10
See application file for complete search history.

(56) References Cited

U.S. PATENT DOCUMENTS

| | | | | |
|---|---|---|---|---|
| 4,992,507 A * | 2/1991 | Coogan .............. | C08G 18/0866 | 524/839 |
| 5,225,513 A * | 7/1993 | Scholz .................. | C08G 18/10 | 528/53 |
| 8,404,224 B2 | 3/2013 | Jiang et al. | | |
| 8,658,192 B2 | 2/2014 | Jiang et al. | | |
| 9,695,275 B2 | 7/2017 | Cheng | | |
| 9,878,049 B2 | 1/2018 | Cheng et al. | | |
| 10,058,620 B2 | 8/2018 | Cheng et al. | | |
| 2004/0254325 A1 | 12/2004 | Kuepfer et al. | | |
| 2005/0112203 A1 * | 5/2005 | Shau ...................... | C12N 15/87 | 526/303.1 |
| 2008/0160318 A1 * | 7/2008 | Senkfor ............... | C08G 18/765 | 428/423.1 |
| 2008/0227945 A1 * | 9/2008 | Richards .............. | C08G 18/672 | 528/75 |
| 2009/0278084 A1 * | 11/2009 | Messana ............... | C07C 229/60 | 252/182.28 |
| 2011/0177020 A1 * | 7/2011 | Mahmoud ................ | C09D 5/14 | 424/78.23 |
| 2014/0024768 A1 | 1/2014 | Coneski et al. | | |
| 2015/0299948 A1 * | 10/2015 | Pan .......................... | D06P 5/30 | 524/591 |
| 2016/0083610 A1 | 3/2016 | Lin et al. | | |
| 2016/0251470 A1 | 9/2016 | Cheng et al. | | |
| 2017/0362458 A1 | 12/2017 | Cheng et al. | | |

FOREIGN PATENT DOCUMENTS

| | | | | |
|---|---|---|---|---|
| CN | 104403086 B | | 5/2017 | |
| CN | 106631845 A | * | 5/2017 | ........... C07C 227/08 |
| JP | 5821097 B2 | | 11/2015 | |
| WO | WO-2017/003639 A2 | | 1/2017 | |
| WO | WO-2017/058871 A1 | | 4/2017 | |
| WO | WO-2019/204712 A1 | | 10/2019 | |
| WO | WO-2019/236858 A1 | | 12/2019 | |

OTHER PUBLICATIONS

CN-106631845-A_May 2017_English.*
CN-106631845_Zhang et al._May 2017_p. 1-14.*
Akindoyo et al., PU review Polyurethane types. synthesis and applications, RSC adv 6(2016) 114453-114482.
Alperin et al., Polyurethane films seeded with embryonic stem cell-derived cardiomyocytes for use in cardiac tissue engineering applications, Biomaterials, 26(35):7377-86 (2005).
Anderson et al., Foreign body reaction to biomaterials, Semin. Immunol. 20 (2008) 86-100.
Berta et al., Effect of chemical structure on combustion and thermal behaviour of polyurethane elastomer layered silicate nanocomposites, Polypi. Degrad. Stab. 91 (2006) 1179-1191.
Cao et al., Switchable Antimicrobial and Antifouling Hydrogels with Enhanced Mechanical Properties, Adv Health Mater 2 (2013) 1096-1102.
Cao et al., The impact of structure on elasticity, switchability, stability and functionality of an all-in-one carboxybetaine elastomer, Biomaterials 34 (2013), 7592-7600.

(Continued)

Primary Examiner — Michael L Leonard
(74) Attorney, Agent, or Firm — MARSHALL, GERSTEIN & BORUN LLP

(57) ABSTRACT

Provided herein are polymers having a polymer backbone including a zwitterionic precursor monomeric unit having a secondary or tertiary amine in the polymer backbone, as well as methods of making and using the same.

12 Claims, 5 Drawing Sheets

(56) References Cited

OTHER PUBLICATIONS

Cao et al., Zwitteration of dextran: a facile route to integrate antifouling, switchability and optical transparency into natural polymers, Chem. Commun. 50 (2014) 3234-3237.
Carr et al., Functionalizable and nonfouling zwitterionic carboxybetaine hydroge I s with a carboxybetaine dimethacrylate crosslinker. Biomaterials 32 (2011) 961-968.
Chen et al., Highly pH-sensitive polyurethane exhibiting shape memory and drug release, Polym. Chem., 5:5168-74 (2014).
Chen et al., Strong Resistance of Phosphorylcholine Self-Assembled Monolayers to Protein Adsorption: Insights into Nonfouling Properties of Zwitterionic Materials, J. Am. Chem. Soc. 127 (2005) 14473-14478.
Cheng et al., A Switchable Biocompatible Polymer Surface with Self-Sterilizing and Nonfouling Capabilities, Angew. Chem. Int. Ed. 47 (2008) 8831-8834.
Cheng et al., Zwitterionic carboxybetaine polymer surfaces and their resistance to long-term biofilm formation, Biomaterials 30 (2009), 5234-5240.
Chuang et al., Regulation of polyurethane hemocompatibility and endothelialization by tethered hyaluronic acid oligosaccharides, Biomaterials, 30(29):5341-51 (2009).
Coneski et al., Zwitterionic Polyurethane Hydrogels Derived from Carboxybetaine-Functionalized Diols, ACS Appl. Mater. Interfaces 4 (2012) 4465-4469.
Costerton et al., Bacterial biofilms: a common cause of persistent infections, Science, 284(5418):1318-22 (1999).
Drenkard et al., Antimicrobial resistance of Pseudomonas aeruginosa biofilms, Microbes Infect., 5(13):1213-9 (2003).
Engels et al., Polyurethanes: versatile materials and sustainable problem solvers for today's challenges, Angew. Chem. Int. Ed. Engl., 52(36):9422-41 (2013).
Fang et al., Biodegradable poly(ester urethane)urea elastomers with variable amino content for subsequent functionalization with phosphorylcholine, Acta Biomater. 10 (2014) 4639-4649.
Gallagher et al., Main-chain zwitterionic supramolecular polymers derived from N-heterocyclic carbene-carbodiimide (NHC-CDI) adducts, Macromolecules, 51:3006-16 (2018).
Gogolewski, Selected topics in biomedical polyurethanes: A review, Colloid Polymer Sci., 267:757-85 (1989).
Gorna et al., Preparation, degradation, and calcification of biodegradable polyurethane foams for bone graft substitutes, J. Biomed. Mater. Res. A, 67(3):813-27 (2003).
Guelcher, Biodegradable polyurethanes: synthesis and applications in regenerative medicine, Tissue Eng. Part B Rev., 14(1):3-17 (2008).
He, et al., Zwitterionic materials for antifouling membrane surface construction, Acta Biomaterialia 40(2016) 142-152.
Hong et al., A small diameter, fibrous vascular conduit generated from a poly(ester urethane)urea and phospholipid polymer blend. Biomaterials 2009, 30 (13), 2457-2467.
Huang et al., Structure-rotein adsorption relationships of polyurethanes, J. Appl. Polym. Sci., 74:297-305 (1999).
International Application No. PCT/US19/28296, International Search Report and Written Opinion, mailed Aug. 22, 2019.
Jiang et al., Ultralow-Foulintt. Functionalizable. and Hydrolyzable Zwitterionic Materials andTheir Derivatives for Biological Applications, Adv. Mater. 22 (2012) 920-932.
Keefe, Poly(zwitterionic)protein conjugates offer increased stability without sacrificing binding affinity or bioactivity. nature chemistry 2012, 4, 59-63.
Kucharczyk et al., Degradation behaviour of PLA-based polyesterurethanes under abiotic and biotic environments, Polym. Degrad. Stab. 129 (2016) 222-230.
Guo et al., Design strategies and applications of citrate-based biodegradable elastomeric polymers, Chapter 16 In: Kumbar et al. (eds.), Natural and Synthetic Polymers, Elsevier (2014).

Leckband et al., Grafted Poly(ethylene oxide) Brushes as Nonfouling Surface Coatings, J. Biomater. Sci. Polym. Ed. 10(1999) 1125-1147.
Lee et al., Structure-Function Relationships of a Tertiary Amine-Based Polycarboxybetaine, Langmuir, 31(36):9965-72 (2015).
Liu et al.. Zwitterionic modification of polyurethane membranes for enhancing the anti-fouling property, J. Colloid Interface Sci. 480 (2016) 91-101.
Lowe et al., Synthesis and solution properties of zwitterionic polymers, Chem Rev 102 (2002) 4 177-4189.
Morral-Ruiz et al., Multifunctional polyurethane-urea nanoparticles to target and arrest inflamed vascular environment: a potential tool for cancer therapy and diagnosis, J. Control. Release, 171(2):163-71 (2013).
Nair et al., The Thiol-Michael Addition Click Reaction: A Powerful and Widely Used Tool in Materials Chemistry, Chem. Mater. 26 (2014) 724-744.
Nowatzki et al., Salicylic acid-releasing polyurethane acrylate polymers as anti-biofilm urological catheter coatings, Acta. Biomater., 8(5):1869-80 (2012).
Rojas et al., Polyurethane coatings release bioactive antibodies to reduce bacterial adhesion, J. Control. Release, 63(1-2):175-89 (2000).
Santerre et al., Understanding the biodegradation of polyurethanes: from classical implants to tissue engineering materials, Biomaterials, 26(35):7457-70 (2005).
Suresh et al., Electrospun polyurethane as an alternative ventricular catheter and in vitro model of shunt obstruction, J. Biomater. Appl., 29(7):1028-38 (2015).
Tan et al., Nonfouling biomaterials based on polyethylene oxide-containing amphiphilic triblock copolymers as surface modifying additives: protein adsorption on PEO-copolymer/polyurethane blends, J. Biomed. Mater. Res. A, 85(4):873-80 (2008).
Tsai et al., Human plasma fibrinogen adsorption and platelet adhesion to polystyrene, J. Biomed. Mater. Res. 13 44(1999) 130-139.
Villa-Diaz et al., Synthetic polymer coatings for long-term growth of human embryonic stem cells, Nat. Biotechnol. 28 (2010) 581-583.
Volkow et al., Polyurethane II catheter as long-indwelling intravenous catheter in patients with cancer, Am. J. Infect. Control., 31(7):392-6 (2003).
Wang et al., Zwitterionic Polyurethanes with Tunable Surface and Bulk Properties, ACS Appl. Mater. Interfaces, 10(43):37609-17 (2018).
Xu et al., A novel biocompatible zwitterionic polyurethane with AIE effect for cell imaging in living cells, RSC Advances, 8:6798 (2018).
Xuan et al., Preparation, characterization and application of zwitterionic polymers and membranes: current developments and perspective, Polym. Int. 58 (2009) 1350-1361.
Yang et al., Zwitterionic poly(carboxybetaine) hydrogels for glucose biosensors in complex media, Biosens. Bioelectron. 26 (2011) 2454-2459.
Ye et al., Biodegradable zwitterionic polymer coatings for magnesium alloy stents, Langmuir, 35(5):1421-9 (2019).
Ye et al.,Nonthrombogenic, Biodegradable Elastomeric Polyurethanes with Variable Sulfobetaine Content, ACS Appl. Mater. Interfaces 6 (2014) 22796-22806.
Yesudass et al., Zwitterionic-polyurethane coatings for non-specific marine bacterial inhibition: A nontoxic approach for marine application, Eur. Polym. J. 96 (2017) 304-315.
Zdrahala, Biomedical applications of polyurethane: a review in past promises, present realities and a vibrant future. Journal of Biomaterials Applications 1999, 14 (1), 67-90.
Zhang al., Superlow Fouling Sulfobetaine and Carboxybetaine Polymers on Glass Slides. Langmuir 2006, 22, 10072-10077.
Zhou et al., Synthesis of polyurethane-g-poly(ethylene glycol) copolymers by macroiniferter and their protein resistance, Polym. Chem. 2 (2011) 1409-1414.

\* cited by examiner

ZWITTERIONIC POLYMERS FOR BIOMEDICAL APPLICATIONS

CROSS-REFERENCE TO RELATED APPLICATION

This is the U.S. national phase of International Application No. PCT/US2019/028296, filed Apr. 19, 2019, which claims the benefit of priority to U.S. Provisional Patent Application 62/659,929, filed Apr. 19, 2018, the entire respective disclosure of which are each incorporated herein by reference.

BACKGROUND

Field of the Disclosure

This disclosure relates to polymers with tunable mechanical swelling properties having a zwitterionic precursor monomeric unit, uses thereof, and methods of preparation thereof.

Brief Description of Related Technology

Polyurethane (PU) comprises a large family of materials with the common characteristic that carries urethane linkages along the polymer backbone. In recent years, various PUs have been developed to provide good biocompatibility, high strength, high elasticity and processing versatility over a wide range of biomedical applications. These properties are important for in vivo applications, including catheters, drug delivery, tissue engineering, as well as in a variety of injection molded devices. Protein absorption on PUs, which is the initial stage of the blood coagulation cascade, was found to be slower or less than other materials due to hydrogen bond forming groups. This property makes PUs very attractive for a variety of medical applications that require both tunable strength and antithrombotic properties. However, there are several challenges remaining before fully realizing the potential of PU for these applications. First, anti-fouling properties of PU are unsatisfactory for applications in complex biological media (e.g., blood, body fluid and cell lysate). Second, most PUs do not possess both anti-fouling properties and functionality to conjugate other moieties. Thirdly, PU-based coatings can slightly reduce bacterial attachment, but cannot resist long-term biofilm formation. For example, biofilm formation on medical implants results in the formation of persistent infections that are up to 1000 times more resistant to conventional antibiotics than free bacteria. In response to these challenges, researchers have tried to incorporate hydrolysable/degradable or antifouling moieties into PUs to improve their anti-fouling properties. However, for degradable PU approach, the hydrophobic degradable moieties, such as polycaprolactone (PCL) or polylactic acid (PLA), still lead to the protein adsorption, since the degradation rate of the degradable moieties are significantly slower than the blood adsorption/coagulation rate. For anti-fouling approach, anti-fouling moieties, such as polyethylene glycol (PEG), have been incorporated into PU. Although PEG has been used alone or combined with other component for a broad spectrum of applications for anti-fouling purposes almost over 30 years, the critical challenges of PEG for in vivo applications, such as foreign body response, infection, and thrombosis, remain unsolved.

Zwitterionic materials, biologically inspired by phosphatidylcholine (PC) group in the phospholipid bilayer of cell membranes, possess both anionic and cationic groups with overall charge neutrality. Since they have been developed, zwitterionic materials have demonstrated excellent antifouling properties for blood, microorganisms, and mammalian cells. Compared to PEG-based surfaces, zwitterionic materials can form strong hydration layer via ionic solvation to resist foulants. With quaternary ammonium as common cationic groups, and phosphate, carboxylate or sulfonate as common anionic groups, zwitterionic polymers can be broadly classified into poly(phosphobetaine) (PPB), poly (carboxybetaine) (PCB) and poly(sulfobetaine) (PSB). Among them, PCB-based materials have demonstrated the outstanding antifouling properties of resisting proteins, mammalian cells and microbes, excellent biocompatibility as well as capability of functionalization for applications in biomedical devices.

In response to the challenges of PUs, some researchers are working on conjugating zwitterionic side chains, such as sulfobetaine (SB), carboxybetaine (CB), and phosphobetaine (PB) onto polyurethane backbones. In this case, James H. Wynne et al. reported that zwitterionic polyurethane hydrogels derived from carboxybetaine-functionalized diols showed a great capability of resistance to bacterial colonization, but it may need to use the strong base, sodium hydroxide, as the hydrolysis agent. Jian Shen et al. modified the polyurethane membrane using a PSB polymer brush to enhance the antifouling property, which created a successful antifouling surface. However, this method may be limited to different polyurethane materials.

Although the challenges remain for zwitterionic PUs due to the lack of chemistry, zwitterionic PUs still have the greatest potential for the most challenging in vivo applications. PUs can not only provide an antifouling surface/biointerface, but also have the tunable bulk mechanical properties. PU's morphology presents two very different structural phases: alternated hard and soft segments. Hard segments are responsible for high mechanical resilience while soft segments provide the PU an elastomeric behavior. Therefore, their singular molecular structure provide them good properties such as high strength, ductility, chemical stability, and ease of processability.

SUMMARY

In embodiments, a polymer can include a polymer backbone, the polymer backbone can include a first monomeric unit derived from a compound selected from the group consisting of an isocyanate, a diol, a polyol, and any combination thereof, and one or more second monomeric units, the one or more second monomeric units include a zwitterionic precursor monomeric unit, wherein the zwitterionic precursor monomeric unit includes a secondary or a tertiary amine within the polymer backbone. In embodiments, the polymer includes a second monomeric unit that is a zwitterionic precursor monomer unit having a secondary or tertiary amine within the polymer backbone. In embodiments, the polymer has two or more second monomeric units, each monomeric unit being a zwitterionic precursor monomer unit having a secondary or tertiary amine within the polymer backbone.

In embodiments of the disclosure, a polymer can include a polymer backbone, the polymer backbone can include a first monomeric unit and one or more second monomeric units, wherein the one or more second monomeric units include a zwitterionic precursor monomeric unit having a structure according to one or more of Formula (A1), (B1), (C1), (D1), and (E1):

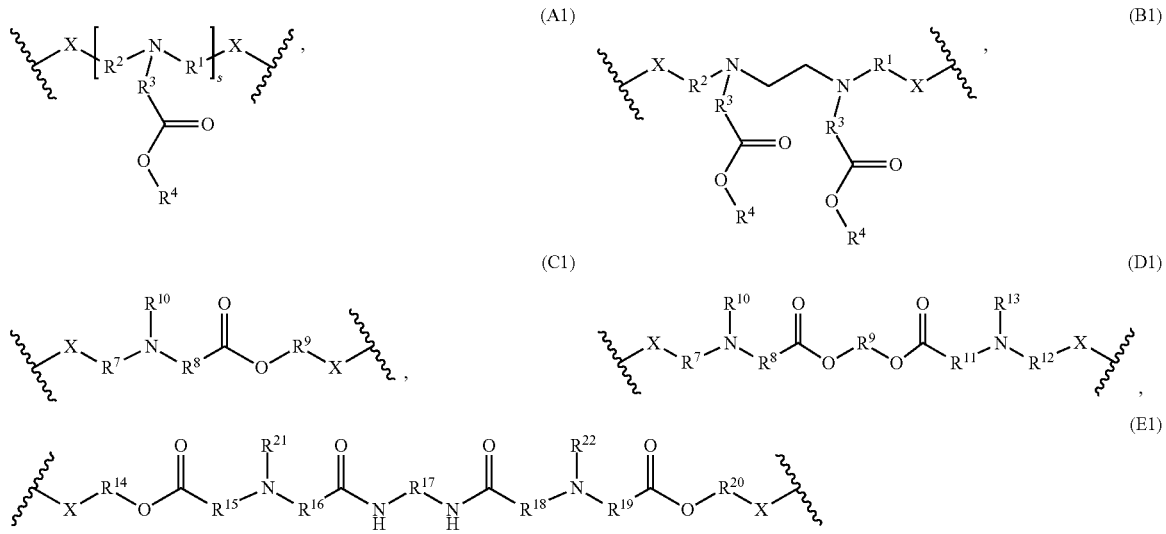

wherein in Formulas (A1) and (B1): each X is independently O, NR$^a$, S or Se; each R$^1$, R$^2$, and R$^3$ is independently selected from —(CH$_2$)$_n$—, —(CH$_2$)$_n$O(CH$_2$)$_m$—, —(CH$_2$CH$_2$OCH$_2$CH$_2$)$_n$—, —(CH$_2$CH$_2$O)$_n$CH$_2$CH$_2$—, —((CH$_2$)$_{1-8}$C(O)O)$_n$(CH$_2$)$_m$—, —((CH$_2$)$_{1-8}$C(O)O)$_n$(CH$_2$CH$_2$O)$_m$(OC(O)(CH$_2$)$_{1-8}$)$_p$—, —((CH$_2$)$_{1-8}$C(O)O)$_n$(CH$_2$CH$_2$)$_m$(OC(O)(CH$_2$)$_{1-8}$)$_p$—, —(CH$_2$C(O)O)$_m$(CH$_2$CH$_2$)$_n$(OC(O)CH$_2$)$_m$—, —(CH(CH$_3$)C(O)O)$_m$(CH$_2$CH$_2$)$_n$(OC(O)CH(CH$_3$))$_m$—, —(CH(CH$_3$)C(O)O)$_m$((CH$_2$)$_n$OC(O)O)(CH$_2$CH$_2$)$_m$, —(CH$_2$)$_n$NHC(O)(CH$_2$)$_m$—, and —(CH$_2$)$_n$C(O)NH(CH$_2$)$_m$; each R$^a$ and R$^4$ is independently selected from —H, —(CH$_2$CH$_2$O)$_n$CH$_3$, —(CH$_2$CH$_2$O)$_n$(CH$_2$)$_m$CH$_3$, —(CH$_2$CH$_2$O)$_n$(CH$_2$)$_m$OH, —((CH$_2$)$_n$O)$_m$((CH$_2$)$_p$O)$_q$(CH$_2$)$_r$OH, —(CH$_2$CH$_2$O)$_n$H, —(CH$_2$)$_n$OH, —(CH$_2$)$_n$O(CH$_2$)$_m$OH, —(CH$_2$CH$_2$OCH$_2$CH$_2$)$_n$OH, —((CH$_2$)$_{1-8}$C(O)O)$_n$(CH$_2$)$_m$OH, —((CH$_2$)$_{1-8}$C(O)O)$_n$(CH$_2$CH$_2$O)$_m$(OC(O)(CH$_2$)$_{1-8}$)$_p$OH, —((CH$_2$)$_{1-8}$C(O)O)$_n$(CH$_2$CH$_2$)$_m$(OC(O)(CH$_2$)$_{1-8}$)$_m$OH, —(CH$_2$C(O)O)$_n$(CH$_2$CH$_2$)$_m$(OC(O)CH$_2$)$_p$OH, —(CH(CH$_3$)C(O)O)$_n$(CH$_2$CH$_2$)$_m$(OC(O)CH(CH$_3$))$_p$OH, —((CH$_2$)$_n$OC(O)O)(CH$_2$CH$_2$)$_m$OH, —(CH$_2$)$_n$NHC(O)(CH$_2$)$_m$OH, and —(CH$_2$)$_n$C(O)NH(CH$_2$)$_m$OH, C$_{1-n}$ alkyl, C$_{1-n}$ alkenyl, C$_{1-n}$ alkynyl, C$_{6-10}$ aryl, and succinimidyl, wherein any one or more H atom of R$^a$ or R$^4$ can optionally be replaced with an F atom; and each n, m, p, q, r, and s is independently 1 to 10,000; and wherein in Formulas (C1), (D1), and (E1): each X is independently O, NR$^a$, S, or Se; each R$^7$, R$^8$, R$^9$, R$^{11}$, R$^{12}$, R$^{14}$, R$^{15}$, R$^{16}$, R$^{17}$, R$^{18}$, R$^{19}$ and R$^{20}$ is independently selected from —(CH$_2$)$_n$—, —((CH$_2$)$_n$O)$_m$((CH$_2$)$_p$O)$_q$(CH$_2$)$_r$—, —(CH$_2$)$_n$O(CH$_2$)$_m$—, —(CH$_2$CH$_2$OCH$_2$CH$_2$)$_n$—, —(CH$_2$CH$_2$O)$_n$CH$_2$CH$_2$—, —((CH$_2$)$_{1-8}$C(O)O)$_m$(CH$_2$)$_n$—, —((CH$_2$)$_{1-8}$C(O)O)$_m$(CH$_2$CH$_2$O)$_n$(OC(O)(CH$_2$)$_{1-8}$)$_p$—, —((CH$_2$)$_{1-8}$C(O)O)$_m$(CH$_2$CH$_2$)$_n$(OC(O)(CH$_2$)$_{1-8}$)$_p$—, —(CH$_2$C(O)O)$_m$(CH$_2$CH$_2$)$_n$(OC(O)CH$_2$)$_p$—, —(CH(CH$_3$)C(O)O)$_m$(CH$_2$CH$_2$)$_n$(OC(O)CH(CH$_3$))$_p$—, —(CH(CH$_3$)C(O)O)$_m$(CH$_2$CH$_2$)$_n$(OC(O)CH(CH$_3$))$_p$—, —((CH$_2$)$_n$OC(O)O)(CH$_2$CH$_2$)$_m$, —(CH$_2$)$_n$NHC(O)(CH$_2$)$_m$—, and —(CH$_2$)$_n$C(O)NH(CH$_2$)$_m$; each R$^a$, R$^{10}$, R$^{13}$, R$^{21}$, and R$^{22}$ is independently —H, —(CH$_2$CH$_2$O)$_n$CH$_3$, —(CH$_2$CH$_2$O)$_n$(CH$_2$)$_m$CH$_3$, —(CH$_2$CH$_2$O)$_n$(CH$_2$)$_m$OH, —((CH$_2$)$_n$O)$_m$((CH$_2$)$_p$O)$_q$(CH$_2$)$_r$OH, —(CH$_2$CH$_2$O)$_n$H, —(CH$_2$)$_n$OH, —(CH$_2$)$_n$O(CH$_2$)$_m$OH, —(CH$_2$CH$_2$OCH$_2$CH$_2$)$_n$OH, —(CH$_2$CH$_2$O)$_n$CH$_2$CH$_2$OH, —(CH$_2$CH$_2$OCH$_2$CH$_2$)$_n$OH, —((CH$_2$)$_{1-8}$C(O)O)$_n$(CH$_2$)$_m$OH, —((CH$_2$)$_{1-8}$C(O)O)$_n$(CH$_2$CH$_2$O)$_m$(OC(O)(CH$_2$)$_{1-8}$)$_p$OH, —((CH$_2$)$_{1-8}$C(O)O)$_n$(CH$_2$CH$_2$)$_m$(OC(O)(CH$_2$)$_{1-8}$)$_p$OH, —(CH$_2$C(O)O)$_n$(CH$_2$CH$_2$)$_m$(OC(O)CH$_2$)$_p$OH, —(CH(CH$_3$)C(O)O)$_n$(CH$_2$CH$_2$)$_m$(OC(O)CH(CH$_3$))$_p$OH, —(CH(CH$_3$)C(O)O)$_n$(CH$_2$CH$_2$)$_m$(OC(O)CH(CH$_3$))$_p$OH, —((CH$_2$)$_n$OC(O)O)(CH$_2$CH$_2$)$_m$OH, —(CH$_2$)$_n$NHC(O)(CH$_2$)$_m$OH, —(CH$_2$)$_n$C(O)NH(CH$_2$)$_m$OH, C$_{1-n}$ alkyl, C$_{1-n}$ alkenyl, C$_{1-n}$ alkynyl, or C$_{6-10}$ aryl, wherein any one or more H atoms of R$^a$, R$^{10}$, R$^{13}$, R$^{21}$, or R$^{22}$ can optionally be replaced with an F atom; and, each n, m, p, q and r is independently 1 to 10,000.

In the foregoing embodiments, the polymer includes a second monomeric unit that is a zwitterionic precursor monomer unit selected from Formula (A1), (B1), (C1), (D1), and (E1). In embodiments, the polymer has two or more second monomeric units, each monomeric unit being a zwitterionic precursor monomer unit independently selected from Formula (A1), (B1), (C1), (D1), and (E1).

In embodiments of the disclosure, an implantable medical device can include a polymer of any of the embodiments disclosed herein.

In accordance with embodiments, a method of preparing a polymer can include admixing a diol or polyol with an isocyanate to form a prepolymer solution; admixing the prepolymer solution with a zwitterionic precursor compound having a secondary or tertiary amine to form a modified prepolymer solution; and, exposing the modified prepolymer solution to conditions sufficient to initiate polymerization, thereby forming a polymer having a polymer backbone, wherein the secondary or tertiary amine of the zwitterionic precursor compound is within the polymer backbone.

In embodiments, a method of preparing a polymer can include admixing a zwitterionic precursor compound having a secondary or tertiary amine with an isocyanate to form a prepolymer solution admixing the prepolymer solution with a diol, polyol, diamine, or polyamine to form a modified prepolymer solution; and, exposing the modified prepolymer solution to conditions sufficient to initiate polymerization, thereby forming a polymer having a polymer backbone, wherein the secondary or tertiary amine of the zwitterionic precursor compound is within the polymer backbone.

In embodiments, a method of preparing a polymer can include admixing a zwitterionic precursor compound having a secondary or tertiary amine with an isocyanate and a diol or polyol to form a prepolymer solution; exposing the prepolymer solution to conditions sufficient to initiate polymerization, thereby forming a polymer having a polymer backbone, wherein the secondary or tertiary amine of the zwitterionic precursor compound is within the polymer backbone.

In embodiments, a method of preparing a polymer can include admixing a zwitterionic precursor compound with a first monomeric unit to form a prepolymer solution, exposing the prepolymer solution to conditions sufficient to initiate polymerization, thereby forming a polymer having a polymer backbone, wherein the zwitterionic precursor compound is within the polymer backbone. In embodiments, the zwitterionic precursor compound has a secondary or tertiary amine and upon polymerization the secondary or tertiary amine is within the polymer backbone.

Further aspects and advantages of the disclosure will be apparent to those of ordinary skill in the art from a review of the following detailed description. While the compositions and methods are susceptible of embodiments in various forms, the description hereafter includes specific embodiments, with the understanding that the disclosure is illustrative, and is not intended to limit the scope of the disclosure to the specific embodiments described herein.

DETAILED DESCRIPTION

Figure 1:
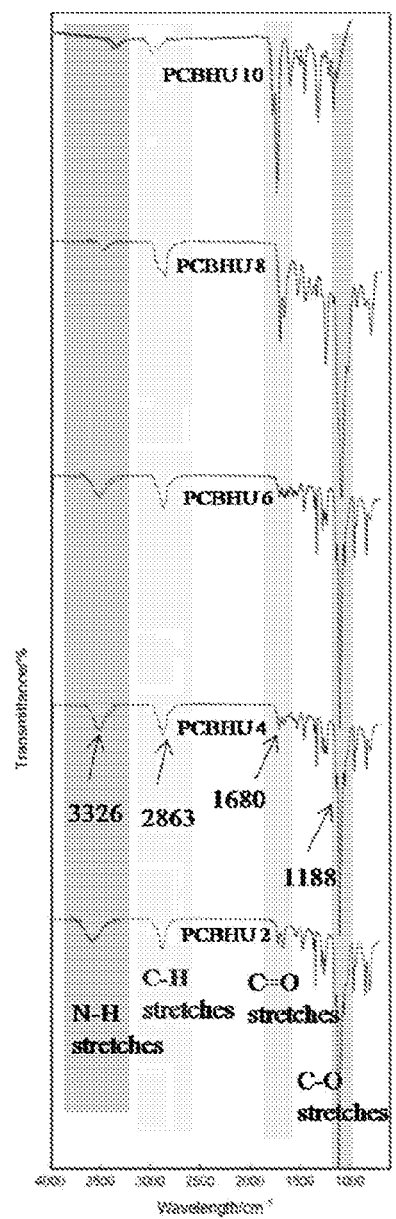
FIG. 1 shows the FT-IR spectrum of zwitterionic poly(carboxybetaine-urethane)s (PCBHU)s with different component ratios.

In accordance with embodiments, a polymer having anti-fouling and antimicrobial properties, as well as tunable mechanical properties, is provided with a polymer backbone including a first monomeric unit and one or more second monomeric units, wherein the one or more second monomeric units are each a zwitterionic precursor monomeric unit. In embodiments, the first monomeric unit is derived from a compound selected from an isocyanate, a diol, polyol, and any combination thereof. As is well understood in the art, a polymer is the reaction product of a plurality of monomers (e.g. diols, polyols, isocyanates, etc.) such that a polymer includes a plurality of monomeric units resulting from the reaction of those monomers. Consistent with this understanding, as used herein, the term "derived from" means that the monomeric unit is formed from the polymerization of the indicated monomer. For example, a monomeric unit derived from glycerol,

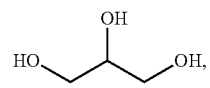

can have a structure of

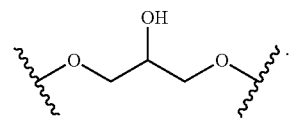 [SMILES: *OCC(O)CO*]

Polymers can include multiple distinct monomeric units resulting from the polymerization of different monomers. In embodiments, the zwitterionic precursor monomeric unit includes a secondary or tertiary amine, wherein the secondary or tertiary amine is within the polymer backbone.

Advantageously, the polymers of the disclosure provide improved anti-fouling and antimicrobial properties and have tunable mechanical properties. Furthermore, the polymers of the disclosure do not require subsequent, postprocessing functionalization to provide the polymer with the zwitterionic unit. Rather, the polymers can be hydrolyzed in an aqueous solution to provide the polymer with its zwitterionic properties, providing cost, time, and processability savings. Moreover, and advantageously, the hydrolysis of the polymers of the disclosure does not require a strong base, such as NaOH, and in some cases, can be carried out in deionized water.

In embodiments, the polymer has a molecular weight of about 1000 Da to about 10,000,000 Da, about 5000 Da to about 5,000,000 Da, about 5000 Da to about 1,000,000 Da, about 10,000 Da to about 1,000,000 Da, about 10,000 Da to about 500,000 Da, about 50,000 Da to about 500,000 Da, or about 100,000 Da to about 250,000 Da, for example about 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 120,000, 140,000, 160,000, 180,000, 200,000, 250,000, 300,000, 350,000, 400,000, 450,000, 500,000, 600,000, 700,000, 800,000, 900,000, 1,000,000, 1,500,000, 2,000,000, 2,500,000, 3,000,000, 4,000,000, 5,000,000, 6,000,000, 7,000,000, 8,000,000, 9,000,000, or 10,000,000 Da.

In embodiments, the polymer includes a hydrogel. In embodiments, the polyurethane composition includes an elastomer.

In embodiments, the polymer is non-degradable. In embodiments, the polymer is biodegradable. As used herein, the term "non-degradable" should be understood, as it is conventionally used, to mean that under the typical conditions to which the polymer is subjected to in use or by natural processes, the polymer does not degrade or does not substantially degrade over time. For example, a non-degradable polymer can be used to form an implantable medical device, such as a bone pin or screw, that, when inserted into a subject, will not degrade or will not substantially degrade over the lifetime of the subject. As used herein, "biodegradable," should be understood, as it is conventionally used, to mean that the polymer is capable of being degraded under the typical conditions to which the polymer is subjected and broken down into natural material. For example, a biodegradable polymer can be used to form an implantable medical device, such as an artery graft, that, when inserted into a subject, will degrade over time into natural materials that can be absorbed by the body of the subject, such that a surgeon or medical professional does not have to surgically remove the graft from the subject. The rate of degradation will depend on the various tunable properties of the polymer, such as, but not limited to, the monomeric units and the molecular weight.

The polymer of the disclosure includes a polymer backbone. In embodiments the polymer backbone includes repeating units of Formula (I):

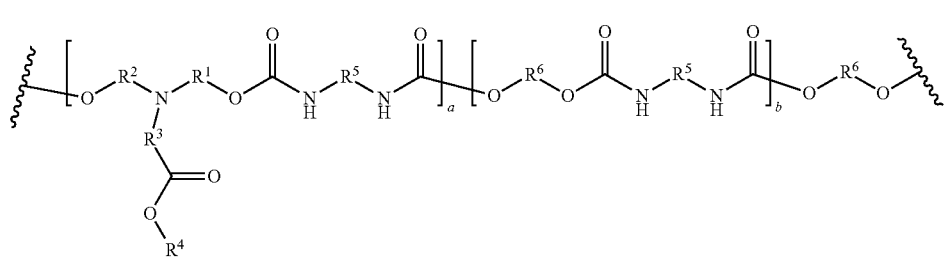

(I)

wherein $R^1$, $R^2$, $R^3$, $R^4$, $R^5$, $R^6$, $R^7$, a, and b are described in detail below.

In embodiments, the polymer backbone includes repeating units of Formula (II):

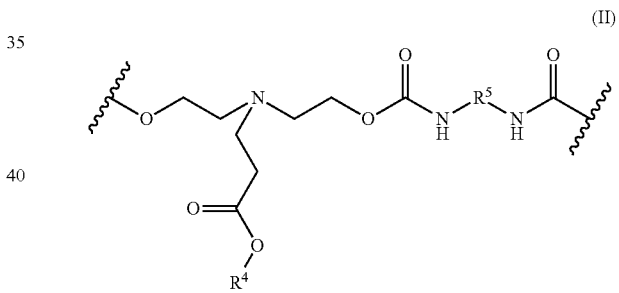

(II)

wherein $R^4$ and $R^5$ are described in detail below. In embodiments, the polymer having a polymer backbone including repeating units of Formula (II) has a molecular weight of about 1,000 to about 10,000,000 Da.

In embodiments, the polymer backbone includes repeating units of Formula (III):

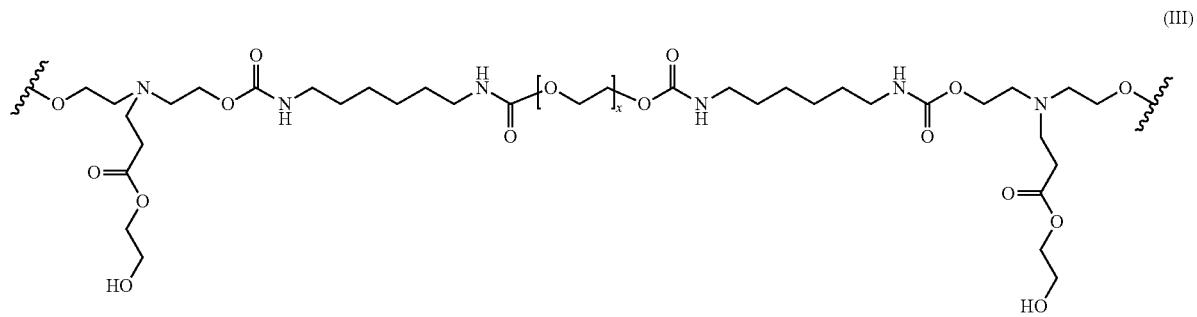

(III)

wherein x is 1 to 1,000,000, 1 to 100,000 1 to 10,000, 1 to 1000, or 1 to 100, for example, 1, 5, 10, 20, 30, 40, 50, 60, 70, 80, 90, 100, 250, 500, 750, 1000, 2000, 3000, 4000, 5000, 6000, 7000, 8000, 9000, 10,000, 15,000, 20,000, 30,000, 40,000, 50,000, 60,000, 70,000, 80,000, 90,000, 100,000, 200,000, 300,000, 400,000, 500,000, 600,000, 700,000, 800,000, 900,000, or 1,000,000. In embodiments, the polymer having a polymer backbone including repeating units of Formula (III) has a molecular weight of about 1,000 to about 10,000,000 Da.

In embodiments, the polymer backbone includes repeating units of Formula (IV):

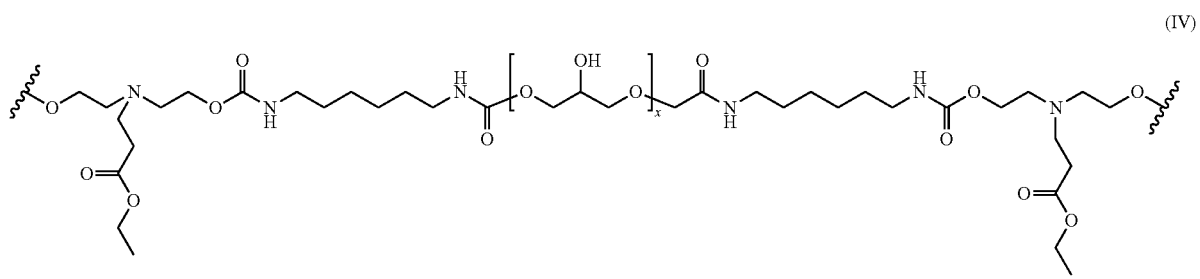

(IV)

wherein x is 1 to 1,000,000, 1 to 100,000, 1 to 10,000, 1 to 1000, or 1 to 100, for example, 1, 5, 10, 20, 30, 4,0, 50, 60, 70, 80, 90, 100, 250, 500, 750, 1000, 2000, 3000, 4000, 5000, 6000, 7000, 8000, 9000, 10,000, 15,000, 20,000, 30,000, 40,000, 50,000, 60,000, 70,000, 80,000, 90,000, 100,000, 200,000, 300,000, 400,000, 500,000, 600,000, 700,000, 800,000, 900,000, or 1,000,000.

In embodiments, the polymer backbone includes repeating units of Formula (V):

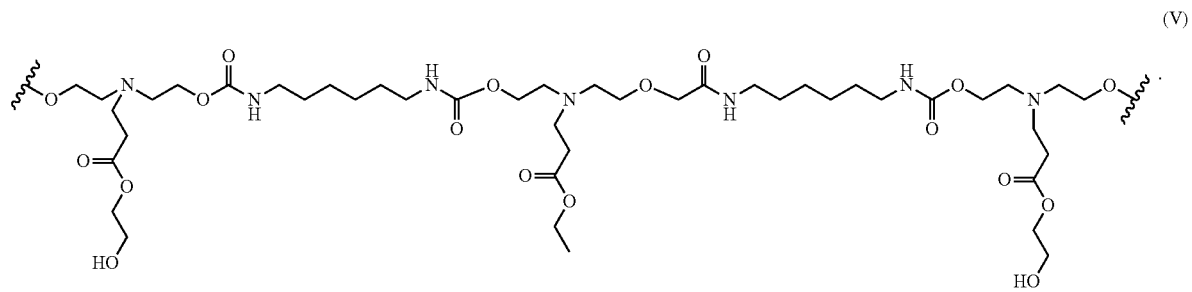

(V)

In embodiments, the polymer backbone includes repeating units of Formula (VI):

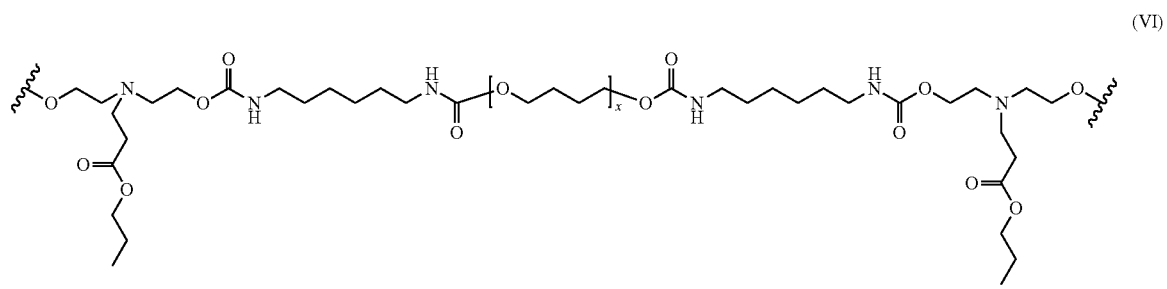

(VI)

wherein x is 1 to 1,000,000, 1 to 100,000, 1 to 10,000, 1 to 1000, or 1 to 100, for example, 1, 5, 10, 20, 30, 4,0, 50, 60, 70, 80, 90, 100, 250, 500, 750, 1000, 2000, 3000, 4000, 5000, 6000, 7000, 8000, 9000, 10,000, 15,000, 20,000, 30,000, 40,000, 50,000, 60,000, 70,000, 80,000, 90,000, 100,000, 200,000, 300,000, 400,000, 500,000, 600,000, 700,000, 800,000, 900,000, or 1,000,000.
In embodiments, the polymer backbone includes repeating units of Formula (VII):
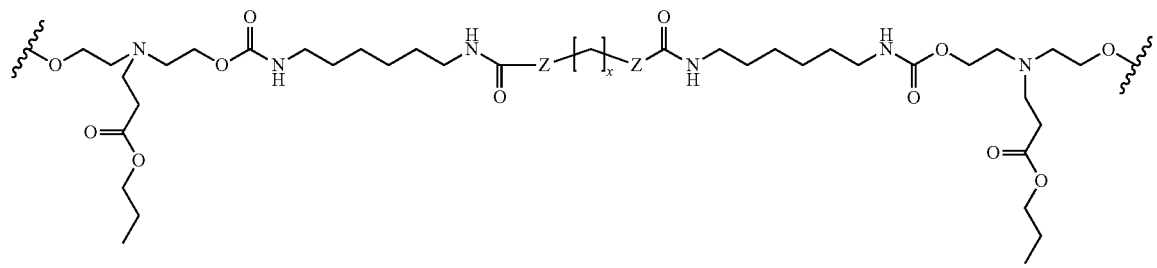
(VII)
wherein Z is O or NH, and x is 1 to 30, 1 to 20, 1 to 15, 1 to 10, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In some cases, Z is O. In some cases, Z is NH. For example, in embodiments, the polymer backbone includes repeating units of Formula (VIII-A), (VIII-B), and/or (VIII-C):
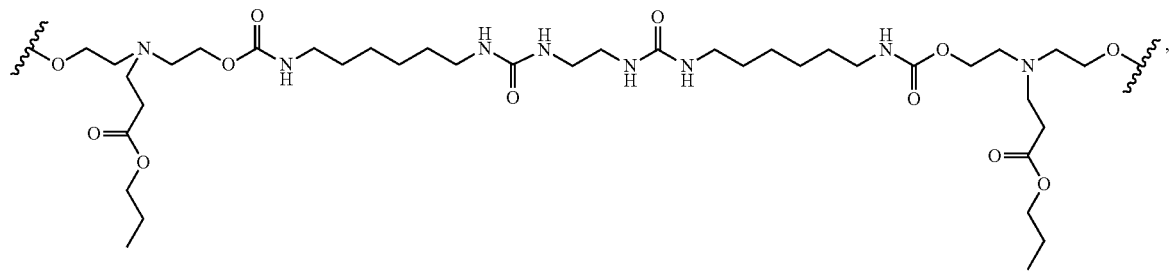
(VIII-A)
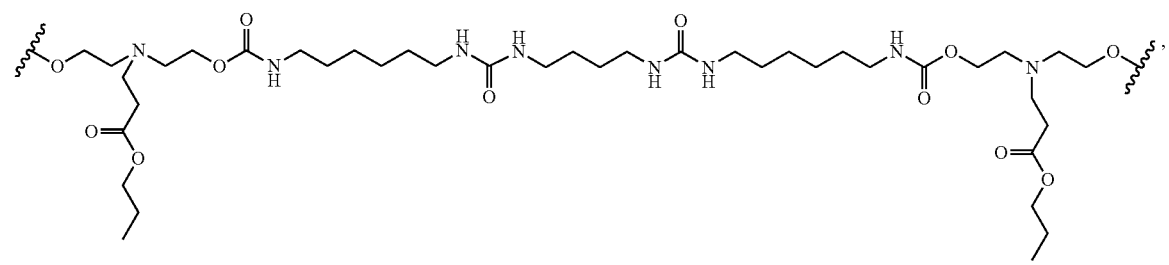
(VIII-B)
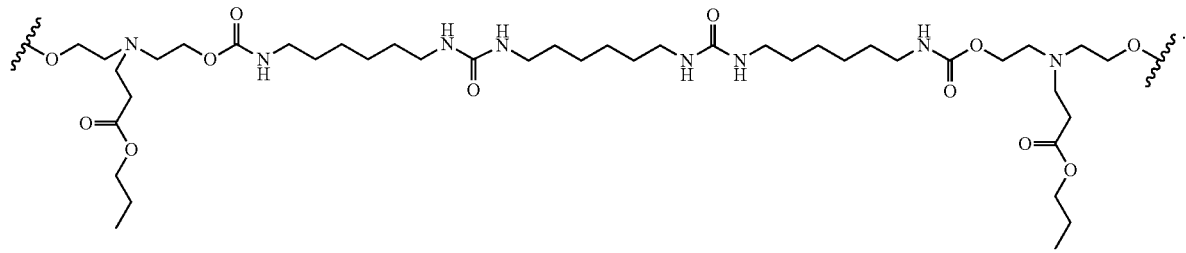
(VIII-C)

In embodiments, the polymer backbone includes repeating units of Formula (IX):

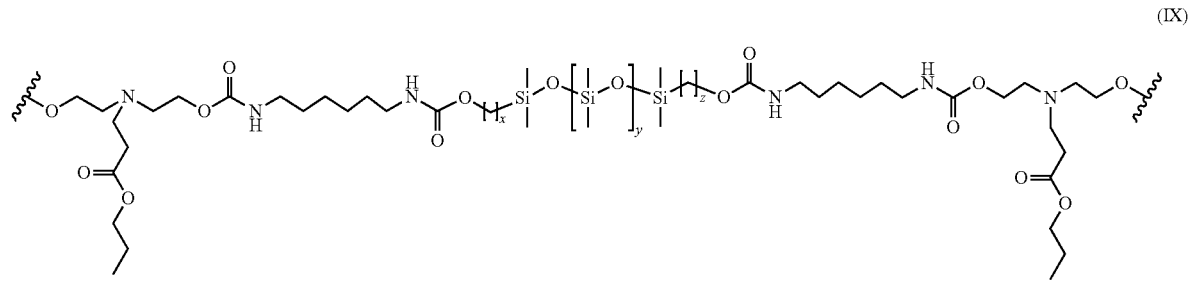

(IX)

wherein x and z are each 0 to 20, 1 to 15, or 2 to 10, for example 0, 1, 2, 3, 4, 5, 6, 7, 8, 9, 10, 11, 12, 13, 14, 15, 16, 17, 18, 19, or 20, and y is 1 to 1,000,000, 1 to 100,000, 1 to 10,000, 1 to 1000, or 1 to 100, for example, 1, 5, 10, 20, 30, 4,0, 50, 60, 70, 80, 90, 100, 250, 500, 750, 1000, 2000, 3000, 4000, 5000, 6000, 7000, 8000, 9000, 10,000, 15,000, 20,000, 30,000, 40,000, 50,000, 60,000, 70,000, 80,000, 90,000, 100,000, 200,000, 300,000, 400,000, 500,000, 600,000, 700,000, 800,000, 900,000, or 1,000,000.

In embodiments, the polymer backbone includes repeating units of Formula (X):

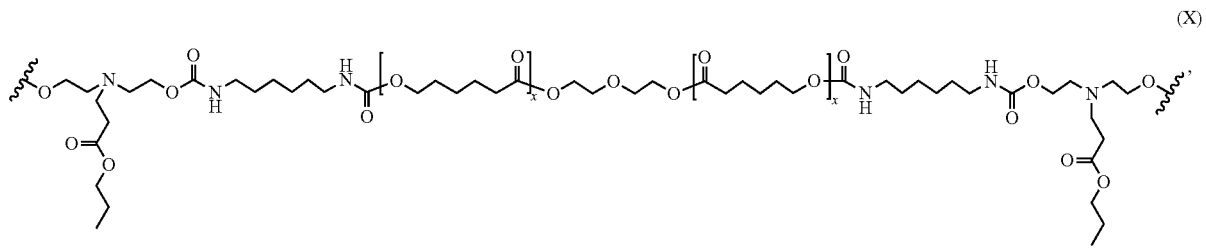

(X)

wherein each x is 0 to 1,000,000, 1 to 100,000, 1 to 10,000, 1 to 1000, or 1 to 100, for example, 0, 1, 5, 10, 20, 30, 4,0, 50, 60, 70, 80, 90, 100, 250, 500, 750, 1000, 2000, 3000, 4000, 5000, 6000, 7000, 8000, 9000, 10,000, 15,000, 20,000, 30,000, 40,000, 50,000, 60,000, 70,000, 80,000, 90,000, 100,000, 200,000, 300,000, 400,000, 500,000, 600,000, 700,000, 800,000, 900,000, or 1,000,000.

In embodiments, the polymer backbone includes repeating units of Formula (XI)

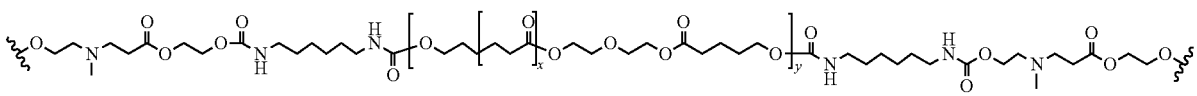

(XI), wherein each of x and y is 0 to 1,000,000, 1 to 100,000, 1 to 10,000, 1 to 1000, or 1 to 100, for example, 0, 1, 5, 10, 20, 30, 4,0, 50, 60, 70, 80, 90, 100, 250, 500, 750, 1000, 2000, 3000, 4000, 5000, 6000, 7000, 8000, 9000, 10,000, 15,000, 20,000, 30,000, 40,000, 50,000, 60,000, 70,000, 80,000, 90,000, 100,000, 200,000, 300,000, 400,000, 500,000, 600,000, 700,000, 800,000, 900,000, or 1,000,000.

In embodiments, the polymer backbone includes repeating units of Formula (XII)

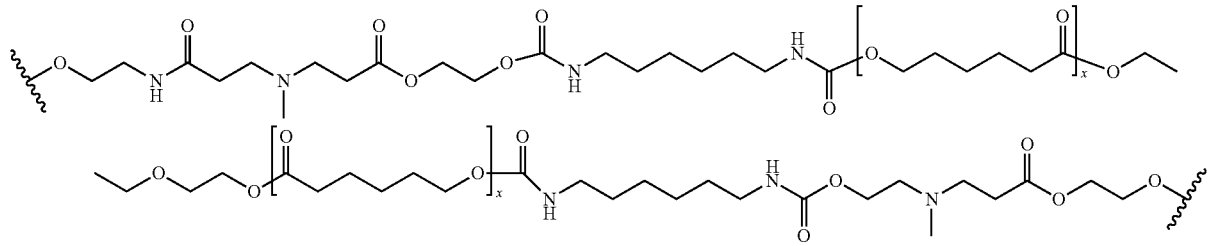

(XII), wherein each of x is 0 to 1,000,000, 1 to 100,000, 1 to 10,000, 1 to 1000, or 1 to 100, for example, 0, 1, 5, 10, 20, 30, 4,0, 50, 60, 70, 80, 90, 100, 250, 500, 750, 1000, 2000, 3000, 4000, 5000, 6000, 7000, 8000, 9000, 10,000, 15,000, 20,000, 30,000, 40,000, 50,000, 60,000, 70,000, 80,000, 90,000, 100,000, 200,000, 300,000, 400,000, 500,000, 600,000, 700,000, 800,000, 900,000, or 1,000,000.

In embodiments, the ratio of hydroxyl groups in the zwitterionic precursor monomeric unit:hydroxyl groups in the diol or polyol:isocyanate groups in the isocyanate ranges from about 1:9999:10,000 to about 10,000:0:10,000, or about 1:999:1000 to about 1000:0:1000, for example, 2:8:10, 4:6:10, 6:4:10, 8:2:10, or 10:0:10, 100:0:100, 75:25:100, 50:50:100, 25:75:100, or 0:100:100. In some cases, the ratio is 2:8:10, 4:6:10, 6:4:10, 8:2:10, or 10:0:10.

In embodiments, the polymer is hydrolyzed. Hydrolysis of the polymers described herein provides zwitterionic polymers. For example, after hydrolysis, the polymer can include a monomeric unit having a structure:

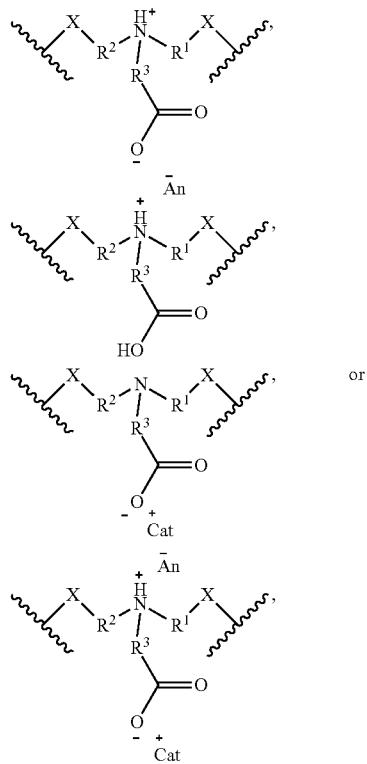

wherein each of $R^1$, $R^2$, and $R^3$ are described in detail below, "An" is an organic or inorganic anion and "Cat" is an organic or inorganic cation.

First Monomeric Unit

The polymer provided herein includes a first monomeric unit.

In embodiments, the first monomeric unit is derived from a compound includes an isocyanate, a diol, a polyol, a diamine, a polyamine, and/or any combination thereof.

In embodiments, the first monomeric unit is derived from an isocyanate. The isocyanate can include a diisocyanate and/or a polyisocyanate. Examples of suitable isocyanates include, but are not limited to, isocyanate, isocyanate PEG, 4,4-methylenebis(phenyl isocyanate), 4,4-methylenebis(cyclohexyl isocyanate), 4,4'-oxybis(phenyl isocyanate), 3arm-PEG-isocyanate, 4arm-PEG-isocyanate, bis(4-isocyanatophenyl)methane, 4,4'-methylenebis(2-chlorophenyl isocyanate), 3,3'-dichloro-4,4'-diisocyanato-1,1'-biphenyl, hexamethylene diisocyanate (HDI), 1,4-phenylene diisocyanate, 1,3-phenylene diisocyanate, m-xylylene diisocyanate, tolylene-2,4-diisocyanate, tolylene-2,6-diisocyanate, poly (hexamethylene diisocyanate), trans-1,4-cyclohexylene diisocyanate, 4-chloro-6-methyl-1,3-phenylene diisocyanate, 1,4-diisocyanatobutane, 1,8-diisocyanatooctane, 1,3-bis(1-isocyanato-I-methylethyl)benzene, 3,3'-dimethyl-4,4'-biphenylene diisocyanate, 1,12-diisocyanatododecane, polyisocyanate, or any combination thereof. In some cases, the isocyanate includes hexamethylene diisocyanate (HDI).

In embodiments, the first monomeric unit is derived from a diol. In embodiments, the first monomeric unit is derived from a polyol. Examples of suitable diols or polyols include, but are not limited to, poly(ethylene glycol) (PEG), ethylene glycol, diethylene glycol, triethylene glycol, tetraethylene glycol, propylene glycol, dipropylene glycol, tripropylene glycol, 1,3-propanediol, 1,3-butanediol, 1,4-butanediol, neopentyl glycol, 1,6-hexanediol, 1,4-cyclohexanedimethanol, trimethylolpropane, 1,2,6-hexanetriol, triethanolamine, pentaerythritol, glycerol, N,N,N',N'-tetrakis (2-hydroxypropyl)ethylenediamine, polytetrahydrofuran (PTHF) diol, polytetrahydrofuran (PTHF) triol, polycaprolactone (PCL) diol, polycaprolactone (PCL) triol, polycaprolactone (PCL) polyol, polydimethylsiloxane (PDMS) diol, polydimethylsiloxane (PDMS) triol, polydimethylsiloxane (PDMS) polyol, polyester diol, polyester triol, polylactide (PLA) diol, polylactide (PLA) triol, polypeptides, polyester, polyether, polyamide, octanediol, fluoroalkane polyol, fluoroalkene polyol, fluoroalkyne polyol, alkane polyol, alkene polyol, alkyne polyol, aromatic polyol, poly(vinyl alcohol), polysaccharide, poly(2-hydroxyethyl methacrylate) (pHEMA), poly(2-hydroxyethyl acrylate), poly(N—Hydroxyethyl acrylamide), poly(N-(Hydroxymethyl)acrylamide), poly(N-tris(hydroxymethyl)methylacrylamide), poly((methyl)acrylate) polyol, poly((methyl)acrylamide) polyol, poly(polytetrahydrofuran carbonate) diol, polycarbonate diol, polycarbonate polyol, or any combination thereof.

In embodiments, the first monomeric unit is derived from poly(ethylene glycol). The poly(ethylene glycol) can have a molecular weight ranging from about 200 Da to about 10,000 Da, about 200 to about 5000 Da, about 200 Da to about 1000 Da, or about 1000 to about 5000 Da, for example, about 200, 250, 300, 400, 500, 600, 700, 800, 900, 1000, 1250, 1500, 1750, 2000, 2500, 3000, 3500, 4000, 4500, 5000, 6000, 7000, 8000, 9000, or 10,000 Da. The molecular weight of PEG can be selected to impart improved elasticity to the polymer. For example, PEG 2000 includes longer soft segments that impart elasticity to the polymer. However, if the PEG soft segments are too long, the mechanical strength of the polymer can be compromised.

In embodiments, the first monomeric unit is derived from glycerol.

In embodiments, the first monomeric unit is derived from a diamine. In embodiments, the first monomeric unit is derived from a polyamine. Examples of suitable diamines or polyamines include, but are not limited to, methanediamine, ethylenediamine, 1,1-dimethylethylenediamine, 1,2-dimethylethylenediamine, ethambutol, TMEDA, 1,3-diaminopropane, putrescine, cadaverine, hexamethylenediamine, trimethylhexamethylenediamine, 1,2-diaminopropane, diphenylethylenediamine, trans-1,2,diaminocyclohexane, 1,4-diazacyclohexane, o-phenylenediamine, m-phenylenediamine, p-phenylenediamine, 2,5-diaminotoluene, dimethyl-4-phenylenediamine, N,N'-di-2-butyl-1,4-phenylenediamine, 4,4'-diaminobiphenyl, 1,8-diaminonapthalene, diethylenetriamine, pentamethyldiethylenetriamine, triethylenetetramine, tetraethylenepentamine, pentaethylenehexamine, 1,4,7-triazacyclonane, tris(2-aminoethyl)amine, polyethylene amine, or 1,1,1-tris(aminomethyl)ethane.

Zwitterionic Precursor Monomeric Units

The polymers of the disclosure include one or more second monomeric units. The one or more second monomeric units include a zwitterionic precursor monomeric unit having at least one functional group, wherein the at least one functional group of the zwitterionic precursor compound is incorporated into the polymer backbone. In embodiments, the zwitterionic precursor compound includes a secondary or tertiary amine and the secondary or tertiary amine is within the polymer backbone.

As used herein, the term "zwitterionic precursor monomeric unit" refers to a monomeric unit that is capable of becoming zwitterionic. That is, the monomeric unit includes both a functional group that is capable of holding a positive charge, and a functional group that is capable of holding a negative charge, simultaneously. For example, the polymer having the zwitterionic precursor unit can be hydrolyzed to provide a zwitterionic polymer having a balance of positive and negative charges on various atoms and/or functional groups of the zwitterionic precursor monomeric unit. Alternatively, or additionally, "zwitterionic precursor monomeric unit" refers to a moiety chemically bonded to the polymer backbone including one or more functional groups that can be converted to zwitterionic functional groups, including carboxybetaine, sulfobetaine, and phosphobetaine, by hydrolysis, chemical agents, heat, radiation, electricity, oxidation, or reduction.

In embodiments, the zwitterionic precursor monomeric unit has a structure according to one or more of Formula (A1), (B1), (C1), (D1), and (E1):

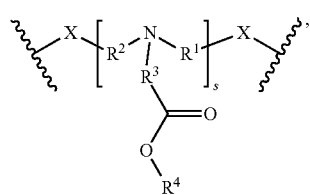

(A1)

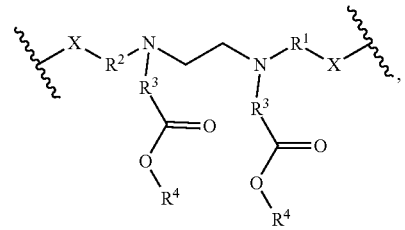

(B1)

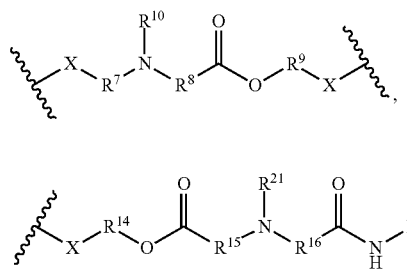

(C1)

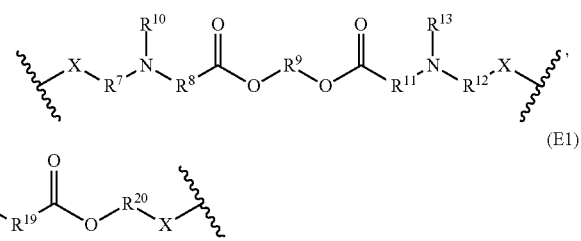

(D1)

(E1)

Formulas (A1) and (B1)

In embodiments, the zwitterionic precursor monomeric unit has a structure according to Formula (A1) or (1).

In embodiments, each X is independently O, $NR^a$, S or Se. In some cases, each X is O. In some cases, each X is $NR^a$. In some cases, each X is S. In some cases, each X is Se. Each X in the zwitterionic precursor unit does not have to be the same as the other X, for example, one X can be O, while the other X is $NR^a$.

In embodiments, each $R^1$, $R^2$, and $R^3$ is independently selected from $—(CH_2)_n—$, $—(CH_2)_nO(CH_2)_m—$, $—(CH_2CH_2OCH_2CH_2)_n—$, $—(CH_2CH_2O)_nCH_2CH_2—$, $—((CH_2)_{1-8}C(O)O)_n(CH_2)_m—$, $—((CH_2)_{1-8}C(O)O)_n(CH_2CH_2O)_m(OC(O)(CH_2)_{1-8})_p—$, $—((CH_2)_{1-8}C(O)O)_n(CH_2CH_2)_m(OC(O)(CH_2)_{1-8})_p—$, $—(CH_2C(O)O)_m(CH_2CH_2)_n(OC(O)CH_2)_m—$, $—(CH(CH_3)C(O)O)_m(CH_2CH_2)_n(OC(O)CH(CH_3))_m—$, $—(CH(CH_3)C(O)O)_m(CH_2CH_2)_n(OC(O)CH(CH_3))_m—$, $—((CH_2)_nOC(O)O(CH_2CH_2)_m—$, $—(CH_2)_nNHC(O)(CH_2)_m—$, and $—(CH_2)_nC(O)NH(CH_2)_m—$.

In embodiments, $R^1$ is —$(CH_2)_2$—. In embodiments, $R^2$ is —$(CH_2)_2$—. In embodiments, $R^3$ is —$(CH_2)_{1-5}$—. In embodiments, $R^3$ is —$(CH_2)_2$—.

In embodiments, each $R^a$ and $R^4$ is independently selected from —H, —$(CH_2CH_2O)_nCH_3$, —$(CH_2CH_2O)_n(CH_2)_mCH_3$, —$(CH_2CH_2O)_n(CH_2)_mOH$, —$((CH_2)_nO)_m((CH_2)_pO)_q(CH_2)_nOH$, —$(CH_2CH_2O)_nH$, —$(CH_2)_nOH$, —$(CH_2)_nO(CH_2)_mOH$, —$(CH_2CH_2OCH_2CH_2)_nOH$, —$(CH_2CH_2O)_nCH_2CH_2OH$, —$((CH_2)_{1-8}C(O)O)_n(CH_2)_mOH$, —$((CH_2)_{1-8}C(O)O)_n(CH_2CH_2O)_m(OC(O)(CH_2)_{1-8})_pOH$, —$((CH_2)_{1-8}C(O)O)_n(CH_2CH_2)_m(OC(O)(CH_2)_{1-8})_mOH$, —$(CH_2C(O)O)_n(CH_2CH_2)_m(OC(O)CH_2)_pOH$, —$(CH(CH_3)C(O)O)_n(CH_2CH_2)_m(OC(O)CH(CH_3))_pOH$, —$((CH_2)_nOC(O)O)(CH_2CH_2)_mOH$, —$(CH_2)_nNHC(O)(CH_2)_mOH$, and —$(CH_2)_nC(O)NH(CH_2)_mOH$, $C_{1-n}$ alkyl, $C_{1-n}$ alkenyl, $C_{1-n}$ alkynyl, $C_{6-10}$ aryl, and succinimidyl, wherein any one or more H atoms of $R^a$ or $R^4$ can optionally be replaced with an F atom.

In embodiments, $R^4$ is —H. In embodiments, $R^4$ is —F. In embodiments, $R^4$ is —$CH_3$. In embodiments, $R^4$ is —$CH_2CH_3$. In embodiments, $R^4$ is —$(CH_2)_2OH$. In embodiments, $R^4$ is $(CH_2)_{1-5}$. In embodiments, $R^4$ is butyl. In embodiments, $R^4$ is tert-butyl. In embodiments, $R^4$ is pentafluorophenyl.

In embodiments, each n, m, p, q, r, and s is independently 1 to 10,000, 1 to 5000, 1 to 2500, 1 to 1000, 1 to 500, 1 to 100, or 1 to 10, for example, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 1250, 1500, 1750, 2000, 2500, 3000, 3500, 4000, 4500, 5000, 6000, 7000, 8000, 9000, or 10,000.

In embodiments, the zwitterionic precursor monomeric unit has a structure:

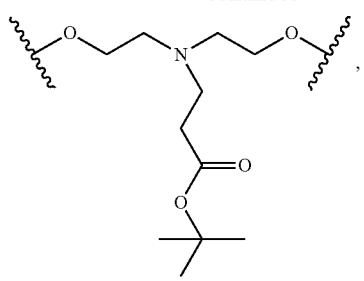

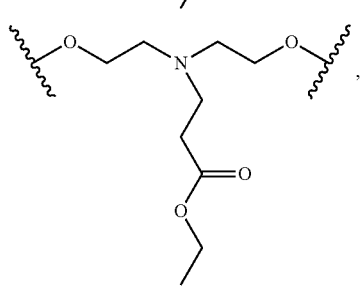

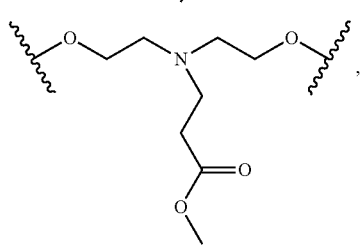

-continued

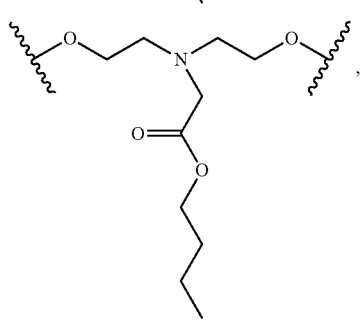

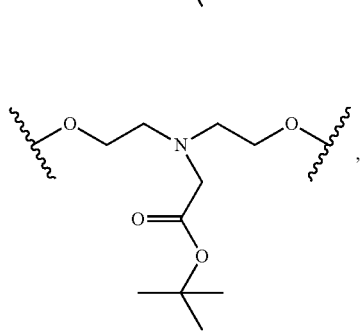

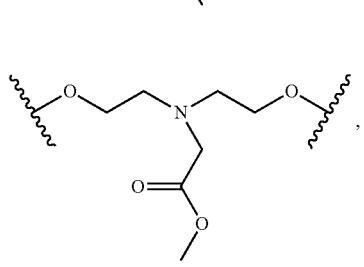

21
-continued
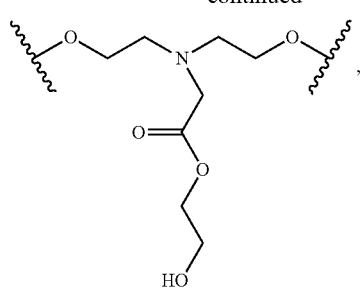
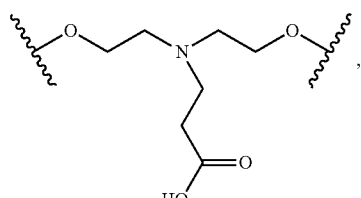
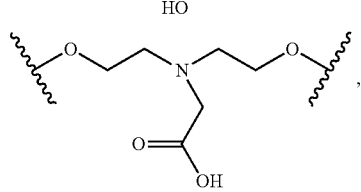
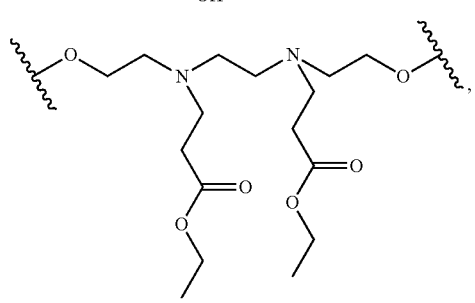
22
-continued
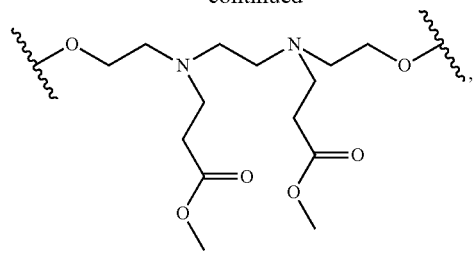
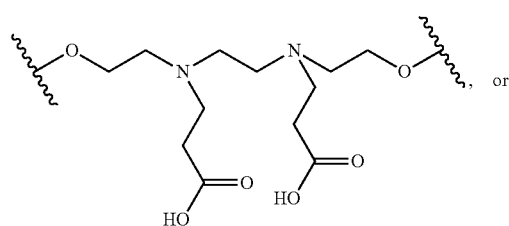, or
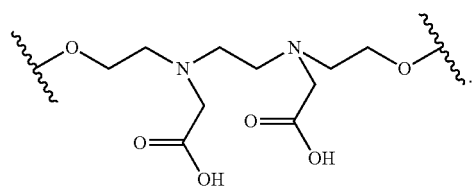
As provided above, in embodiments the polymer backbone includes repeating units of Formula (I) or (II):
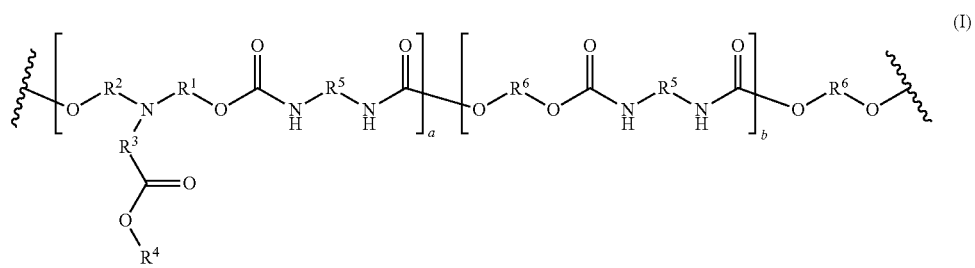
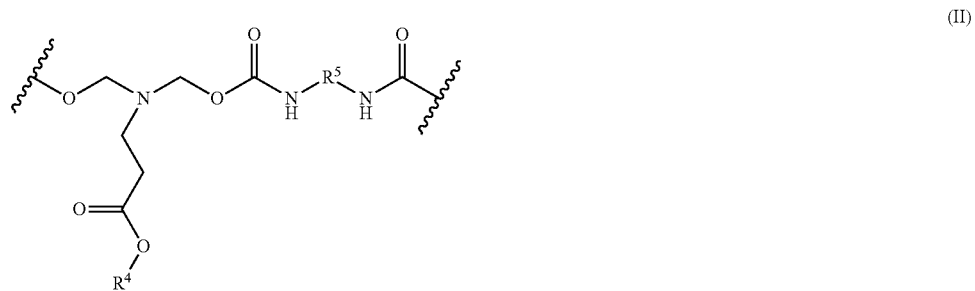

wherein each of $R^1$, $R^2$, $R^3$, and $R^4$ are described, above.

In embodiments, each of $R^5$ and $R^6$ is independently —$(CH_2)_n$—, —$(CH_2)_nO(CH_2)_m$—, —$(CH_2CH_2OCH_2CH_2)_n$—, —$(CH_2CH_2O)_nCH_2CH_2$—, —$(CH_2CH_2O)_n(CH_2)_m$—, —$(CH_2)_n(CH_2CH_2O)_n(CH_2)_p$—, —$((CH_2)_{1-8}C(O)O)_n(CH_2)_m$—, —$((CH_2)_{1-8}C(O)O)_n(CH_2CH_2O)_m(OC(O)(CH_2)_{1-8})_p$—, —$((CH_2)_{1-8}C(O)O)_n(CH_2CH_2)_m(OC(O)(CH_2)_{1-8})_p$—, —$(CH_2C(O)O)_n(CH_2CH_2)_m(OC(O)CH_2)_p$—, —$(CH(CH_3)C(O)O)_n(CH_2CH_2)_m(OC(O)CH(CH_3))_p$—, —$(CH(CH_3)C(O)O)_n(CH_2CH_2)_m(OC(O)CH(CH_3))_p$—, —$((CH_2)_nOC(O)O)(CH_2CH_2)_m$—, —$(CH_2)_nNHC(O)(CH_2)_m$—, —$(CH_2)_nC(O)NH(CH_2)_m$, or —$(CH_2)_nCH(OH)(CH_2)_m$—.

In some cases, $R^5$ is —$(CH_2)_6$—.

In some cases, $R^6$ is —$(CH_2CH_2O)_nCH_2CH_2$—. In some cases, $R^6$ is —$(CH_2)_nCH(OH)(CH_2)_m$—. In some cases, $R^6$ is —$(CH_2)CH(OH)(CH_2)$—.

In embodiments, a is 1 to 100,000, 1 to 10,000, 1 to 1000, or 1 to 100, for example, 1, 5, 10, 20, 30, 4,0, 50, 60, 70, 80, 90, 100, 250, 500, 750, 1000, 2000, 3000, 4000, 5000, 6000, 7000, 8000, 9000, 10,000, 15,000, 20,000, 30,000, 40,000, 50,000, 60,000, 70,000, 80,000, 90,000, or 100,000.

In embodiments, b is 0 to 100,000, 1 to 10,000, 1 to 1000, or 1 to 100, for example, 0, 1, 5, 10, 20, 30, 4,0, 50, 60, 70, 80, 90, 100, 250, 500, 750, 1000, 2000, 3000, 4000, 5000, 6000, 7000, 8000, 9000, 10,000, 15,000, 20,000, 30,000, 40,000, 50,000, 60,000, 70,000, 80,000, 90,000, or 100,000.

Formulas (C1), (D1), and (E1)

In embodiments, the zwitterionic precursor monomeric unit has a structure of (C1), (D1), or (E1).

In embodiments, each X is independently O, $NR^a$, S, or Se. In some cases, each X is O. In some cases, each X is $NR^a$. In some cases, each X is S. In some cases, each X is Se. Each X in the zwitterionic precursor unit does not have to be the same as the other X, for example, one X can be O, while the other X is $NR^a$.

In embodiments, each $R^7$, $R^8$, $R^9$, $R^{11}$, $R^{12}$, $R^{14}$, $R^{15}$, $R^{16}$, $R^{17}$, $R^{18}$, $R^{19}$ and $R^{20}$ is independently selected from —$(CH_2)_n$—, —$((CH_2)_nO)_m((CH_2)_pO)_q(CH_2)_r$—, —$(CH_2)_nO(CH_2)_m$—, —$(CH_2CH_2OCH_2CH_2)_n$—, —$(CH_2CH_2O)_nCH_2CH_2$—, —$((CH_2)_{1-8}C(O)O)_m(CH_2)_n$—, —$((CH_2)_{1-8}C(O)O)_m(CH_2CH_2)_n(OC(O)(CH_2)_{1-8})_p$—, —$((CH_2)_{1-8}C(O)O)_m(CH_2CH_2)_n(OC(O)(CH_2)_{1-8})_p$—, —$(CH_2C(O)O)_m(CH_2CH_2)_n(OC(O)CH_2)_p$—, —$(CH(CH_3)C(O)O)_m(CH_2CH_2)_n(OC(O)CH(CH_3))_p$—, —$(CH(CH_3)C(O)O)_m(CH_2CH_2)_n(OC(O)CH(CH_3))_p$—, —$((CH_2)_nOC(O)O)(CH_2CH_2)_m$—, —$(CH_2)_nNHC(O)(CH_2)_m$—, and —$(CH_2)_nC(O)NH(CH_2)_m$—.

In embodiments, each $R^a$, $R^{10}$, $R^{13}$, $R^{21}$, and $R^{22}$ is independently —H, —$(CH_2CH_2O)_nCH_3$, —$(CH_2CH_2O)_n(CH_2)_mCH_3$, —$(CH_2CH_2O)_n(CH_2)_mOH$, —$((CH_2)_nO)_m((CH_2)_pO)_q(CH_2)_rOH$, —$(CH_2CH_2O)_nH$, —$(CH_2)_nOH$, —$(CH_2)_nO(CH_2)_mOH$, —$(CH_2CH_2OCH_2CH_2)_nOH$, —$(CH_2CH_2O)_nCH_2CH_2OH$, —$(CH_2CH_2OCH_2CH_2)_nOH$, —$((CH_2)_{1-8}C(O)O)_n(CH2)_mOH$, —$((CH_2)_{1-8}C(O)O)_n(CH_2CH_2O)_m(OC(O)(CH_2)_{1-8})_pOH$, —$((CH_2)_{1-8}C(O)O)_n(CH_2CH_2)_m(OC(O)(CH_2)_{1-8})_pOH$, —$(CH_2C(O)O)_n(CH_2CH_2)_m(OC(O)CH_2)_pOH$, —$(CH(CH_3)C(O)O)_n(CH_2CH_2)_m(OC(O)CH(CH_3))_pOH$, —$(CH(CH_3)C(O)O)_n(CH_2CH_2)_m(OC(O)CH(CH_3))_pOH$, —$((CH_2)_nOC(O)O)(CH_2CH_2)_mOH$, —$(CH_2)_nNHC(O)(CH_2)_mOH$, —$(CH_2)_nC(O)NH(CH_2)_mOH$, $C_{1-n}$ alkyl, $C_{1-n}$ alkenyl, $C_{1-n}$ alkynyl, or $C_{6-10}$ aryl, wherein any one or more H atoms of $R^a$, $R^{10}$, $R^{13}$, $R^{21}$, or $R^{22}$ can optionally be replaced with an F atom.

In embodiments, each n, m, p, q, and r is independently 1 to 10,000, 1 to 5000, 1 to 2500, 1 to 1000, 1 to 500, 1 to 100, or 1 to 10, for example, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 1250, 1500, 1750, 2000, 2500, 3000, 3500, 4000, 4500, 5000, 6000, 7000, 8000, 9000, or 10,000.

In embodiments, the polymer backbone includes two or more zwitterionic precursor monomeric units, each of the zwitterionic monomeric units being independently selected from Formulas (A1), (B1), (C1), (D1), and (E1) and is different than the second monomeric units. For example, a polymer can include a zwitterionic precursor monomeric unit having a structure of Formula (A1) and a zwitterionic precursor monomeric unit having a structure of (B1). The same polymer can also include one or more additional zwitterionic precursor monomeric unit selected from any one of Formula (A1), (B1), (C1), (D1), and (E1). Alternatively, or additionally, a polymer can include two or more zwitterionic precursor monomeric units wherein at least two of the zwitterionic precursor monomeric units have a structure of Formula (A1), for example, but include a different selection of X, $R^1$, $R^2$, $R^3$, and $R^4$ substituents.

In embodiments, the zwitterionic precursor monomeric unit has a structure:

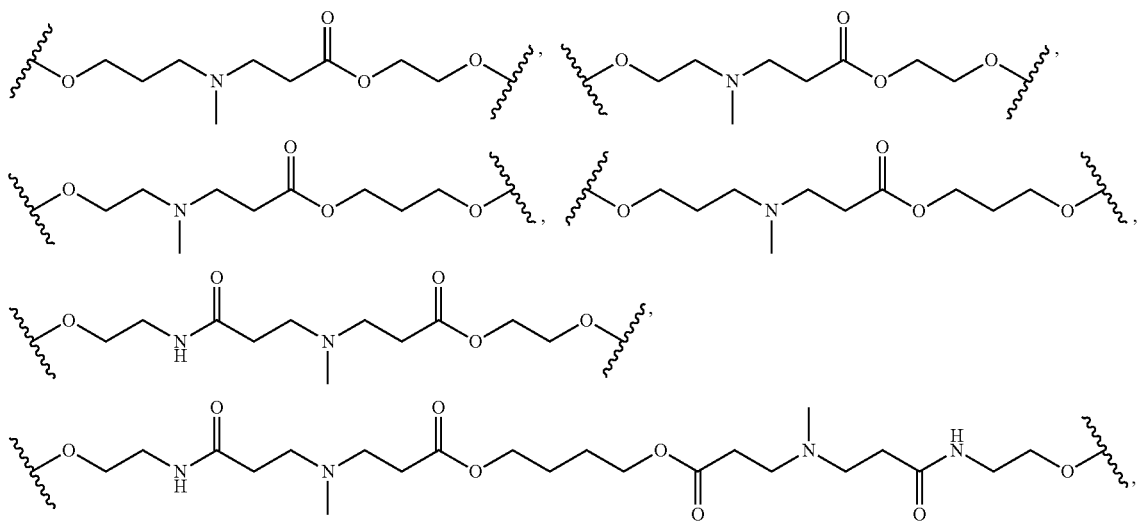

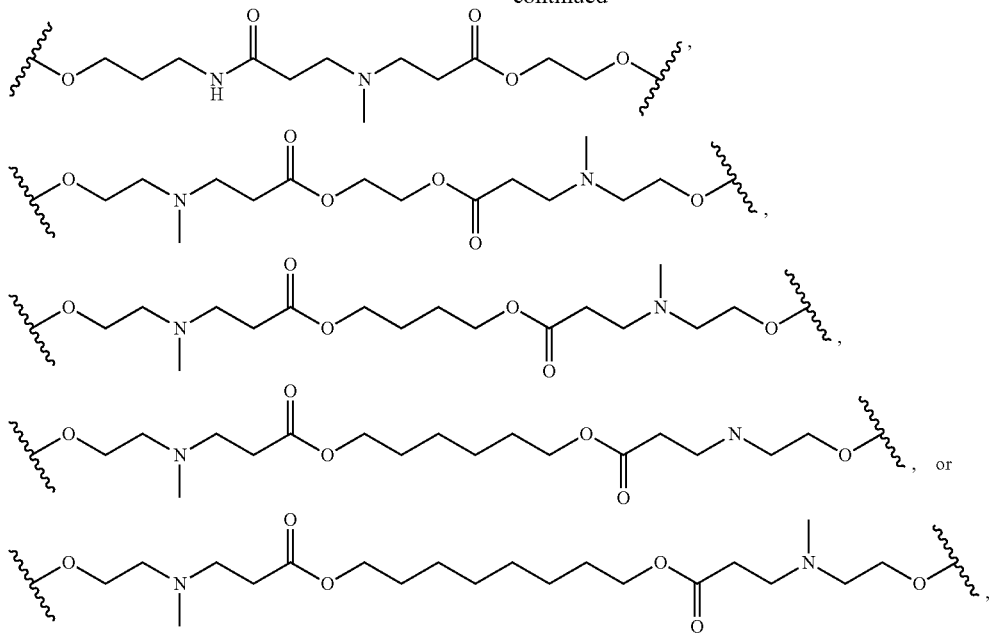
In some cases, the zwitterionic precursor monomeric unit can include crosslinking within a particular monomeric unit and/or between one zwitterionic monomeric unit and other monomeric units of the polymer. For example, in some cases, the zwitterionic precursor monomeric unit has a structure:
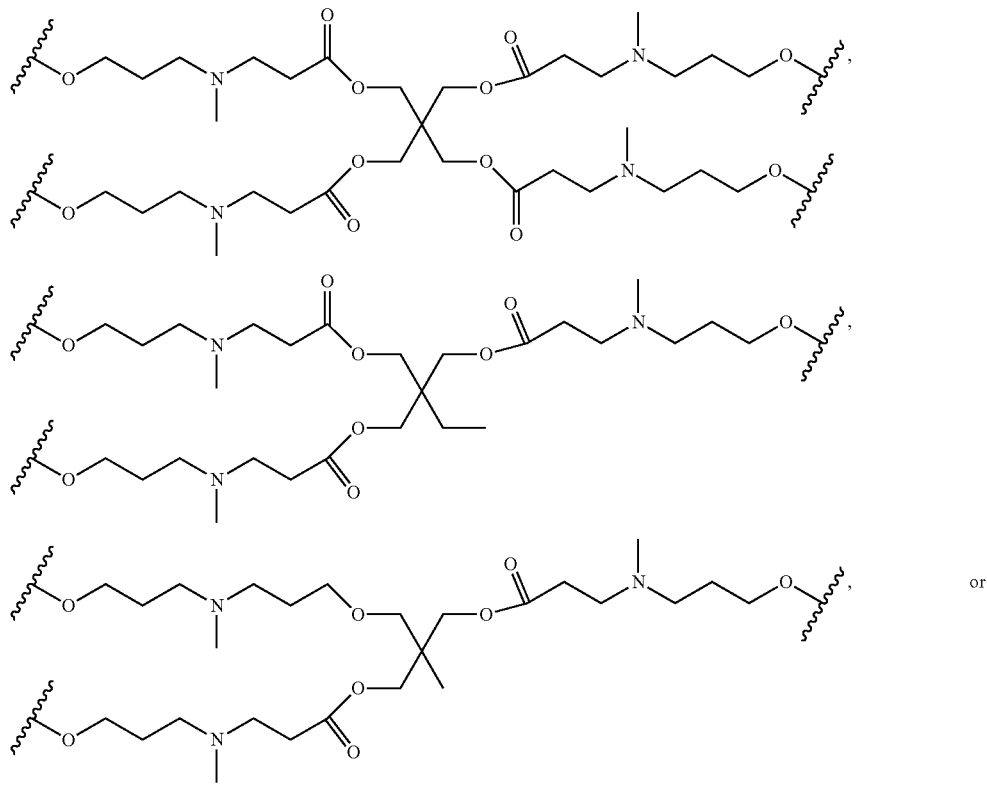

-continued

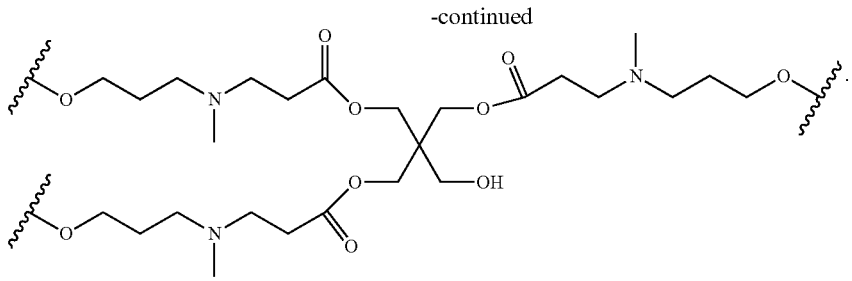

In some cases, the zwitterionic monomeric unit includes a structure of:

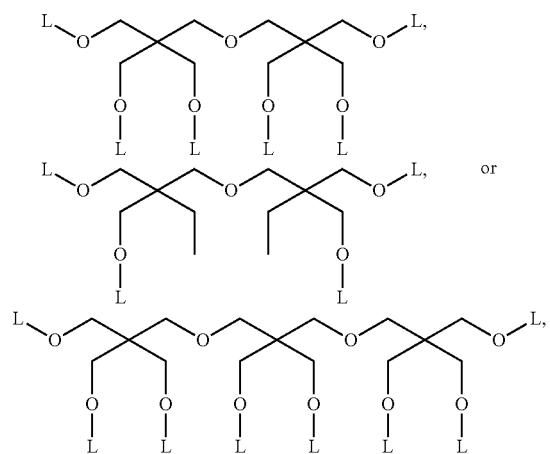

or wherein each L has a structure:

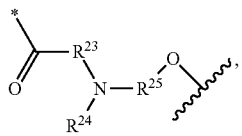

each of $R^{23}$ and $R^{25}$ is independently —$(CH_2)_n$—, —$(CH_2)_nO(CH_2)_m$—, —$(CH_2CH_2OCH_2CH_2)_n$—, —$(CH_2CH_2O)_nCH_2CH_2$—, —$((CH_2)_{1-8}C(O)O)_n(CH_2)_m$—, —$((CH_2)_{1-8}C(O)O)_n(CH_2CH_2)_m(OC(O)(CH_2)_{1-8})_p$—, —$((CH_2)_{1-8}C(O)O)_n(CH_2CH_2)_m(OC(O)(CH_2)_{1-8})_p$—, —$(CH_2C(O)O)_n(CH_2CH_2)_m(OC(O)CH_2)_p$—, —$(CH(CH_3)C(O)O)_n(CH_2CH_2)_m(OC(O)CH(CH_3))_p$—, —$(CH(CH_3)C(O)O)_n(CH_2CH_2)_m(OC(O)CH(CH_3))_p$—, —$((CH_2)_nOC(O)O)(CH_2CH_2)_m$—, —$(CH_2)_nNHC(O)(CH_2)_m$—, or —$(CH_2)_nC(O)NH(CH_2)_m$—; and $R^{24}$ is —H, —$(CH_2CH_2O)_nCH_3$, —$(CH_2CH_2O)_n(CH_2)_mCH_3$, —$(CH_2CH_2O)_n(CH_2)_mOH$, —$((CH_2)_nO)_m((CH_2)_pO)_q(CH_2)_rOH$, —$(CH_2CH_2O)_nH$, —$(CH_2)_nOH$, —$(CH_2)_nO(CH_2)_mOH$, —$(CH_2CH_2OCH_2CH_2)_nOH$, —$(CH_2CH_2O)_nCH_2CH_2OH$, —$(CH_2CH_2OCH_2CH_2)_nOH$, —$((CH_2)_{1-8}C(O)O)_n(CH2)_mOH$, —$((CH_2)_{1-8}C(O)O)_n(CH_2CH_2O)_m(OC(O)(CH_2)_{1-8})_pOH$, —$((CH_2)_{1-8}C(O)O)_n(CH_2CH_2)_m(OC(O)(CH_2)_{1-8})_pOH$, —$(CH_2C(O)O)_n(CH_2CH_2)_m(OC(O)CH_2)_pOH$, —$(CH(CH_3)C(O)O)_n(CH_2CH_2)_m(OC(O)CH(CH_3))_pOH$, —$(CH(CH_3)C(O)O)_n(CH_2CH_2)_m(OC(O)CH(CH_3))_pOH$, —$((CH_2)_nOC(O)O)(CH_2CH_2)_mOH$, —$(CH_2)_nNHC(O)(CH_2)_mOH$, —$(CH_2)_nC(O)NH$ $(CH_2)_mOH$, $C_{1-n}$ alkyl, $C_{1-n}$ alkenyl, $C_{1-n}$ alkynyl, or $C_{6-10}$ aryl, wherein any one or more H atoms of $R^{24}$ can optionally be replaced with an F atom; and each n, m, p, q, and r is independently 1 to 10,000.

For example, in embodiments, the zwitterionic monomeric unit includes a structure of

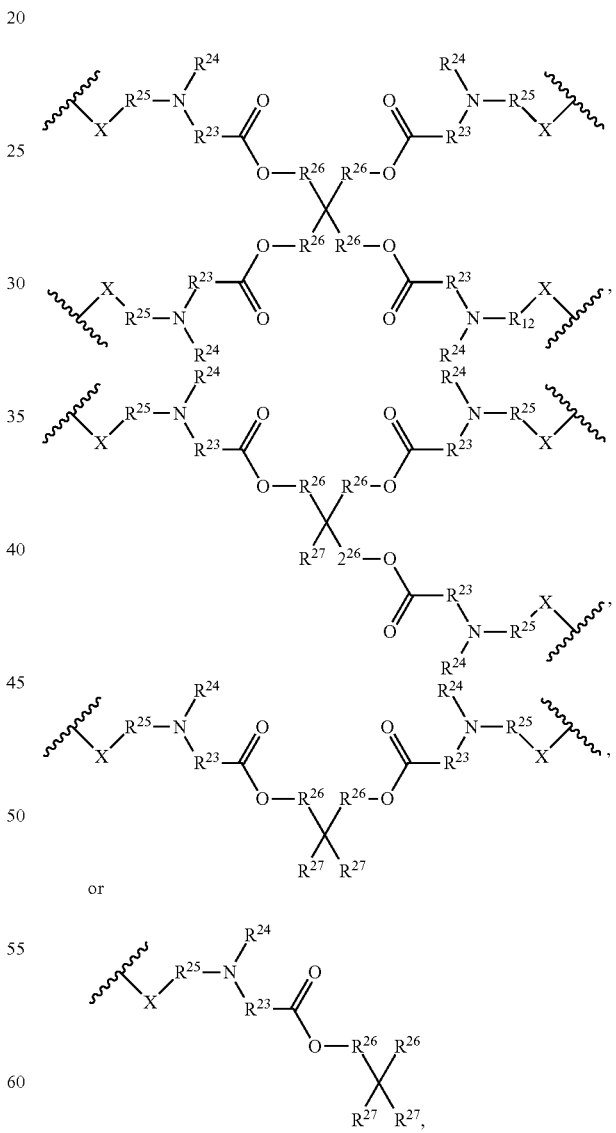

wherein each of X, $R^{23}$, $R^{24}$, and $R^{25}$ are provided as described above, each $R^{26}$ is independently —$(CH_2)_n$—, —$(CH_2)_nO(CH_2)_m$—, —$(CH_2CH_2OCH_2CH_2)_n$—, —$(CH_2CH_2O)_nCH_2CH_2$—, —$((CH_2)_{1-8}C(O)O)_n(CH_2)_m$—, —((CH$_2$)$_{1-8}$C(O)O)$_n$(CH$_2$CH$_2$O)$_m$(OC(O)(CH$_2$)$_{1-8}$)$_p$—,
—((CH$_2$)$_{1-8}$C(O)O)$_n$(CH$_2$CH$_2$)$_m$(OC(O)(CH$_2$)$_{1-8}$)$_p$—,
—(CH$_2$C(O)O)$_n$(CH$_2$CH$_2$)$_m$(OC(O)CH(CH$_3$))$_p$—, —(CH(CH$_3$)C(O)O)$_n$(CH$_2$CH$_2$)$_m$(OC(O)CH(CH$_3$))$_p$—, —((CH$_2$)$_n$OC(O)O)(CH$_2$CH$_2$)$_m$—, —(CH$_2$)$_n$NHC(O)(CH$_2$)$_m$—, or —(CH$_2$)$_n$C(O)NH(CH$_2$)$_m$—; and each R$^{27}$ is —H, —(CH$_2$CH$_2$O)$_n$CH$_3$, —(CH$_2$CH$_2$O)$_n$(CH$_2$)$_m$CH$_3$, —(CH$_2$CH$_2$O)$_n$(CH$_2$)$_m$OH, —((CH$_2$)$_n$O)$_m$((CH$_2$)$_p$O)$_q$(CH$_2$)$_r$OH, —(CH$_2$CH$_2$O)$_n$H, —(CH$_2$)$_n$OH, —(CH$_2$)$_n$O(CH$_2$)$_m$OH, —(CH$_2$CH$_2$OCH$_2$CH$_2$)$_n$OH, —(CH$_2$CH$_2$O)$_n$CH$_2$CH$_2$OH, —(CH$_2$CH$_2$OCH$_2$CH$_2$)$_n$OH, —((CH$_2$)$_{1-8}$C(O)O)$_n$(CH2)$_m$OH, —(CH$_2$)$_{1-8}$C(O)O)$_n$(CH$_2$CH$_2$O)$_m$(OC(O)(CH$_2$)$_{1-8}$)$_p$OH, —((CH$_2$)$_{1-8}$C(O)O)$_n$(CH$_2$CH$_2$)$_m$(OC(O)(CH$_2$)$_{1-8}$)$_p$OH, —(CH$_2$C(O)O)$_n$(CH$_2$CH$_2$)$_m$(OC(O)CH$_2$)$_p$OH, —(CH(CH$_3$)C(O)O)$_n$(CH$_2$CH$_2$)$_m$(OC(O)CH(CH$_3$))$_p$OH, —(CH(CH$_3$)C(O)O)$_n$(CH$_2$CH$_2$)$_m$(OC(O)CH(CH$_3$))$_p$OH, —((CH$_2$)$_n$OC(O)O)(CH$_2$CH$_2$)$_m$OH, —(CH$_2$)$_n$NHC(O)(CH$_2$)$_m$OH, —(CH$_2$)$_n$C(O)NH(CH$_2$)$_m$OH, C$_{1-n}$ alkyl, C$_{1-n}$ alkenyl, C$_{1-n}$ alkynyl, or C$_{6-10}$ aryl, wherein any one or more H atoms of R$^{27}$ can optionally be replaced with an F atom; and each n, m, p, q, and r is independently 1 to 10,000.

Additional Monomeric Units

Any of the polymers described herein can be further polymerized with one or more additional monomers and/or polymers to provide copolymers and/or hybrid polymers.

As described above, in embodiments, the polymer backbone further includes one or more additional monomeric units. In some cases, the one or more additional monomeric units are independently selected from Formulas (A1), (B1), (C1), (D1), and (E1), and are different than the second monomeric unit.

In embodiments, the polymer backbone further includes a third monomeric unit derived from one or more of a urethane, urea, amide, ester, imide, and carbonate. That is, the polymer of the disclosure can be copolymerized with any other suitable monomer to provide a copolymer or hybrid polymer. For example, in some cases, the polymer of the disclosure can be copolymerized with an ester monomer and/or a polyester polymer, to provide a copolymer including a first monomeric unit and second monomeric unit, as provided herein, and one or more additional monomeric units derived from the ester or polyester.

In embodiments, the polymer can include a polyurethane. As used herein, "polyurethane" means a polymer composed of, or inclusive of, organic units joined by carbamate (—OC(O)NH—) links.

In some cases, the first monomeric can include an isocyanate, the second monomeric unit can include the zwitterionic precursor monomeric unit, and a third monomeric can include a diol or polyol. In some cases, the first monomeric can include an isocyanate, the second monomeric unit can include the zwitterionic precursor monomeric unit, and a third monomeric can include a diamine or polyamine.

Implantable Medical Devices

Provided herein are implantable medical devices including the polymer of the disclosure. The polymer can be used to provide an entire medical device, a portion thereof, or a surface or coating thereof. The polymer can be applied (e.g., coated, covalently coupled, ionically associated, hydrophobically associated) to one or more surfaces of a medical device.

Representative devices that may be advantageously prepared by or treated with a polymer of the disclosure include, but are not limited to: particles (e.g., nanoparticles) having a surface treated with, modified to include, or incorporates a polymer of the disclosure; drug carriers having a surface treated with, modified to include, or incorporates a polymer of the disclosure; non-viral gene delivery systems having a surface treated with, modified to include, or incorporates a polymer of the disclosure; biosensors having a surface treated with, modified to include, or incorporates a polymer of the disclosure; devices for bioprocesses or bioseparations, such as membranes for microbial suspension, hormone separation, protein fractionation, cell separation, waste water treatment, oligosaccharide bioreactors, protein ultrafiltration, and diary processing having a surface treated with, modified to include, or incorporates a polymer of the disclosure; implantable sensors having a surface treated with, modified to include, or incorporates a polymer of the disclosure; subcutaneous sensors having a surface treated with, modified to include, or incorporates a polymer of the disclosure; implant, such as a breast implant, cochlear implant, and dental implant having a surface treated with, modified to include, or incorporates a polymer of the disclosure; contact lenses having a surface treated with, modified to include, or incorporates a polymer of the disclosure; tissue scaffolds having a surface treated with, modified to include, or incorporates a polymer of the disclosure; implantable medical devices, such as an artificial joint, artificial heart valve, artificial blood vessel, pacemaker, left ventricular assist device (LVAD), artery graft, and stent having a surface treated with, modified to include, or incorporates a polymer of the disclosure; and medical devices, such as an ear drainage tube, feeding tube, glaucoma drainage tube, hydrocephalous shunt, keratoprosthesis, nerve guidance tube, urinary catheter, tissue adhesive, and x-ray guide having a surface treated with, modified to include, or incorporates a polymer of the disclosure.

Methods of Making

Provided herein are methods of preparing the polymers of the disclosure.

In embodiments, the methods include admixing first monomeric unit precursors to form a prepolymer solution; admixing the prepolymer solution with one or more second monomeric unit precursors that includes one or more zwitterionic precursor compounds to form a modified prepolymer solution. In embodiments, the zwitterionic precursor compounds include a secondary or tertiary amine. The method further includes, in embodiments, exposing the modified prepolymer solution to conditions sufficient to initiate polymerization, thereby forming a polymer having a polymer backbone, wherein at least one functional group of the zwitterionic precursor compound is incorporated into the polymer backbone. In embodiments, the zwitterionic precursor compound includes a secondary or tertiary amine and the secondary or tertiary amine is incorporated into the polymer backbone upon polymerization.

In embodiments, the method includes admixing a diol, polyol, diamine, or polyamine with an isocyanate to form a prepolymer solution; admixing the prepolymer solution with a zwitterionic precursor compound having a secondary or tertiary amine to form a modified prepolymer solution; and, exposing the modified prepolymer solution to conditions sufficient to initiate polymerization, thereby forming a polymer having a polymer backbone, wherein the secondary or tertiary amine of the zwitterionic precursor compound is within the polymer backbone.

In embodiments, the method includes admixing one or more secondary monomeric units having one or more zwitterionic precursor compounds with a first monomeric unit precursor compound to form a prepolymer solution; admixing the prepolymer solution with a second first monomeric unit precursor compound to form a modified prepolymer solution; and exposing the modified prepolymer solution to conditions sufficient to initiate polymerization, thereby forming a polymer having a polymer backbone with at least one functional group from the zwitterionic precursor compound incorporated into the backbone. In embodiments, the zwitterionic precursor compound includes a secondary or tertiary amine and the secondary or tertiary amine is incorporated into the polymer backbone upon polymerization.

In embodiments, the method includes admixing a zwitterionic precursor compound having a secondary or tertiary amine with an isocyanate to form a prepolymer solution admixing the prepolymer solution with a diol, polyol, diamine, or polyamine to form a modified prepolymer solution; and, exposing the modified prepolymer solution to conditions sufficient to initiate polymerization, thereby forming a polymer having a polymer backbone, wherein the secondary or tertiary amine of the zwitterionic precursor compound is within the polymer backbone.

In embodiments, the method includes admixing one or more secondary monomeric units comprising one or more zwitterionic precursor compounds with one or more first monomeric precursor compounds to form a prepolymer solution and exposing the prepolymer solution to conditions sufficient to initiate polymerization, thereby forming a polymer having a polymer backbone with at least one functional group of the zwitterionic precursor compound incorporated into the polymer backbone.

In embodiments, the method includes admixing a zwitterionic precursor compound having a secondary or tertiary amine with an isocyanate and a diol, polyol, diamine, or polyamine to form a prepolymer solution; exposing the prepolymer solution to conditions sufficient to initiate polymerization, thereby forming a polymer having a polymer backbone, wherein the secondary or tertiary amine of the zwitterionic precursor compound is within the polymer backbone.

The isocyanate can be selected as described in detail, above. That is, in embodiments, the isocyanate can include, but is not limited to, a diisocyanate and/or a polyisocyanate. In embodiments, the isocyanate includes isocyanate, isocyanate PEG, 4,4-methylenebis(phenyl isocyanate), 4,4-methylenebis(cyclohexyl isocyanate), 4,4'-oxybis(phenyl isocyanate), 3arm-PEG-isocyanate, 4arm-PEG-isocyanate, bis(4-isocyanatophenyl)methane, 4,4'-methylenebis(2-chlorophenyl isocyanate), 3,3'-dichloro-4,4'-diisocyanato-1,1'-biphenyl, hexamethylene diisocyanate (HDI), 1,4-phenylene diisocyanate, 1,3-phenylene diisocyanate, m-xylylene diisocyanate, tolylene-2,4-diisocyanate, tolylene-2,6-diisocyanate, poly(hexamethylene diisocyanate), trans-1,4-cyclohexylene diisocyanate, 4-chloro-6-methyl-1,3-phenylene diisocyanate, 1,4-diisocyanatobutane, 1,8-diisocyanatooctane, 1,3-bis(1-isocyanato-I-methylethyl)benzene, 3,3'-dimethyl-4,4'-biphenylene diisocyanate, 1,12-diisocyanatododecane, polyisocyanate, or any combination thereof. In some cases, the isocyanate includes hexamethylene diisocyanate (HDI).

The diol or polyol can be selected as described in detail, above. That is, in embodiments, the diol or polyol includes, but is not limited to, poly(ethylene glycol) (PEG), ethylene glycol, diethylene glycol, triethylene glycol, tetraethylene glycol, propylene glycol, dipropylene glycol, tripropylene glycol, 1,3-propanediol, 1,3-butanediol, 1,4-butanediol, neopentyl glycol, 1,6-hexanediol, 1,4-cyclohexanedimethanol, trimethylolpropane, 1,2,6-hexanetriol, triethanolamine, pentaerythritol, glycerol, N,N,N',N'-tetrakis (2-hydroxypropyl)ethylenediamine, polytetrahydrofuran (PTHF) diol, polytetrahydrofuran (PTHF) triol, polycaprolactone (PCL) diol, polycaprolactone (PCL) triol, polycaprolactone (PCL) polyol, polydimethylsiloxane (PDMS) diol, polydimethylsiloxane (PDMS) triol, polydimethylsiloxane (PDMS) polyol, polyester diol, polyester triol, polylactide (PLA) diol, polylactide (PLA) triol, polypeptides, polyester, polyether, polyamide, octanediol, fluoroalkane polyol, fluoroalkene polyol, fluoroalkyne polyol, alkane polyol, alkene polyol, alkyne polyol, aromatic polyol, poly(vinyl alcohol), polysaccharide, poly(2-hydroxyethyl methacrylate) (pHEMA), poly(2-hydroxyethyl acrylate), poly(N—Hydroxyethyl acrylamide), poly(N-(Hydroxymethyl)acrylamide), poly(N-tris(hydroxymethyl)methacrylamide), poly((methyl)acrylate) polyol, poly((methyl)acrylamide) polyol, poly(polytetrahydrofuran carbonate) diol, polycarbonate diol, polycarbonate polyol, or any combination thereof.

In embodiments, the diol or polyol includes PEG, and the isocyanate includes HDI. In embodiments, the diol or polyol include glycerol, and the isocyanate includes HDI.

The diamine or polyamine can be selected as described in detail, above. That is, in embodiments, the diamine or polyamine can include, but is not limited to, methanediamine, ethylenediamine, 1,1-dimethylethylenediamine, 1,2-dimethylethylenediamine, ethambutol, TMEDA, 1,3-diaminopropane, putrescine, cadaverine, hexamethylenediamine, trimethylhexamethylenediamine, 1,2-diaminopropane, diphenylethylenediamine, trans-1,2,diaminocyclohexane, 1,4-diazacyclohexane, o-phenylenediamine, m-phenylenediamine, p-phenylenediamine, 2,5-diaminotoluene, dimethyl-4-phenylenediamine, N,N'-di-2-butyl-1,4-phenylenediamine, 4,4'-diaminobiphenyl, 1,8-diaminonapthalene, diethylenetriamine, pentamethyldiethylenetriamine, triethylenetetramine, tetraethylenepentamine, pentaethylenehexamine, 1,4,7-triazacyclonane, tris(2-aminoethyl)amine, polyethylene amine, or 1,1,1-tris(aminomethyl)ethane.

In embodiments, the diol or polyol, the isocyanate, and the zwitterionic precursor compound are provided in amounts sufficient to provide a polymer having a ratio of hydroxyl groups in the zwitterionic precursor monomeric unit:hydroxyl groups in the diol or polyol:isocyanate groups in the isocyanate ranging from about 1:9999:10,000 to about 10,000:0:10,000, or about 1:999:1000 to about 1000:0:1000 for example, 2:8:10, 4:6:10, 6:4:10, 8:2:10, or 10:0:10, 100:0:100, 75:25:100, 50:50:100, 25:75:100, or 0:100:100. In some cases, the compounds are provided in amounts sufficient to provide a ratio selected from 2:8:10, 4:6:10, 6:4:10, 8:2:10, or 10:0:10.

In embodiments, the zwitterionic precursor compound has a structure according to Formula (A2) or (B2):

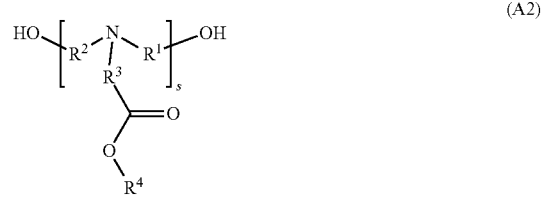

(A2)

-continued
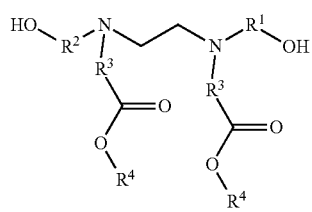
(B2)
wherein each of $R^1$, $R^2$, $R^3$, $R^4$, and s can be independently selected as described, above.
In embodiments, the zwitterionic precursor compound is selected from:
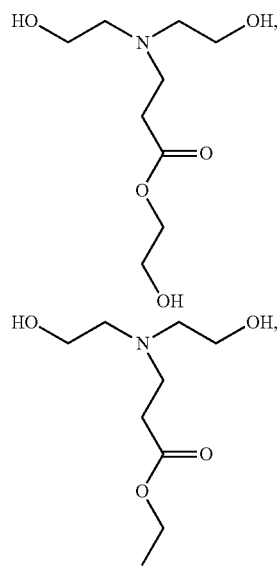
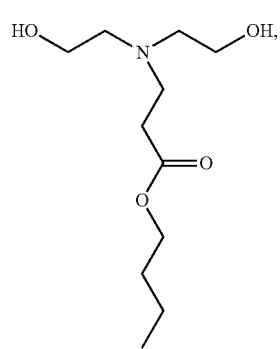
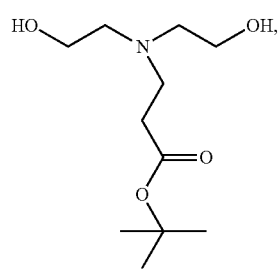
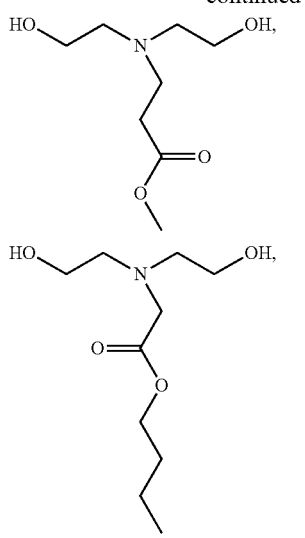
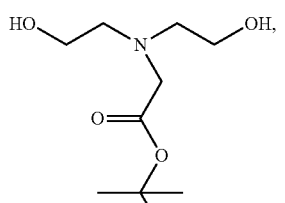
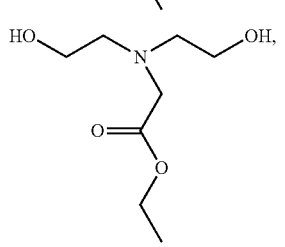
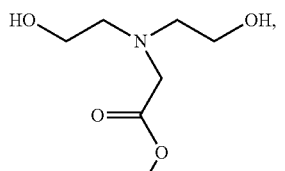
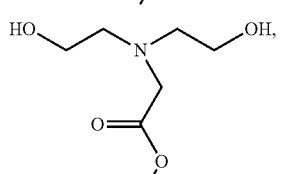
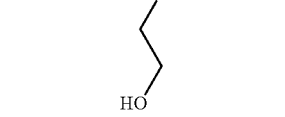
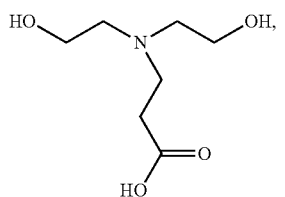

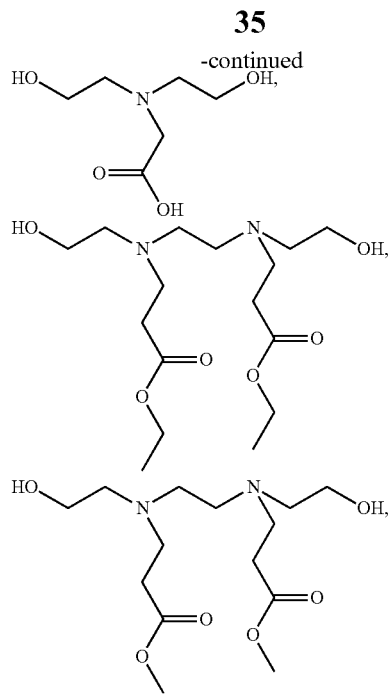
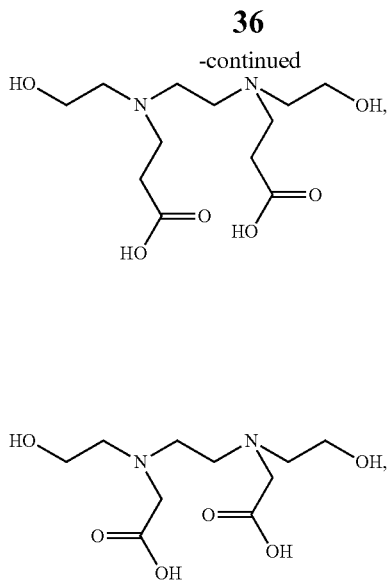
or any combination thereof.
In embodiments, the zwitterionic precursor compound has a structure according to Formula (B2), (C2), or (D2):
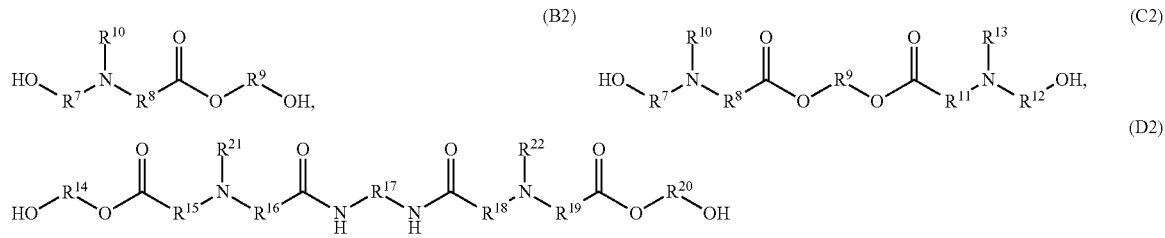
wherein each of $R^7$, $R^8$, $R^9$, $R^{11}$, $R^{12}$, $R^{14}$, $R^{15}$, $R^{16}$, $R^{17}$, $R^{18}$, $R^{19}$, $R^{20}$, $R^{10}$, $R^{13}$, $R^{21}$, and $R^{22}$ can be independently selected, as described above.
In embodiments, the zwitterionic precursor compound has a structure:
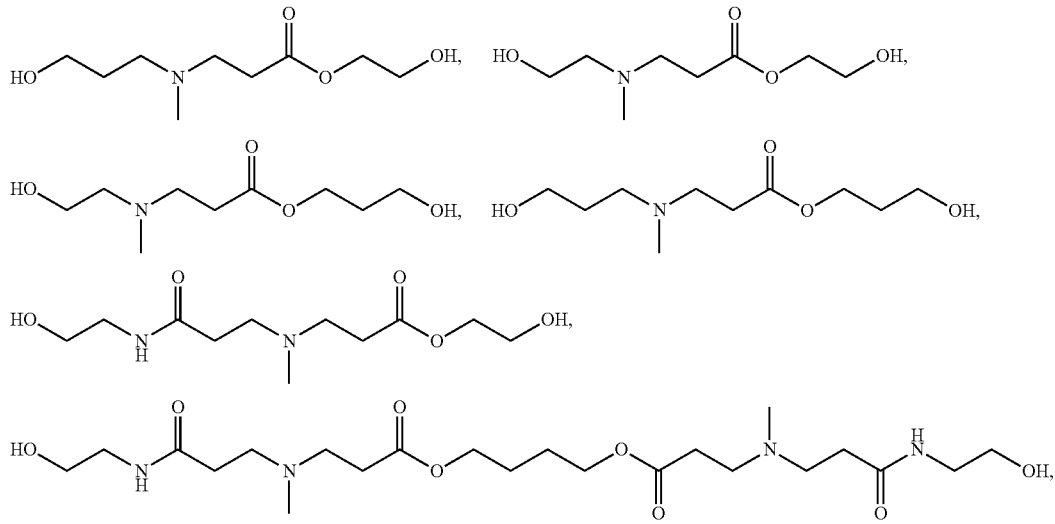

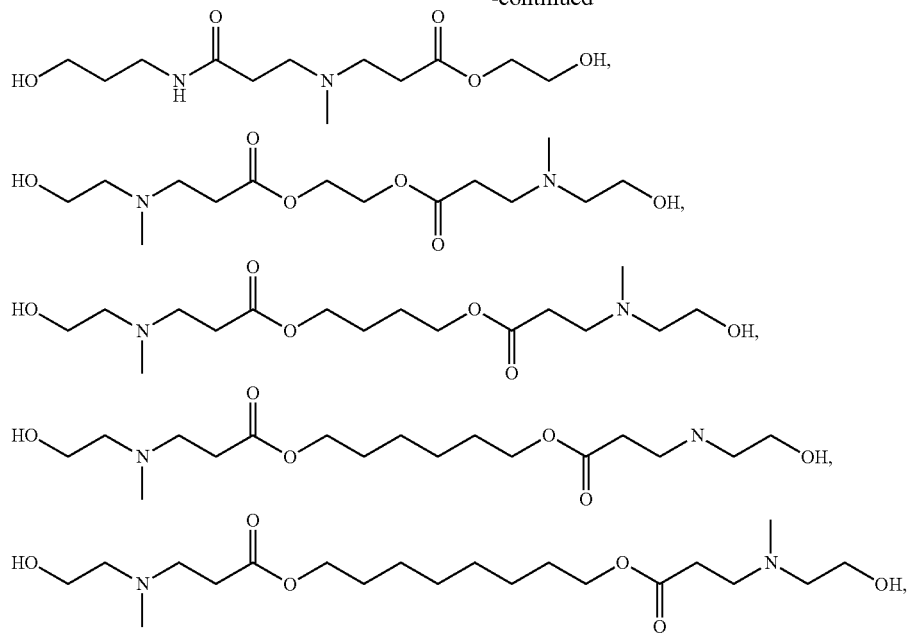
or any combination thereof.
In some cases, the zwitterionic precursor compound can include crosslinking within a particular compound. For example, in some cases, the zwitterionic precursor compound has a structure:
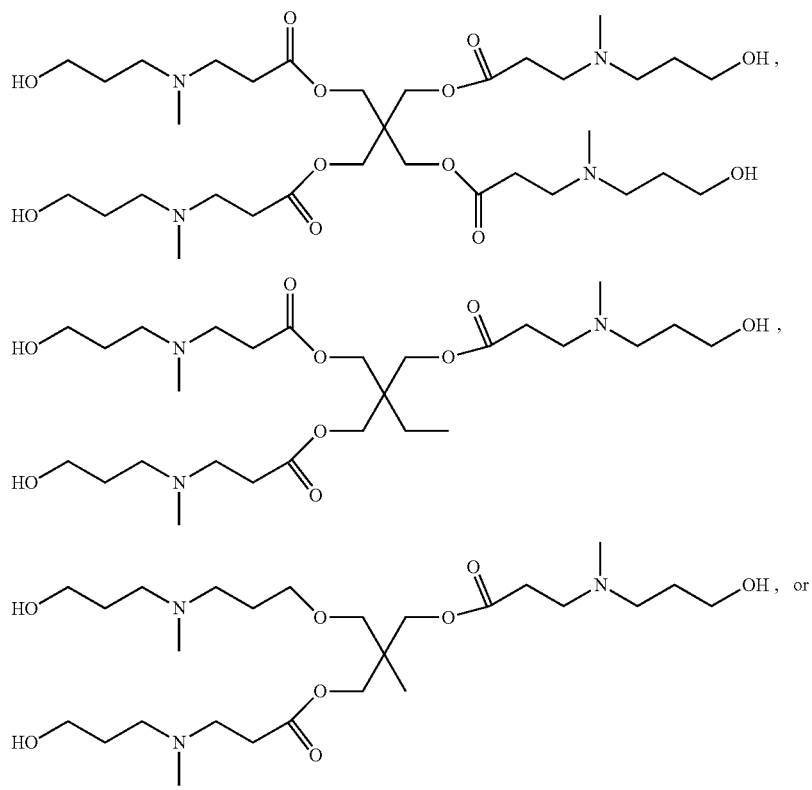

-continued

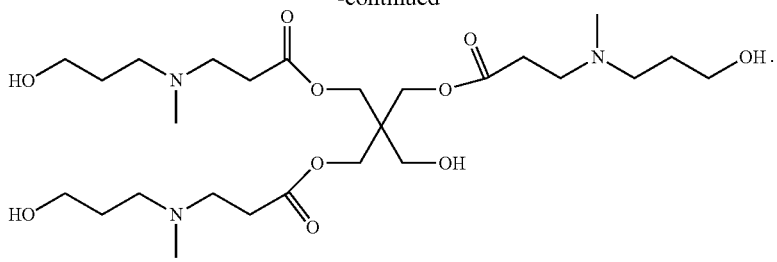

In embodiments, each admixing step can occur at a temperature ranging from about 50° C. to about 100° C., about 60° C. to about 90° C., or about 70° C. to about 80° C., for example about 50, 55, 60, 65, 70, 75, 80, 85, 90, 95 or 100° C.

In some embodiments, the prepolymer solution and/or the modified prepolymer solution is substantially free of organic solvent. As used herein, the term "substantially free" means that the prepolymer and/or the modified prepolymer solution suitably contains less than 5%, 4%, 3%, 2%, 1%, 0.5%, 0.1%, or 0.01% of organic solvent, and/or up to about 0.01%, 0.1%, 0.5%, 1%, 2%, 2%, 4%, or 5% organic solvent.

In some embodiments, the prepolymer solution and/or the modified prepolymer solution includes an organic solvent. Suitable organic solvents include but are not limited to DMF, DMSO, DCM, chloroform, THF, and/or any combination thereof.

In embodiments wherein two admixing steps occur, both admixing steps can occur in the same reaction vessel.

The exposing step can occur at a temperature ranging from about 20° C. to about 200° C., about 50° C. to about 150° C., or about 75° C. to about 100° C., for example about 20, 30, 40, 50, 60, 70, 80, 90, 100, 110, 120, 130, 140, 150, 160, 170, 180, 190, or 200° C.

In embodiments, the exposing step can occur in the presence of a tertiary amine initiator. One example of a suitable tertiary amine initiator is 1,4-diazabicyclo[2.2.2]octane (DABCO).

In embodiments, the exposing step can occur in the presence of a metallic compound. Examples of suitable metallic compounds include, but are not limited to, dibutyltin dilaurate or bismuth octanoate.

In embodiments, the exposing step can occur in the presence of ultraviolet (UV) light.

The methods described herein can further include hydrolyzing the polymer in an aqueous solution. In embodiments, the aqueous solution includes deionized water. In embodiments, the hydrolyzing occurs at a temperature ranging from about 4° C. to about 99° C., about 5° C. to about 95° C., about 15° C. to about 75° C., about 40° C. to about 60° C., or about 45° C. to about 55° C., for example about 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, or 99° C.

In embodiments, the hydrolyzing can occur at a pH value ranging from about 6 to about 14, about 7 to about 12, or about 9 to about 11, for example about 6, 6.5, 7, 7.5, 8, 8.5, 9, 9.5, 10, 10.5, 11, 11.5, 12, 12.5, 13, 13.5, or 14.

In embodiments, the aqueous solution is substantially free of added base. As used herein, the term "substantially free of added base" means that the aqueous solution suitably contains less than 5%, 4%, 3%, 2%, 1%, 0.5%, 0.1%, or 0.01% of added, and/or up to 0.01%, 0.1%, 0.5%, 1%, 2%, 2%, 4%, or 5% added base. In some cases, the aqueous solution is substantially free of NaOH and/or KOH. Advantageously, hydrolysis of the polymers disclosed herein does not require the use of a strong base, such as NaOH.

In some embodiments, the aqueous solution includes an inorganic or tertiary amine organic base. Bases can optionally be added to the aqueous solution in order to increase the rate of hydrolysis of the polymer.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compounds, compositions, articles, methods, and processes are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure, and following examples.

EXAMPLES

Materials

Diethanolamine, 2-hydroxyethyl acrylate, ethyl acrylate and fluorescein isothiocyanate isomer 1 were purchase from Alfa Aeser (Haverhill, MA). Polyethylene glycol (PEG) 2000, glycerol, bovine serum albumin (BSA) was purchase from Sigma Aldrich (St. Louis, MO, USA). 1,6-Diisocyanatohexane (HDI) was purchased from Acros Organics (Pittsburgh, PA, USA). Dimethylformamide (DMF) was purchased from EMD Millipore (Burlington, MA, USA). Viability/cytotoxicity assay kit for bacteria live and dead cells was purchased from Biotium (Fremont, CA, USA). Commercial biomedical polyurethane materials were obtained from API company. (Mussolente, VI, Italy).

Instrumentation and Methods
Fourier Transform Infrared Spectroscopy (FTIR)

Fourier transform infrared spectroscopy (FTIR) analysis was recorded on a Nexus 870 spectrometer (Thermo Nicolet, USA) with an attenuated total reflection (ATR) mode. The wavenumber ranges from 400 to 4000 cm$^{-1}$ with between 32 and 64 total scans.

Thermogravimetric Analysis (TGA)

Thermogravimetric analysis (TGA) TGA/SDTA 851e (Mettler Toledo, USA) was used to study the thermal stability of the PU materials. The temperature ranges from 50 to 700° C. with a heating rate of 10° C./min with continuous $N_2$ flow of 50 ml/min.

Differential Scanning Calorimetry (DSC)

Differential scanning calorimetry (DSC) was performed for all the PU materials to measure the phase transition temperature using thermal analyzer DSC 822e (Mettler Toledo, USA). A heating rate of 10° C./min from −40° C. to 250° C. was employed with continuous $N_2$ flow of 50 ml/min.

Hydrolysis Process Monitoring by pH Change

Each sample (8 mm in diameter and 2 mm in thickness) were immerged into DI water. The pH value was recorded every 5 min in first 30 min, every hour in the first day, and then every day for 10-15 days.

Swelling Ratio Measurement

For swelling ratio studies, PU hydrogels with different component were made 8 mm in diameter and 2 mm in height. After swelling equilibrium in ultrapure water overnight, the amounts of PU hydrogels were recorded and then placed in a freeze-dryer and lyophilized prior to being weighed again. The swelling ratio, Q, was calculated using the following equation.

$$Q=(M_S-M_D)/M_D$$

where $M_S$ is the mass after swelling, $M_D$ is the mass after lyophilizing.

Compression Testing

The Stress-Strain curves of polyurethane samples were evaluated with a Shimadzu EZ-Test Compact Bench Testing Machine (Shimadzu Corporation, Nakagyo-ku, Kyoto, Japan). Each kind of material (about 8 mm in diameter and 2 mm in thickness for both before and after hydrolysis sample) were compressed to failure at rate of 1 mm/min with a 500 N load cell.

Protein Adsorption

The adsorption of protein on PU hydrogels was determined by Enzyme-Linked Immunosorbent Assay (ELISA). After reaching equilibrium, PU hydrogels and purchased PU membrane were cut into discs with a biophysical punch (8 mm in diameter and 2 mm thick), washed thoroughly with DI water and transferred into a sterile 24-well plate. 1 mL of FITC-labelled Bovine serum albumin (BSA) (FITC-BSA) solution (0.1 mg/mL) was added into each well. All samples were immersed in the solution for 30 minutes to allow protein adsorption on hydrogel surfaces. To remove loosely adsorbed proteins on sample surfaces, hydrogel samples were rinsed with PBS three times. Protein adsorption on hydrogel surface was visualized with an Olympus IX81 fluorescent microscopy (Olympus, Japan) with 40× objective lens through FITC filter at a fixed exposure time for all samples, so the different protein adsorption will lead to different fluorescent intensity on images. ImageJ software was used to quantify the fluorescent intensity of each sample.

Cells Attachment

After hydrogels were equilibrated in water, NIH-3T3 cells were seeded on different hydrogel substrates at 10×10$^4$ cells/well with serum medium consisting of DMEM, 10% fetal bovine serum (FBS), and 1% penicillin-streptomycin and kept in an incubator with 5% $CO_2$ at 37° C. for 24 hours. Surface cell coverage and cell morphology was visualized with the same fluorescence microscope with 10× to 60× objective lens through FITC filters.

Bacterial Attachment

*Escherichia coli* K12 or *P. aerufinosa* POA1 cells were cultured at 37° C. in Luria-Bertani (LB) medium (20 g L$^{-1}$) to reach an optical density of 1.0 at 600 nm. After three washes with PBS, cells were suspended in 0.85% NaCl aqueous solution to get a final concentration of 10$^8$ cells mL$^{-1}$. 50 µL of fresh bacterial suspension in PBS was pipetted onto hydrogel discs (8 mm in diameter) and incubated at room temperature for 1 h. To analyze the density of bacteria accumulated on hydrogel surfaces, samples were gently rinsed with water, and stained with Viability/Cytotoxicity Assay for Bacteria Live & Dead Cells kit. After the staining, the number of live and dead cells was determined with an Olympus IX81 fluorescent microscopy (Olympus, Japan) with 40× objective lens through FITC filters.

Biofilm Formation Assay

*P. aerufinosa* cells from the second culture were washed three times with sterile PBS and subsequently re-suspended in sterile Luria Broth (LB) bacterial culture media at a concentration of 10$^6$ cells/ml. The sterile LB media was changed every day for the bacterial cells. The temperature of the system was maintained at 25° C. After 2 weeks, the accumulated bacteria were recorded in situ using an Olympus IX81 fluorescent microscopy (Olympus, Japan) with 20× objective lens through FITC filters.

Example 1—Synthesis and Evaluation of Zwitterionic Polymer

Overview

A series of zwitterionic poly(carboxybetaine-urethane)s (PCBHU)s were synthesized, where CB content in the polymer could be readily tuned by altering the molar ratio of soft segments and hard segments employed in the synthesis. The dual-function of both surface antifouling properties and tunable bulk properties was achieved in one polymeric biomaterial. Chemical structure, thermal stability, thermal transition, and mechanical properties of resulting polymers with different component ratios were characterized. The hydrolysis kinetics of the polyurethane in solutions with different pH values was recorded. The protein adsorption on PCBHUs was evaluated using bovine serum albumin (BSA) as a model protein via a fluorescent method. Cell, bacterial attachment, and biofilm formation on the hydrogel surface were carried out to further demonstrate the antifouling properties of zwitterionic PCBHUs.

A series of novel zwitterionic polycarboxybetaine urethanes (PCBU) with tunable mechanical swelling properties was synthesized and characterized. PCBU was synthesized via the polymerization of carboxybetaine (CB)-based triols with diisocyanate. Post-polymerization hydrolysis of the triol-segment side chain generated zwitterionic CB functional groups that facilitated the mechanical properties and surface foulant resistance via the enhanced hydration capacities surrounding the opposing charges of CB-based triol component. Thermogravimetric analysis (TGA) and Differential scanning calorimetry (DSC) profiles demonstrate the high thermal stability of PUs, which can be up to 305° C. Tunable mechanical properties and water uptakes were achieved by controlling the structural characteristics of CB-based cross-linker. Advantageously, the CB-based components can be easily incorporated into the polyurethane without a significant change of the production and processing conditions. The resulting PCBHU is extremely useful for biomedical application.

Synthesis of Diethanoamino-N—Hydroxyl Ethyl Acetate (DEAHA)

DEAHA (structure provided below) was synthesized using a Michael-type reaction.

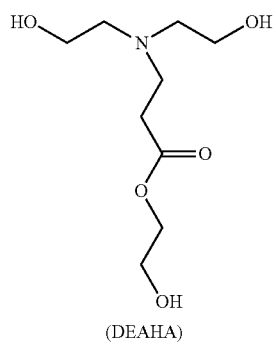 [SMILES: O=C(CCN(CCO)CCO)OCCO]

(DEAHA)

Diethanolamine (30 g, 0.28 mol) was added into 2-hydroxyethyl acrylate (36.4 g, 0.31 mol). The resulting solution was stirred overnight under 35° C., and kept away from the light during the reaction. The reaction mixture was concentrated in a rotovap and then purified by flash chromatography using a dichloromethanoe and methanol mixture (5:1) as the mobile phase to yield DEAHA. $^1$H NMR (400 MHz, CDCl$_3$, ppm): 4.03 (t, 2H), 3.59 (t, 2H), 2.67 (t, 2H), 2.35 (t, 2H), 3.42 (m, 4H), 2.44 (m, 4H).

Synthesis of Polymer

Five polymers with different stoichiometric ratios of hydroxyl groups in DEAHA/hydroxyl groups of PEG/isocyanate groups in HDI (2:8:10, 4:6:10, 6:4:10, 8:2:10, and 10:0:10) were prepared and named PCBHU-2, PCBHU-4, PCBHU-6, PCBHU-8 and PCBHU-10, respectively. A control polymer PGHU-8 with the ratios of hydroxyl groups in glycerol/hydroxyl groups of PEG/isocyanate groups in HDI (8:2:10) as a control was also synthesized. The polymers were synthesized via a one-pot reaction. The synthesis of the polymers followed the general reaction scheme, below:

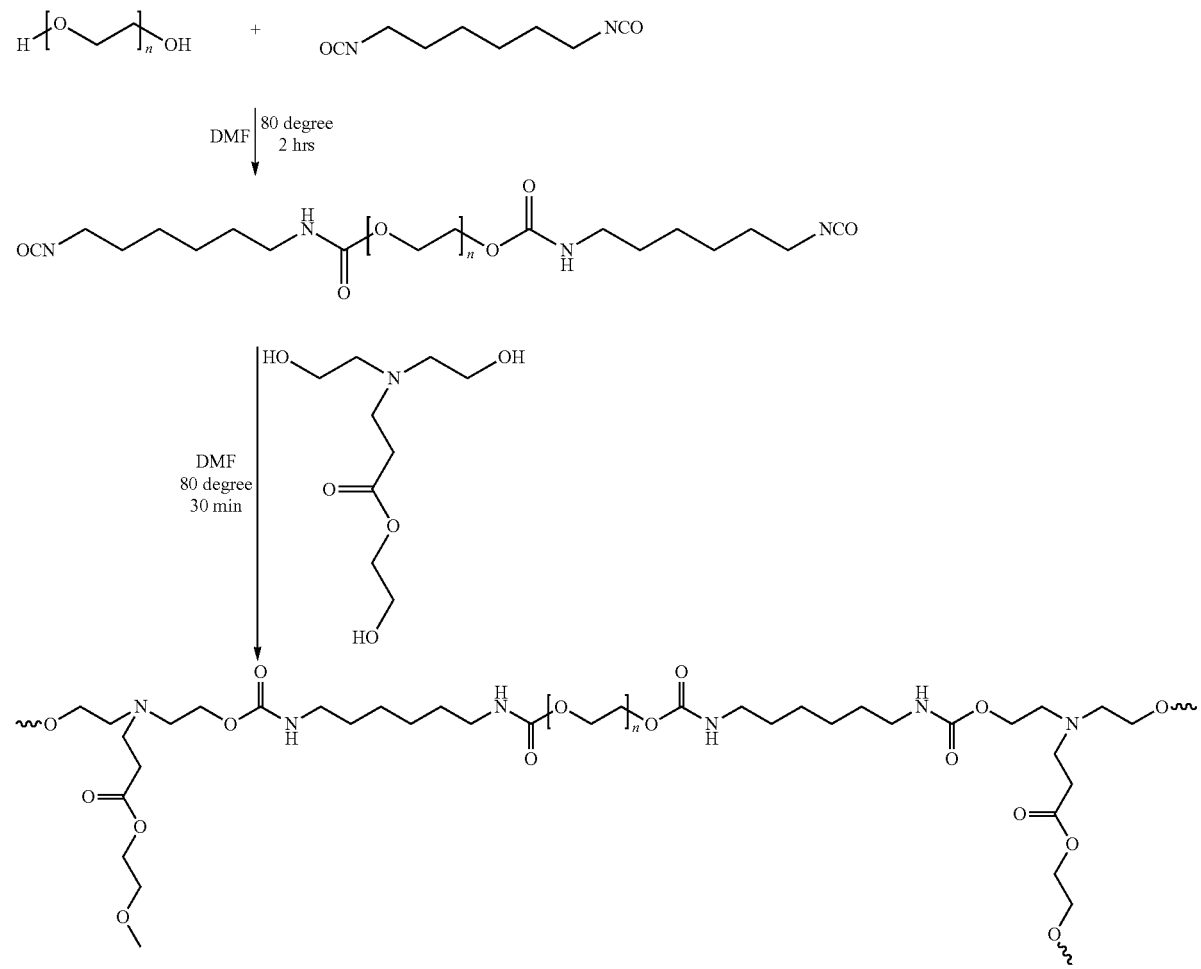

PU-prepolymer was synthesized in a three-necked round bottom flask equipped with a mechanical stirrer, a temperature controller and a nitrogen inlet. Reaction was carried out in a nitrogen atmosphere. Before the reaction, the PEG 2000 was placed into vacuum oven under 110° C. for 2 hours for removing moisture. The HDI was then added into three-necked round bottom flask dropwise. DMF was added once the viscosity increased. The prepolymer solution was stirred for 2 hours under 80° C. DEAHA as chain extender/cross-linker was added into the solution dropwise and stirred for another 30 minutes under 80° C. The prepolymer solution was then poured into poly(tetrafluoroethylene) (PTFE) dishes and placed in the oven at 100° C. for 12 hours. The resulting polyurethane was dried under 100° C. in the vacuum oven for 12 hours to remove residual solvent. After drying, the PU films were peeled off and cut into disks with a biophysical punch (8 mm in diameter, 2 mm in thickness). PU hydrogels were formed after equilibration in water for 2 weeks.

Analysis

Synthesis of Polyurethane

PEG has been extensively studied and widely used as the soft segment in PUs to enhance their anti-fouling properties, however, the fouling issues remain unsolved. To address these long-standing fouling issues, DEAHA was designed, which combines crosslinker, hard segment and antifouling functions. DEAHA was synthesized via Michael type reaction of diethanolamine and 2-hydroxyethyl acrylate. The chemical structure of DEAHA was characterized and confirmed by $^1$H NMR spectroscopy.

In PCBHUs, since DEAHA functions as both crosslinker and antifouling group, the mechanical, swelling, and anti-fouling property was easily tuned by adjusting the ratio of soft and hard domains. In PU synthesis, polyols, such as glycerol and triethanolamine, were used to tune the mechanical and processing properties of the materials. DEAHA can not only provide the same function as the crosslinker, it can also provide the anti-fouling properties. In addition, DEAHA can be either used as the additive or used to replace the existing crosslinker without significantly changing the reaction and processing conditions.

Fourier Transform Infrared Spectroscopy (FT-IR)

To confirm the completion of the condensation polymerization of PU, the obtained PU materials with different component ratios were characterized by FT-IR. FIG. 1 shows representative FT-IR spectra of PCBHU-2, PCBHU-4, PCBHU-6, PCBHU-8 and PCBHU-10. FT-IR studies were carried out by focusing on principal regions such as —CH stretching (2,700-2,950 cm$^{-1}$), C=O stretching (1,620-1,740 cm$^{-1}$), —NH stretching (3,300-3500 cm$^{-1}$) and C—O—C stretching (1,050-1,150 cm$^{-1}$). In all PCBHUs, there was no signal at 2,270 cm$^{-1}$ (—NCO stretching) or 3,590 cm$^{-1}$ (O—H stretching), indicating all isocyanate groups and hydroxylate groups were consumed. The absorption bands of N—H stretching vibrations were observed at 3326 cm$^{-1}$, C—H stretching at 2863 cm$^{-1}$, C=O stretching at 1680 cm$^{-1}$ and C—O stretching at 1188 cm$^{-1}$. N—H deformation bands were observed in the range of 1,500-1,600 cm$^{-1}$. The sharp peaks ranging from 1,690-1,700 cm$^{-1}$ indicate C=O stretching vibrations of urethane and carboxyl group on the cross-linker side chain. Compared to PCBHU-2, PCBHU-4 and PCBHU-6; PCBHU-8 and PCBHU-10 showed stronger C=O stretching peaks indicating the higher ratio of DEAHA component. Aliphatic C—H stretching mode of 2,880-2,929 cm$^{-1}$ and carboxylic stretching absorption band at 3,735-3,770 cm$^{-1}$ were also observed. Moreover, IR spectra showed the characteristic C—O—C stretching bands of soft segments at 1193 cm$^{-1}$, 1170 cm$^{-1}$ and 1188 cm$^{-1}$. These vibrations are a convincing evidence for the formation of PU. Additionally, PCBHU-2, PCBHU-4, PCBHU-6 and PCBHU-8 showed higher peaks of C—O stretching, which demonstrated a higher ratio of soft segments, as compared to PCBHU-10. FT-IR results confirmed the formation of PU and the complete consumption of isocyanate groups and hydroxylate groups. As isocyanate is toxic, it was necessary to quench completely consume all of the isocyanate.

Thermal Stability and Thermal Transition

Figure 2:
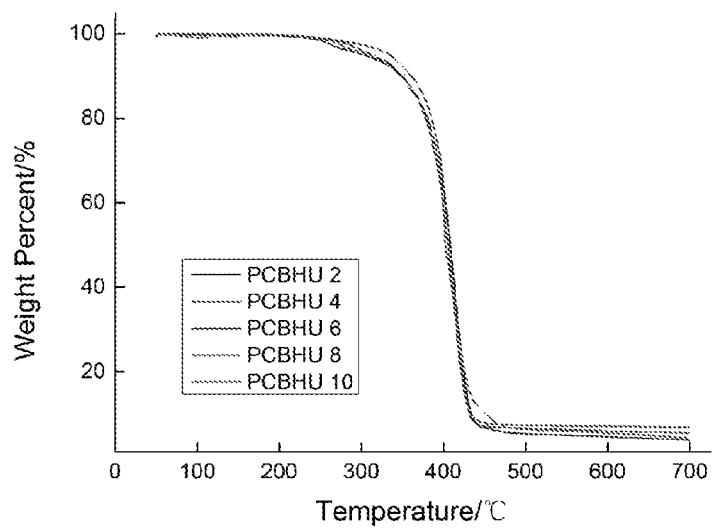
FIG. 2 shows the TGA profiles of PCBHUs with different component ratios.

Evaluating the thermal stability of PUs helps determine the polymer's processing method and temperature. In this study, TGA was used to evaluate the thermal stability of the PCBHU samples. The decomposition of polyurethane usually undergoes three stages. In the first stage, the urethane bonds decompose to form alcohols and isocyanates. The resulting chain fragments are then prevented from degradation by the dimerization of isocyanates to carbodiimides, which react with the hydroxyl groups to give relatively stable substituted urea. The final step is the high temperature degradation of these stabilized structures to yield volatile products and a small quantity of carbonaceous chain. FIG. 2 shows the TGA profile observed for PCBHUs under nitrogen. All PCBHUs displayed two weight loss stages at 305° C. and 456° C., respectively, and eventually formed a small amount of high-temperature residue (7.0 wt %). The first TGA stage can be related to the urethane bond degradation and stabilized urea bond formation whereas the second peak corresponded to decomposition of the urea structures. The higher thermal stability of these polymers provides a larger processing window.

Figure 3:
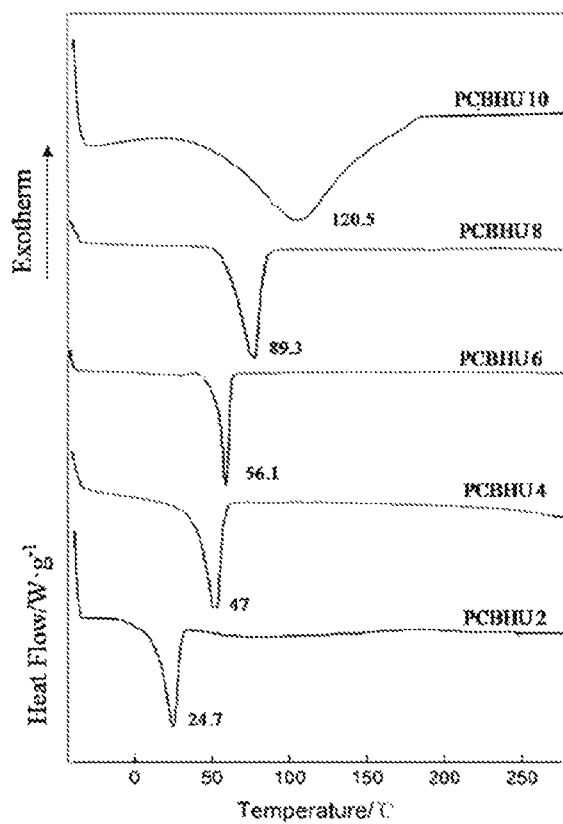
FIG. 3 shows the DSC profiles of PCBHUs with different component ratios.

The thermal transition of PU with different component ratios were characterized by DSC and are shown in FIG. 3. The melting temperature for PCBHU-10, PCBHU-8, PCBHU-6, PCBHU-4 and PCBHU-2 were 120.5° C., 89.3° C., 56.1° C., 47° C. and 24.7° C., respectively. As the hard segment content increased, the melting temperature increased due to the lower crosslinker density.

Hydrolysis Process Monitoring by pH Change

The main function of DEAHA in PCBHUs is to provide anti-fouling property after the hydrolysis of ester bond that lead to the formation zwitterionic carboxybetaine at the material/solution interface. Before the hydrolysis, DEAHA contains a tertiary amine group. In DI water, the tertiary amine is protonated and OH$^-$ ion leads to the increase of pH. The OH$^-$ groups then facilitates the hydrolysis of the ester group and leads to the formation of carboxylate group, leading to a drop in pH. In this study, pH values were recorded to monitor the hydrolysis process of polyurethane materials with different component ratios (PCBHU-4, PCBHU-6, PCBHU-8, PCBHU-10) in deionized water. All solutions containing PCBHUs were basic initially. The protonation of tertiary amine from unhydrolyzed PCBHU cause the pH value of all solutions decreased with time. The pH value of the samples (PCBHU-4 and PCBHU-6) with lower DEAHA ratio after hydrolysis was lower than that with higher DEAHA ratio (PCBHU-8 and PCBHU-10). Without intending to be bound by theory, this may be because, with the increase of the PEG component, the swelling ratio of the hydrogel has a synergetic effect with hydrolysis of the cross-linker component to decrease the pH values. These results indicated that the tunable swelling ratio not only depends on the soft segment molar ratio but is also related to the decrease of cross-link density caused by hydrolysis.

Swelling Study

Swelling experiments were also utilized to characterize the water uptake of the PCBHUs incorporating distinct compositions. Without intending to be bound by theory, as the feed ratio of PEG increases, the spacing between the cross-linkers becomes larger and therefore the resulting materials will have a larger mesh size, exhibiting a higher swelling ratio. Table 1 shows the differences in swelling ratio for the PCBHU hydrogels. The results of this study demonstrated a significant difference in swelling ratio between PCBHU hydrogels with different ratios of soft segments and hard segments. Especially, due to the high-water solubility and low crosslinker ratio, PCBHU-2 completely dissolved in DI water. PCBHU-4 and PCBHU-6 have a higher swelling ratio (Table 1) than that of PCBHU-8 and PCBHU-10. In addition, the size changes were also measured after hydrolysis. The original radius was 8 mm for each PCBHUs. After hydrolysis, the radius became 15 mm, 14 mm and 13 mm for PCBHU-4, PCBHU-6 and PCBHU-8, respectively. These results correspond to the swelling ratio studies.

TABLE 1

Compressive moduli, breaking strain, and swelling ratio of PCBHUs with different component ratios.

| | Before Hydrolysis | | After Hydrolysis | | |
|---|---|---|---|---|---|
| | Compressive modulus kPa | Breaking strain % | Compressive modulus kPa | Breaking strain % | Swelling ratio % |
| PCBHU 10 | 1026.5 | 50.1 | 294.1 | 86.5 | 37.6 |
| PCBHU 8 | 465.2 | 62.4 | 133.3 | 100.4 | 335.3 |
| PCBHU 6 | 390.9 | 67.2 | 14.5 | 120.4 | 1071.1 |
| PCBHU 4 | 174.1 | 80.1 | / | / | 3644.4 |
| PCBHU 2 | / | / | / | / | / |

Mechanical Properties

Figure 4:
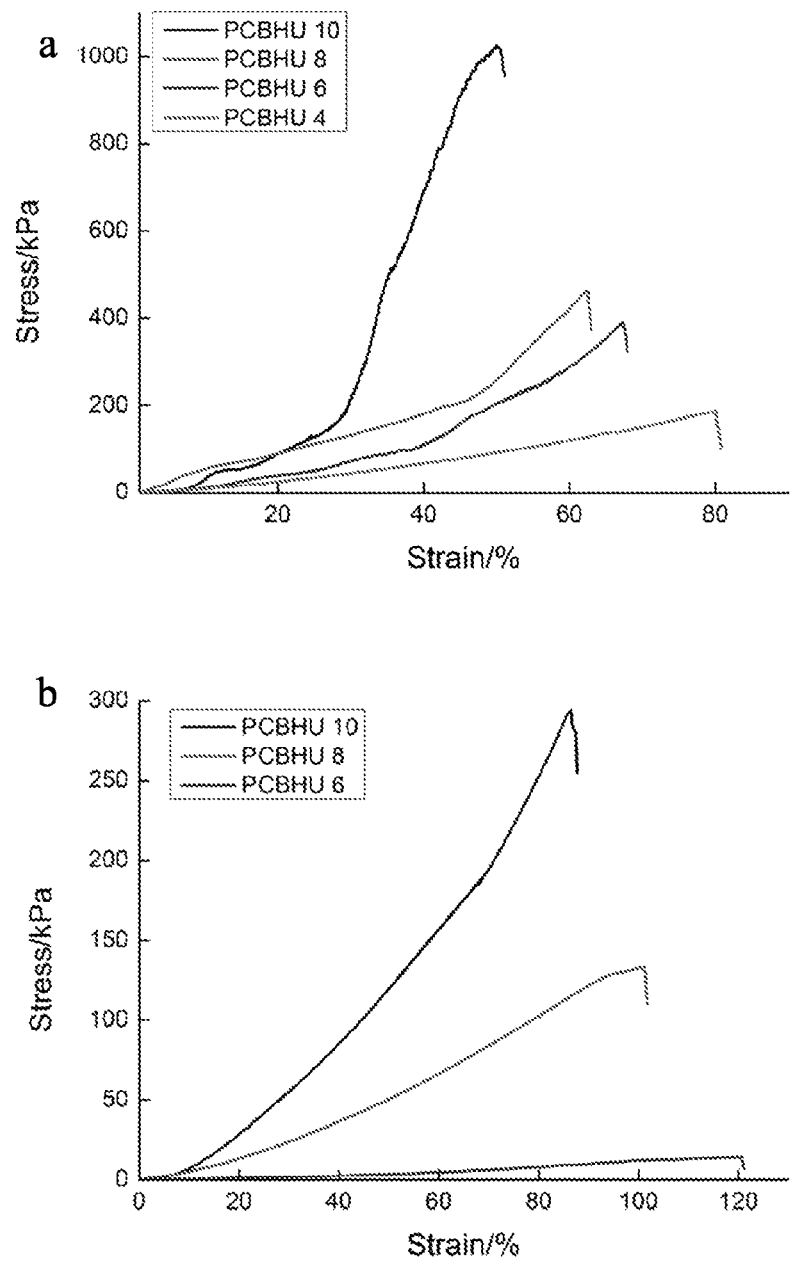
FIG. 4 shows the compressive stress-strain curve of PCBHU polyurethane materials with different component ratios (a) before and (b) after hydrolysis.

Tunable mechanical properties for biomaterials are highly desired, since the requirement for mechanical properties of the materials depends on applications. FIG. 4a and FIG. 4b are the stress-strain curves for the compression test of PCBHUs before and after hydrolysis. Before hydrolysis, with an increase of the molar ratio of DEAHA cross-linker, the value of compressive moduli increased from 174.1 kPa (PCBHU-4) to 1026.5 kPa (PCBHU-10), whereas the value of breaking strain decreased from 80.13% (PCBHU-4) to 50.1% (PCBHU-10) (Table 1). Before the hydrolysis, the compressive moduli of PCBHUs were enhanced when the hard segment content increased. This was indicative of a good interfacial adhesion between hard and soft domains and higher crosslinking density. Meanwhile, the elasticity of the sample was compromised with increase of the cross-linker, which, without intending to be bound by theory, was likely due to the embrittlement effect caused by increasing the interfacial area between hard and soft segments. After hydrolysis, the compressive moduli of PCBHUs followed the similar trend as the material before the hydrolysis, ranging from 14.5 kPa (PCBHU-6) to 298.1 kPa (PCBHU-10). The breaking strain significantly increased to 120.4% (PCBHU-6) and 86.5% (PCBHU-6) after hydrolysis. After hydrolysis, the higher equilibrium water content and swelling ratio of samples with lower cross-link density may be the cause of the lower compressive modulus. This study demonstrated that cross-linking density can be adjusted to obtain a moderate swelling ratio and suitable elasticity for different applications.

Protein Adsorption

Figure 5:
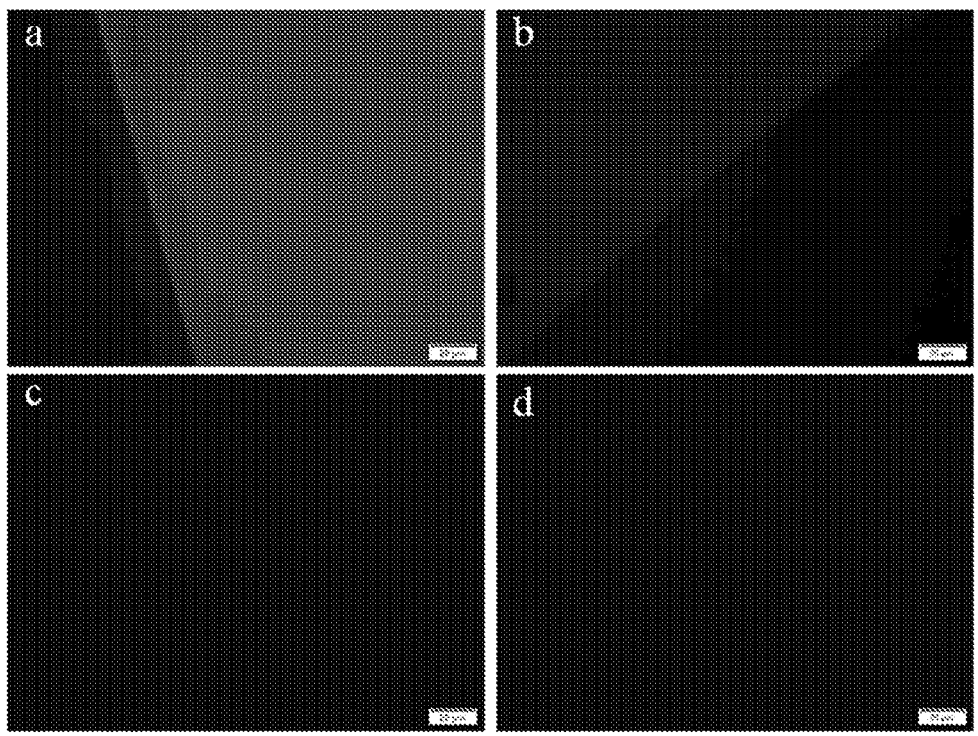
FIG. 5 shows the fluorescence images for protein adsorption of (a) commercially available API-PU, (b) PGHU-8 hydrogel, (c) PCBHU-8 hydrogel and (d) PCBHU-10 hydrogel. Compared to 100% protein adsorption of commercial biomedical polyurethane material, the fluorescence intensity was 37.64%, 2.16% and 0.68% for PHG-8, PCBHU-8 and PCBHU-10 hydrogels, respectively.

Protein adsorption on the surface of implanted medical devices can cause foreign body response, blood coagulation and/or inflammation, affecting the sensitivity of the device. One of the disadvantages for polyurethane biomaterials is their unsatisfactory capability of resisting protein adsorption from the complex media, such as blood and body fluids. In this study, protein adsorption studies were conducted on the PCBHU surfaces and quantified by a fluorescent method. Four samples were compared. Commercially-available medical grade PU (API-PU) films were used as a control material. After reaching equilibrium in PBS, PCBHU samples were briefly rinsed with DI water, and submerged in FITC-BSA solution. Materials having no contact with FITC-BSA were used as the control. All images of different samples were obtained from the fluorescence microscope at the same excitation light intensity and exposure time thereafter. As shown in FIG. 5, among all samples API-PU shows the highest fluorescence intensity, which indicates the highest protein adsorption. The sample with highest CB ratio (PCBHU-10) showed the lowest amount of absorbed protein, while the sample with a composition of 8:2:10 of Glycerol:PEG:HDI (PGHU-8) showed a medium fluorescence density. Compared to API-PU (set as 100% protein adsorption), the protein adsorption on PGHU-8, PCBHU-8 and PCBHU-10 were 37.64%, 2.16% and 0.68%, respectively. The results demonstrated PCBHU-8 and PCBHU-10 were highly resistant to protein adsorption.

The excellent antifouling property of PCBHU was due to the strong hydration of the CB groups that were generated via the hydrolysis of DEAHAs. Previous studies discovered that the strong hydration layer of the zwitterionic materials provided an effective barrier to prevent foulants to interact with the material surfaces. To determine their hydrophilicity, the water contact angle of PCBHUs and control surfaces were measured. Compared to API-PU (contact angle of 87.07°), the contact angles of PGHU-8, PCBHU-6, and PCBHU-8 were 62.52°, 56.10°, and 55.24°. Accordingly, these results demonstrate that the incorporation of zwitterionic groups render the PCBHU surfaces more hydrophilic.

Cell Attachment

Figure 6:
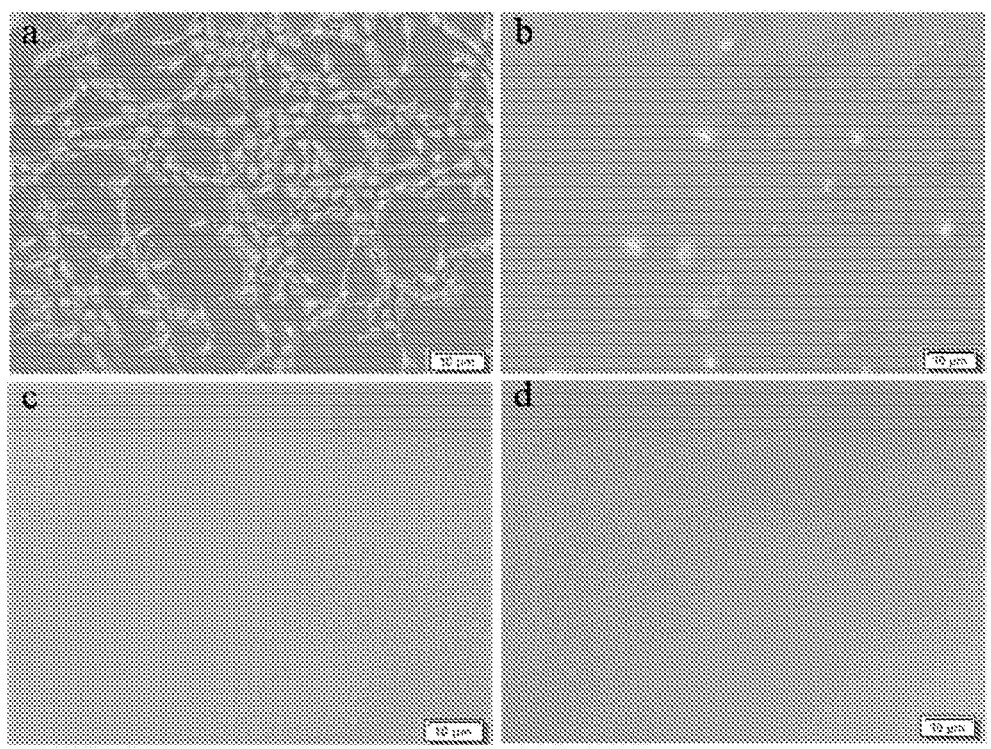
FIG. 6 shows images for NIH-3T3 cell attachment of (a) commercially available API-PU, (b) PGHU-8 hydrogel, (c) PCBHU-8 hydrogel and (d) PCBHU-10 hydrogel. The cell densities on tissue culture polystyrene (TCPS) and PGHU-8 hydrogel surface were $(195.12\pm3.56)\times10^4$ cells/cm$^2$, $(19.51\pm1.74)\times10^4$ cells/cm$^2$, respectively. But for the PCBHU-8 and PCBHU-10 surface, there was no observable cell.

For implantable biomedical devices, protein adsorption on surfaces from blood can trigger platelet and monocyte attachment. The attachment of these cells leads to thrombosis and foreign body response, which can result in inflammation around the implanted materials/devices. To further confirm the anti-fouling properties of PCBHU materials, cell adhesion studies were performed with NIH-3T3 fibroblast cells. After incubation at 37° C. for 24 hours, the control tissue culture polystyrene (TCPS) surface demonstrated a full coverage of NIH-3T3 fibroblast cells. The cell densities on tissue culture polystyrene (TCPS) and PGHU-8 hydrogel surface were $(195.12\pm3.56)\times10^4$ cells/cm$^2$ and $(19.51\pm1.74)\times10^4$ cells/cm$^2$, respectively. There was almost no cell attachment on PCBHU-8 and PCBHU-10 surfaces (FIG. 6). These results indicated that the zwitterionic PCBHU materials highly resist cell adhesion. PCBHU materials potentially can be applied or molded into implanted devices to solve long-standing device-induced thrombosis and inflammation.

Bacterial Attachment and Biofilm Formation

Figure 7:
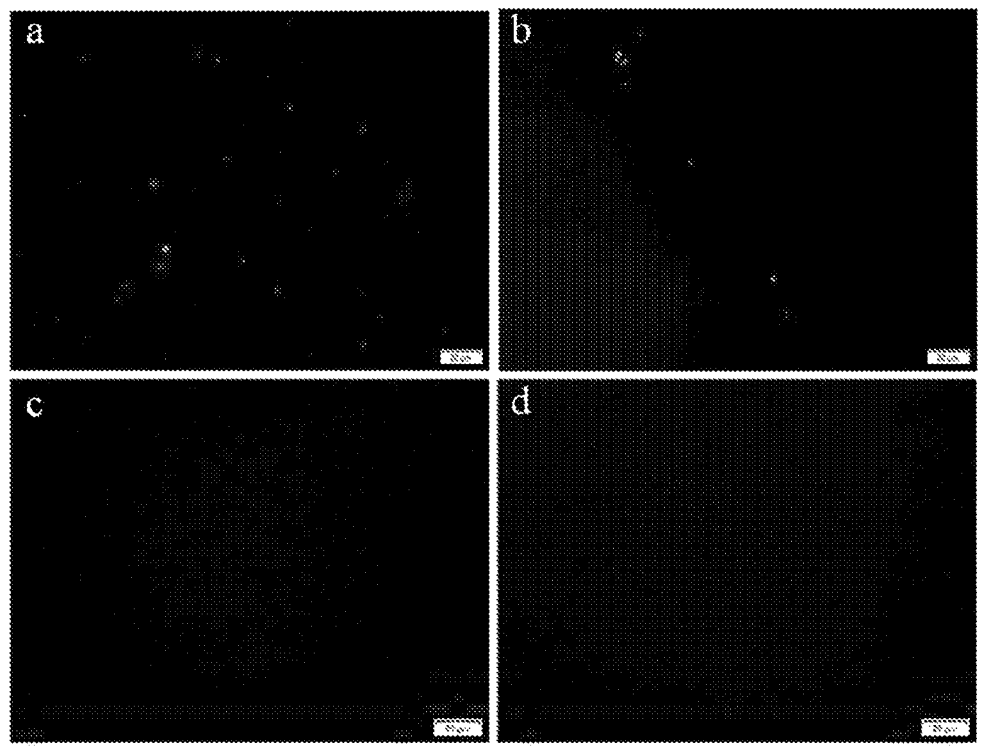
FIG. 7 shows fluorescence images for *E. coli* K12 adhesion on (a) commercially available API-PU, (b) PGHU-8 hydrogel, (c) PCBHU-8 hydrogel and (d) PCBHU-10 hydrogel. The cell densities on commercial biomedical polyurethane material and PHG-8 hydrogel surface were $(52.13\pm2.43)\times10^4$ cells/cm$^2$, $(13.72\pm0.47)\times10^4$ cells/cm$^2$, respectively. But for the PCBHU-8 and PCBHU-10 surface, there was no observable *E. coli* K12 cell.

Infection and biofilm formation on implants is a major cause of the implant failure. Biofilm starts with the initial attachment of microorganisms. Once biofilm is formed, the microorganisms in the biofilm are no longer sensitive to antimicrobial agents. Biomaterials with superior properties to resist bacterial attachment and biofilm formation are very useful for biomedical devices. Bacterial cell attachment onto PCBHU surfaces was investigated using *E. coli* K12 as a model cell. *E. coli* K12 at the concentration of $10^8$ cells/mL was incubated with PCBHU surfaces in buffer. FIG. 7 shows almost no bacterial cells were observed on the PCBHU-8 and PCBHU-10 surfaces in the solution after 1 hour. In contrast, much more *E. coli* K12 cells attached to the commercial biomedical polyurethane materials surfaces. The cell densities on the surface of API-PU and PGHU-8 materials were $(5.21\pm0.24)\times10^5$ cells/cm$^2$ and $(1.372\pm0.05)\times 10^5$ cells/cm$^2$, respectively. Nevertheless, there was almost no observable bacterial cell attached onto PCBHU surfaces. The bacterial attachment experiment demonstrated a great anti-fouling hydrogel surface for the PCBHU polyurethane materials, which makes it a promising candidate for biomedical device applications.

Figure 8:
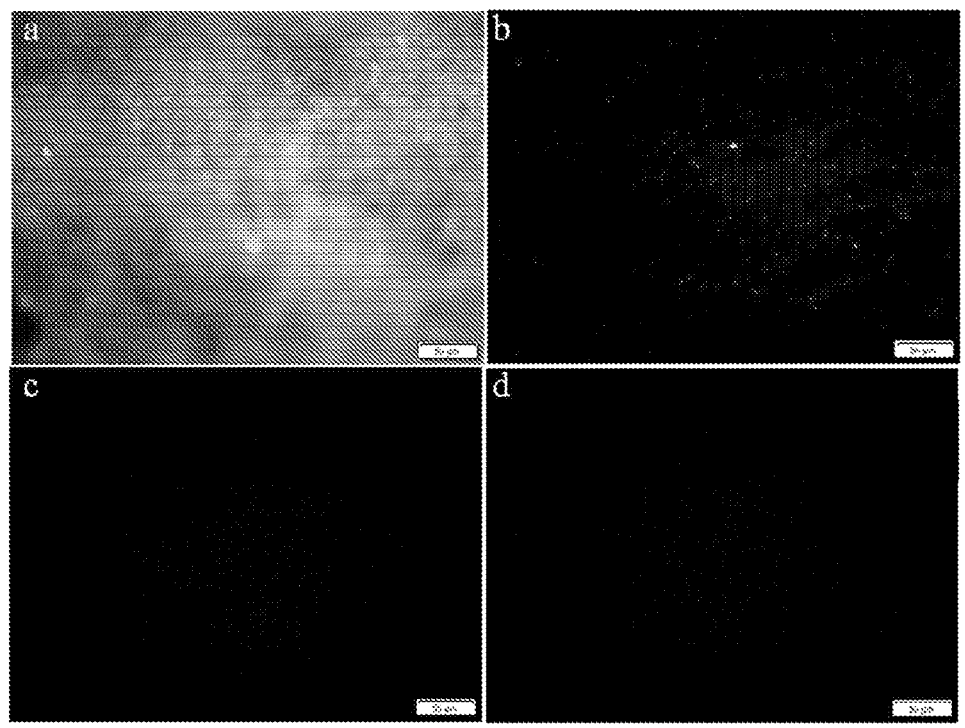
FIG. 8 shows fluorescence images for *Pseudomonas aeruginosa* PAO1 biofilm formation of (a) commercially available API-PU, (b) PGHU-8 hydrogel, (c) PCBHU-8 and (d) PCBHU-10.

The long-term biofilm formation of *P. aeruginosa* was also studied on PCBHU surfaces. As shown in FIG. 8, no *P. aeruginosa* PAO1 bacterial cells were observed on PCBHU-8 and PCBHU-10 surfaces as compared to the PHG 8 and API-PU surfaces after two weeks. API-PU surface was completely covered by *P. aeruginosa* at 25° C. after 2 weeks. The cell density on PHG-8 surface was about 26.33% compared to API-PU. This study shows zwitterionic PCBHU surfaces possess a great capability to resist bacterial adhesion and biofilm formation.

Accordingly, Example 1 demonstrates the synthesis of a series of zwitterionic PCBHUs with CBs as part of the polyurethane backbone, and where the CB content in the polymer could be readily tuned by altering the molar ratio of PEG and DEAHA triol. Example 1 demonstrates the relationships among structure, function, and stability of zwitterionic materials. The mechanical properties and swelling ratio were sensitive to the CB precursor, DEAHA, content. TGA and DSC results show that the coatings were thermally stable. PCBHUs, such as PCBHU-8 and PCBHU-10 with higher DEAHA cross-linker ratios, markedly reduced protein adsorption, cell attachment, bacterial attachment, and biofilm formation. Thus, the dual-function of both tunable surface and bulk properties was been achieved in one single polyurethane material.

Example 2—Synthesis and Evaluation of Zwitterionic Polymer

Synthesis of Diethanoamino Ethyl Acrylate (DEAEA)

DEAEA (structure provided below) was synthesized using a Michael-type reaction.

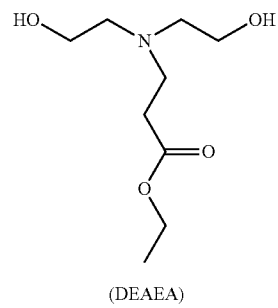

(DEAEA)

Diethanolamine (50 g, 0.476 mol) was added into ethyl acrylate (48 g, 0.48 mol) dropwise with nitrogen purged. The resulting solution was stirred overnight under 35° C. The reaction mixture was concentrated in a rotavapor and then purified by flash chromatography using dichloromethane and methanol mixture (9:1) as the mobile phase to yield DEAEA. 1H NMR (400 MHz, CDCl3, ppm): 3.46 (t, 4H), 2.74 (t, 2H), 2.51 (t, 4H), 2.36 (t, 2H), 1.14 (t, 3H), 4.01 (m, 2H).

Synthesis of Polymer

Five polymers with different stoichiometric ratios of hydroxyl groups in DEAEA/hydroxyl groups of glycerol/isocyanate groups in HDI (100:0:100, 75:25:100, 50:50:100, 25:75:100, and 0:100:100) were prepared and named DHG-0, DHG-25, DHG-50, DHG-75, and DHG-100, respectively. A control polymer PGHU-8 with the ratios of hydroxyl groups in glycerol/hydroxyl groups of PEG/isocyanate groups in HDI (8:2:10) as a control was also synthesized. The polymers were synthesized via a one-pot reaction. The synthesis of the polymers followed the general reaction scheme, below:

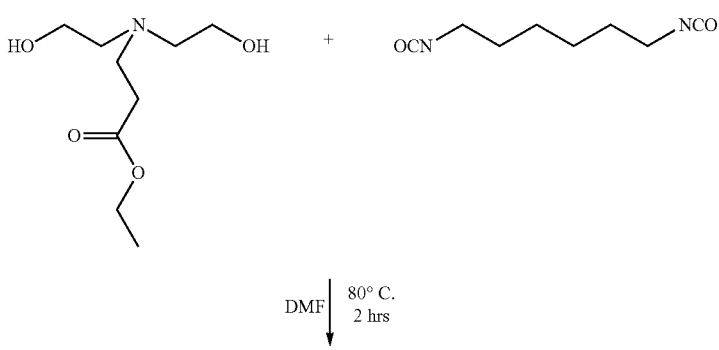

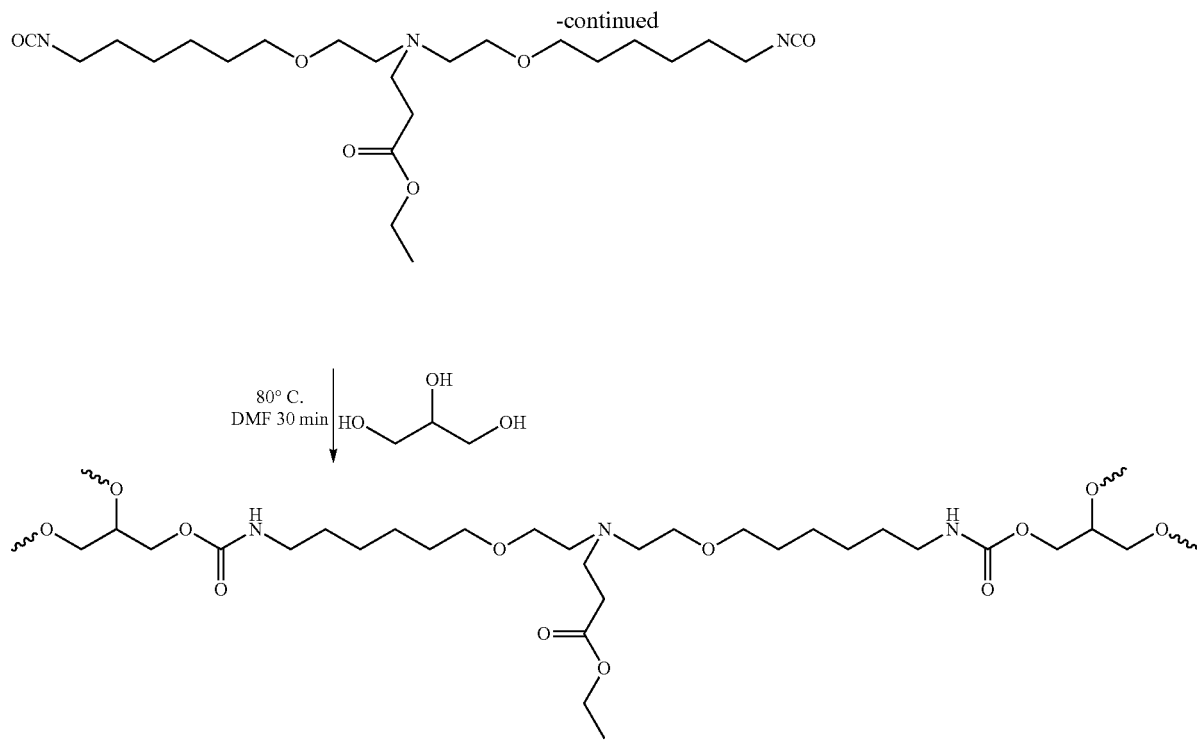

PU-Prepolymer was synthesized in a three-necked round bottom flask equipped with a mechanical stirrer, a temperature controller and a nitrogen inlet. The reaction was carried out in a nitrogen atmosphere. Before reaction, DEAEA was placed into vacuum oven under 110° C. for 2 hours for removing moisture. The HDI was then added into three-necked round bottom flask dropwise. Anhydrous DMF was added once the viscosity increased. The prepolymer solution was stirred for 2 hours under 80° C. Glycerol as chain extender was added into the solution dropwise and stirred for another 30 minutes under 80° C. The mixing solution was then poured into PTEF dishes and stored in the oven under 100° C. for 12 hours. The resulting polyurethane was dried under 100° C. in the vacuum oven for 12 hours to remove residual solvent. After drying, PU films were peeled off and cut into discs with a biophysical punch (8 mm in diameter and 2 mm in thickness).

Analysis

Synthesis of Polyurethane

A multifunctional block component, DEAEA, was prepared to combines soft segments and antifouling functions to a polyurethane polymer. DEAEA was synthesized via Michael type reaction of diethanolamine and ethyl acrylate. The chemical structure of DEAEA was characterized and confirmed by $^1$H NMR spectroscopy. The PU materials with different monomer ratios were synthesized via a one pot reaction using glycerol as crosslinker and hard segment. Glycerol was widely used in biomedical polyurethane production due to its excellent biocompatibility and low cost. DEAEA functions as both soft segment and anti-fouling precursor in DHG, the mechanical, swelling and anti-fouling properties can be readily tuned by adjusting the ratio of soft and hard domains.

Fourier Transform Infrared Spectroscopy (FT-IR)

The FT-IR spectra of synthesized DHG PUs were obtained. The absence of absorbance at 2250-2270 cm$^{-1}$, related to —NCO stretching, indicated that the reaction proceeded until complete conversion of the isocyanate groups. The absorption bands of N—H stretching vibrations were observed at 3321 cm$^{-1}$, C—H stretching at 2922 cm$^{-1}$, C═O stretching at 1698 cm$^{-1}$ and C—O stretching at 1140 cm$^{-1}$. N—H deformation bands were observed in the range of 1,500-1,600 cm$^{-1}$. The sharp peaks ranging from 1,690-1,700 cm$^{-1}$ indicated C═O stretching vibrations of urethane and carboxyl group on the DEAEA side chain. Aliphatic C—H stretching mode of 2,880-2,929 cm$^{-1}$ and carboxylic stretching absorption band at 3,735-3,770 cm$^{-1}$ were also observed. The IR spectra demonstrated the characteristic peaks for C—O—C stretching of hard segment at 1140 cm$^{-1}$. This signature stretching bands was an indication for the formation of PU. FT-IR spectra confirmed the formation of PU and complete consumption of isocyanate groups.

Thermal Stability and Thermal Transition

The thermal stability of DHG PUs were determined by TGA measurement. As described in Example 1, the polyurethane deposition typically undergoes three stages. The TGA and DTG profiles of the DHG PUs showed three steps, the first step attributed to decomposition of urethane bonds, the second and third step were considered consecutive and related to the decomposition of substituted urea bonds. According to the TGA curve, for DHG-0, DHG-25, DHDG-50 and DHG-75 samples, 43% mass loss occurs between 200 and 300° C. in the first step and around 42-48% mass loss from 300 to 500° C. in the second step. For the sample with higher crosslinker density DHG 100, the first step shows a higher decomposition temperature between 250 to 350° C. with 46% mass loss and the second step exhibits 44% mass loss from 370 to 500° C. Finally, a small quantity of high-temperature residues (7.3-15.8 wt %) were left. The TGA studies indicated that the DHG PU have similar high thermal stability with commercially available PU materials.

The thermal transition behaviors of DHG PU were also measured by DSC. The glass transition temperature and melting temperature of PU with different component ratios were shown in Table 2, below.

TABLE 2

Glass Transition Temperature and Melting Temperature for DHG Polymers

| Sample | Tg (° C.) | Tm (° C.) |
| --- | --- | --- |
| DHG-0 | 39.7 | 203.7 |
| DHG-25 | 12.0 | 221.7 |
| DHG-50 | 15.3 | 227.0 |
| DHG-75 | 38.3 | 227.7 |
| DHG-100 | 45.3 | 241.7 |

As shown in Table 2, except for DHG-0, the glass transition temperature of other samples was increased with the crosslink density. For DHG-0, there were only polyols reacting with diisocyanates, which made the molecular weight reach infinity resulting in polymer chain entanglements. Therefore, DHG-0 has a relatively high glass transition temperature. The melting temperature of DHG PU with different ratios demonstrated a tendency that as the hard segment content increased, the melting temperature increased due to the higher crosslink density.

Hydrolysis of DHG PU

The antifouling property of PU was obtained after hydrolysis of ester bond in DEAEA resulting in the formation of zwitterionic carboxybetaine at the interfaces of material and solvent. Before hydrolysis, the tertiary amines in DEAEA were protonated in DI water. The resulting hydroxide ions led to pH value increase. High local pH facilitated the hydrolysis of the ester bond and caused the formation of carboxylate groups. The pH value decreased during this process and finally became stable. To monitor the hydrolysis process, the pH values of each sample were recorded with time. All the solutions were basic at the beginning and subsequently the pH values of all solutions decreased as a function of time. Compared to DHG-0, DHG-75 and DHG-100, the pH value of DHG-0 and DHG-25 were lower, which was due to higher cross-link density. With the increase of DEAEA ratios, the larger swelling ratio resulted in more DEAEA component exposed to the water and hydrolysis. After two days, the hydrolysis of DHG PU was complete for all solutions.

Swelling Study

The water uptakes of DHG PU with different components were characterized by swelling ratio studies. Without intending to be bound by theory, with the increase of DEAEA component, the cross-link density would be lower and the mesh size between materials would be larger, which would cause a higher swelling ratio. The swelling ratios of PU with distinct composition were shown in Table 3, below.

TABLE 3

Compressive moduli, breaking strain and swelling ratio of DHG polyurethane materials with different component.

| | Before Hydrolysis | | After Hydrolysis | | Swelling ratio, % |
| --- | --- | --- | --- | --- | --- |
| Sample | Compressive modulus, kPa | Breaking Strain, % | Compressive modulus, kPa | Breaking Strain, % | |
| DHG-0 | / | / | 1510.6 | 45.8 | 35.3 |
| DHG-25 | 934.9 | 60.2 | 604.3 | 51.7 | 10.1 |
| DHG-50 | / | / | 1713.3 | 74.2 | 9.4 |
| DHG-75 | 7964.6 | 91.3 | 785.1 | 52.7 | 8.4 |
| DHG-100 | / | / | 2395.8 | 32.7 | 9.8 |

The study results demonstrated that DHG-0 and DHG-25 had a higher swelling ratio than that of DHG-50, DHG-75 and DHG-100. This result indicated that the swelling ratio of DHG PU materials can be adjusted by the feed ratio of DEAEA and cross-linkers.

Mechanical Properties

Tunable mechanical properties for DHG PU materials can be achieved by adjusting the feed ratio between polyols and crosslinkers. The compression test of DHG PU samples with 8 mm in diameter and 2 mm in thickness was conducted under certain strain rate. As shown in Table 3, above, DHG-0, DHG-50 and DHG-100 exhibit great mechanical properties with both high compression modulus and breaking strain before hydrolysis. These results indicated a good interfacial strength between soft and hard domain. But DHG-25 and DHG-75 did not demonstrate a good breaking modulus (934.9 kPa and 7964.6 kPa) and breaking strain (60.2% and 91.3%). Without intending to be bound by theory, this is likely because the phase separation structure led to the failure point that easily cause breaking. After hydrolysis, the water absorbed in the DHG PU materials resulted in decrease of mechanical properties. The DHG-0, DHG-50 and DHG-100 showed a relatively high compression modulus (1510.6 kPa, 1713.3 kPa and 2395.8 kPa, respectively). Among all the samples, DHG-100 displayed the highest compression modulus, which was likely attributed to the highest crosslinking density. DHG-50 had the second-highest strain rate, which contributed to better elasticity due to good interfacial strength between soft and hard domains.

Protein Adsorption

As described above, protein adsorption is an important consideration for the materials that used in implanted medical devices. The protein adsorption was measured on the surface of DHG PU and quantified by a fluorescent method. DHG-100, which did not include carboxybetaine moieties was the control material in this study. Among all samples, DHG 100 demonstrated the highest fluorescence intensity, which indicated the highest protein adsorption. Compared to DHG 100, the protein adsorption on DHG-0, DHG-25, DHG-50 and DHG-75 were 0.39%, 2.74%, 2.16% and 3.04%. respectively. This result indicated that the PU containing CB moieties highly resist protein adsorption.

Cell Attachment

As described above, the affinity of cells to surfaces is an important consideration for biomaterials design and development, especially implanted biomedical devices. To further confirm the anti-fouling properties of DHG PU, cell attachment studies were conducted with NIH-3T3 fibroblast cells. After being incubated at 37° C. for 24 hours, the cell densities on DHD-100 hydrogel and TCPS surface were $(14.95\pm1.89)\times10^4$ cells/cm$^2$ and $(62.20\pm2.57)\times10^4$ cells/cm$^2$, respectively. There was no cell observed on the other surfaces. This indicated that the zwitterionic CB moieties were highly capable of resisting cell adhesions. Accordingly, a biomedical polyurethane material with great anti-fouling property to cell attachment has been prepared.

Bacterial Attachment and Biofilm Formation

As described above, biofilm will form after long-term bacterial attachment in most natural environments, creating a antibacterial-resistant surface on implantable medical devices.

Bacterial attachment studies were conducted on the surface of DHG PU using *P. aeruginosa* POA1 as a model. The density on the surface of DHG-100 was $(52.13\pm2.43)\times10^4$ cells/cm$^2$. There was almost no observable bacterial cell attached on the other surfaces. The bacterial attachment study exhibited an excellent anti-fouling surface for DHG polyurethane materials that can be used in biomedical device applications.

To further confirm the capability of DHG PU to resist biofilm formation, the *P. aeruginosa* POA1 were incubated on the surfaces of DHG under 25° C. for two weeks. After two weeks, no bacterial cells were observed on DHG-0, DHG-25, DHG-50 and DHG-75 surfaces compared to DHG 100 that was almost completely covered by biofilm. Thus, the zwitterionic DHG PU surface have been shown to demonstrate excellent abilities to resist bacterial adhesion and biofilm formation.

Accordingly, Example 2 demonstrates that a series of zwitterionic DHG PUs were synthesized with different CB feed ratio resulting in adjustable mechanical properties and swelling ratio. TGA and DSC studies indicated the polyurethanes were thermally stable. The DHG PUs with DEAEA component exhibited a dramatically reduction on protein adsorption, cell attachment, bacterial adhesion and biofilm formation. Therefore, the polyurethane with both tunable surface and bulk properties has been achieved in one single material and their excellent potential in tailoring polymer structures to achieve desired functions to suit a variety of applications.

Example 3—Synthesis and Evaluation of Zwitterionic Polymer

Synthesis of Diethanoamino Ethyl Acrylate (DEAEA)

DEAEA (structure provided below) was synthesized using a Michael-type reaction.

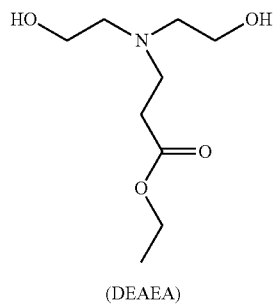

(DEAEA)

Diethanolamine (50 g, 0.476 mol) was added into ethyl acrylate (48 g, 0.48 mol) dropwise with nitrogen purged. The resulting solution was stirred overnight under 35° C. The reaction mixture was concentrated in a rotavapor and then purified by flash chromatography using dichloromethane and methanol mixture (9:1) as the mobile phase to yield DEAEA. 1H NMR (400 MHz, CDCl3, ppm): 3.46 (t, 4H), 2.74 (t, 2H), 2.51 (t, 4H), 2.36 (t, 2H), 1.14 (t, 3H), 4.01 (m, 2H).

Synthesis of Diethanoamino-N—Hydroxyl Ethyl Acetate (DEAHA)

DEAHA (structure provided below) was synthesized using a Michael-type reaction.

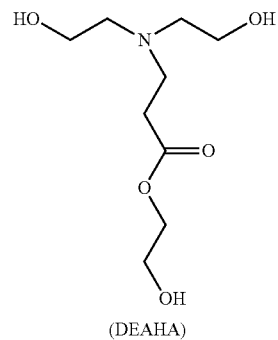 [SMILES: O=C(CCN(CCO)CCO)OCCO]

(DEAHA)

Diethanolamine (30 g, 0.28 mol) was added into 2-hydroxyethyl acrylate (36.4 g, 0.31 mol). The resulting solution was stirred overnight under 35° C., and kept away from the light during the reaction. The reaction mixture was concentrated in a rotovap and then purified by flash chromatography using a dichloromethanoe and methanol mixture (5:1) as the mobile phase to yield DEAHA. $^1$H NMR (400 MHz, CDCl$_3$, ppm): 4.03 (t, 2H), 3.59 (t, 2H), 2.67 (t, 2H), 2.35 (t, 2H), 3.42 (m, 4H), 2.44 (m, 4H).

Synthesis of Polymer

Five polymers with different stoichiometric ratios of hydroxyl groups in DEAEA/hydroxyl groups of DEAHA/ isocyanate groups in HDI (100:0:100, 75:25:100, 50:50:100, 25:75:100, and 0:100:100) were prepared and named DHD-0, DHD-25, DHD-50, DHD-75, and DHD-100, respectively. The polymers were synthesized via a one-pot reaction. The synthesis of the polymers followed the general reaction scheme, below:

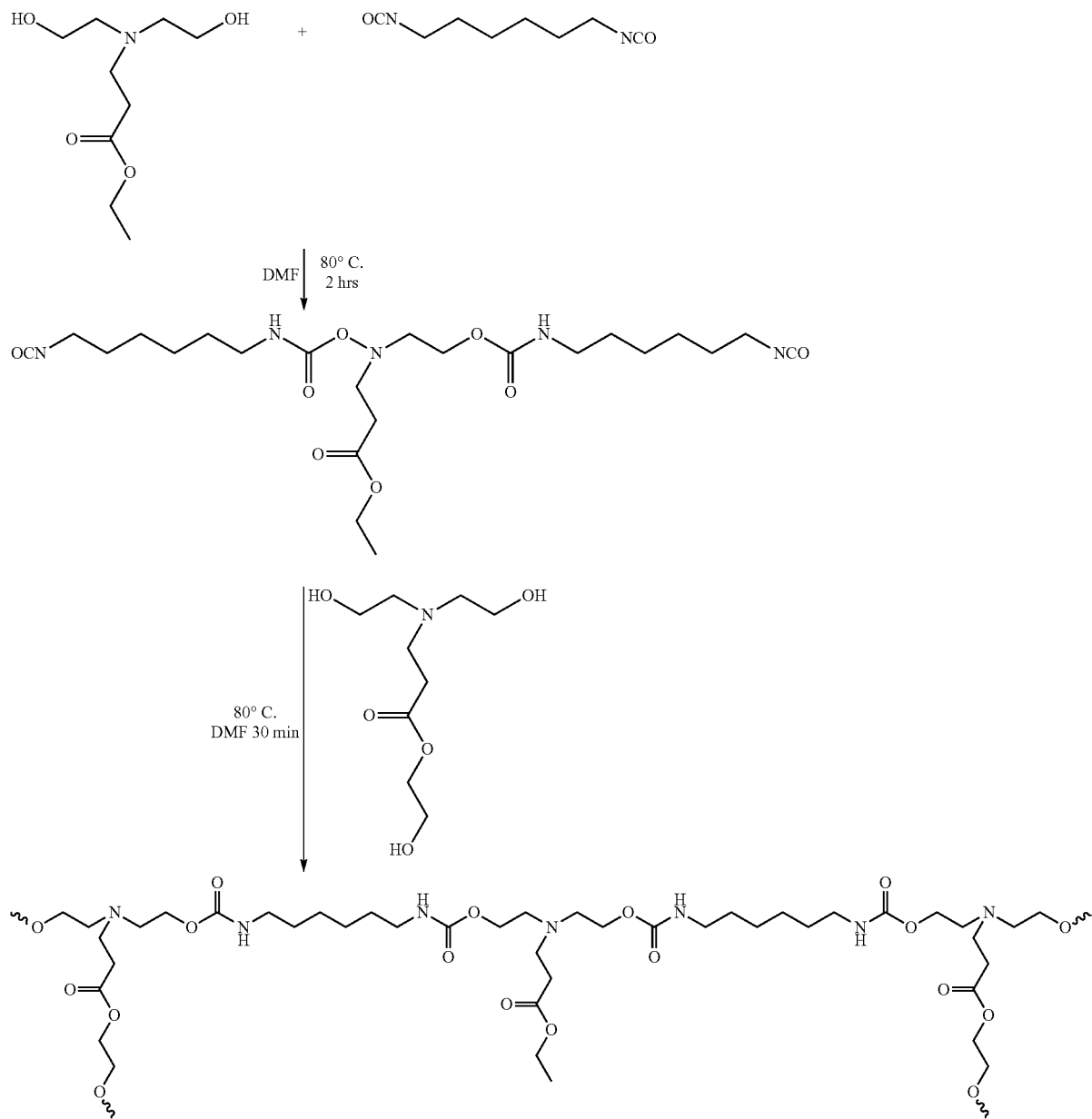

PU-Prepolymer was synthesized in a three-necked round bottom flask equipped with a mechanical stirrer, a temperature controller and a nitrogen inlet. The reaction was carried out in a nitrogen atmosphere. Before the reaction, DEAEA was placed into vacuum oven under 110° C. for 2 hours for removing moisture. The HDI was then added into three-necked round bottom flask dropwise. Anhydrous DMF was added once the viscosity increased. The prepolymer solution was stirred for 2 hours under 80° C. DEAHA was chain extender was added into the solution dropwise and stirred for another 30 minutes under 80° C. The mixing solution was then poured into PTFE dishes and stored in the oven under 100° C. for 12 hours. The resulting polyurethane was dried under 100° C. in the vacuum oven for 12 hours to remove residual solvent. After drying, PU films were peeled off and cut into discs with a biophysical punch (8 mm in diameter and 2 mm in thickness).

Analysis
Synthesis of Polyurethane

A multifunctional block component, DEAEA, was prepared to combines soft segments and antifouling functions to a polyurethane polymer. DEAHA acted as a crosslinker, hard segment and antifouling precursor. Both of DEAEA and DEAHA were synthesized via Michael type reactions. The chemical structures of DEAEA and DEAHA were characterized and confirmed by $^1$H NMR spectroscopy. The PU materials with different monomer ratios were synthesized via a one pot reaction. The tunability of the mechanical, swelling and anti-fouling properties were explored by adjusting the ratio of soft and hard domains.

Fourier Transform Infrared Spectroscopy (FT-IR)

The FT-IR spectra of synthesized DHD PUs were obtained. The absence of absorbance at 2250-2270 $cm^{-1}$, which is related to —NCO stretching, and at 3590 $cm^{-1}$ related to O—H stretching, indicated that the reaction proceeded until complete conversion of the isocyanate groups. The broad peak at 3326 cm$^{-1}$ was attributed to the bonded N—H with the carbonyl in the urethane. There were absorption bands of C—H stretching at 2918 cm$^{-1}$. The strong absorption peak of 1699 cm$^{-1}$ was attributed to C=O stretching vibration on carbonyl in the urethane groups. The C—O stretching was observed at 1103 cm$^{-1}$ and N—H deformation bands were observed in the range of 1500-1600 cm$^{-1}$. The 778 cm$^{-1}$ (C—N) (deformation vibration in tertiary amine) was the characteristic peak of DEAEA and DEAHA. These signature stretching bands demonstrated the successful formation of the DHD polymers. FT-IR results confirmed not only the formation of PU but the complete consumption of isocyanate groups as well.

Thermal Stability and Thermal Transition

The thermal stability of PU was characterized by TGA measurement. As described above, the decomposition of PU process usually goes through three stages. According to the TGA and DTG curves of the DHD polymers, two steps of the thermal decomposition were observed. In the first step, 39% mass loss occurs between 200 and 300° C. and in the second step 46% of mass loss between 300 and 490° C., corresponding to the break of urethane bonds and substituted urea bonds, respectively. Eventually, a small number of high-temperature residues (15.7 wt %) were left. The TGA results confirmed DHD PU have high thermal stability, which provides a wider processing window.

The thermal transition behavior of PU with different monomer ratios were measured by DSC studies. Based on the DSC profiles, there existed four different transition temperatures for each sample, which indicated both glass transition temperatures and melting temperatures for both soft domains and hard domains. These temperatures are provided in Table 4, below.

TABLE 4

Glass Transition Temperature and Melting Temperature for DHD Polymers

| Sample | $Tg_1$ (° C.) | $Tg_2$ (° C.) | $Tm_1$ (° C.) | $Tm_2$ (° C.) |
|---|---|---|---|---|
| DHD-0 | 4.3 | / | / | 221.7 |
| DHD-25 | 6.7 | 108.7 | 188.0 | 227.0 |
| DHD-50 | 13.3 | 105.0 | 186.3 | 228.0 |
| DHD-75 | 15.3 | 102.7 | 194.0 | 230.7 |
| DHD-100 | 20.0 | 115.0 | 187.7 | 229.7 |

As shown by these data, with increasing of ratio of hard domains, the glass transition temperature of soft domains increase. The glass transition temperature of soft domains and melting temperature of both soft domains and hard domains are around same amount, displaying a good interfacial strength between soft and hard domains.

Hydrolysis of DHG PU

As antifouling precursors, the ester bonds in both DEAEA and DEAHA will hydrolyze to form zwitterionic carboxybetaine structure at the interfaces of material and solvent. Before the hydrolysis, DEAEA and DEAHA are in a form of tertiary amine that is subsequently protonated in DI water, providing hydroxide ions that resulted in the increase of pH. High local pH facilitated hydrolysis of ester bonds and the formation of carboxylate groups. With the consumption of hydroxides, the pH value of the solution decreased and finally become stable after all ester bonds were hydrolyzed. In the hydrolysis study, pH values were recorded for each DHD PU samples to monitor the hydrolysis process. All of the solutions containing DHD PU were basic at beginning due to the tertiary amine protonation. Subsequently, the pH values decreased as function of time and eventually become stable. Compared to DHD-0, DHD-25 and DHD-50, the pH values of DHD-75 and DHD-100 were lower. Without intending to be bound by theory, this may have been caused by the break of ester bonds in DEAHA and the decrease in crosslink density. This study also indicated that after 48 hours, all the ester bonds completely hydrolyzed.

Swelling Study

The water uptakes of DHD PU with different components were characterized by swelling ratio studies. The swelling ratios of DHD PU were expected to be related to the feed ratio between DEAEA and DEAHA. Without intending to be bound by theory, with the increase of DEAHA component, the mesh size between crosslinkers will be smaller, demonstrating a lower swelling ratio. The swelling ratios of PU with distinct composition were shown in Table 5, below.

TABLE 5

Tensile moduli, breaking strain and swelling ratio of DHD polyurethane materials with different component.

| Sample | Tensile Modulus, MPa | Tensile Strain, % | Swelling ratio, % |
|---|---|---|---|
| DHD-0 | 1.75 | 71.94 | 14.42 |
| DHD-25 | 1.95 | 41.46 | 15.80 |
| DHD-50 | 4.69 | 159.49 | 14.95 |
| DHD-75 | 2.25 | 105.92 | 9.60 |
| DHD-100 | 7.42 | 127.00 | 8.50 |

The study results demonstrated that DHD-0, DHD-25 and DHD-50 had a higher swelling ratio than that of DHD-75 and DHD-100. Furthermore, after hydrolysis, the size of each samples remained the same, thereby providing utility for a biomaterial that needs to remain its shape. This study indicated that the swelling ratio of DHD PU materials was tunable by adjusting the feed ratio of polyols and crosslinkers.

Mechanical Properties

Tunable mechanical properties are highly desired for biomaterials, due to the wide range of biomedical applications. Although all the samples displayed good mechanical properties, DHD-25 and DHD-75 demonstrated relatively low compression stress, as compared to DHD-0, DHD-50 and DHD-100. Under certain stress, DHD-25 and DHD-75 showed higher strain, corresponding to higher elasticity. Without intending to be bound by theory, this may be due to the microphase separation between soft and hard domains. In the tensile test, DHD-50 and DHD-100 displayed relatively high tensile breaking stress and elongation than DHD-0, DHD-25 and DHD-75, which was presumably attributed to good interfacial strength between soft and hard domains.

Protein Adsorption

To evaluate the anti-fouling properties of the PU, the protein adsorption on the DHD PU with different component were tested. The PHG-50 PU materials (PEG:glycerol:HDI=50:50:100) was used as control. The fluorescence images for protein adsorption of DHD PU with different component were obtained. Among all samples, PHG-50 sample displayed the highest fluorescence intensity, which indicated the highest protein adsorption. Compared to PHG-50, the protein adsorption on the surface of DHD-0, DHD-25, DHD-50, DHD-75 and DHD-100 were 0.42%, 1.26%, 1.97%, 0.75% and 2.16%, respectively. This study indicated that the DHD PU polymers possess highly capability to resist protein adsorption.

Cell Attachment

To further determine the anti-fouling properties of DHD PU, cell adhesion studies were carried on with NIH-3T3 fibroblast cells. After incubation at 37° C. for 24 hours, the tissue culture polystyrene (TCPS) surface displayed a full coverage of cells, which was used as control. The cell densities on surfaces of TCPS and control PHG-50 were $(57.51\pm2.06)\times10^5$ cells/cm$^2$ and $(63.55\pm1.83)\times10^4$ cells/cm$^2$, respectively. There was no observable cell on the surface of DHD-0, DHD-25, DHD-50, DHD-75, or DHD-100. These results indicated that the zwitterionic polyurethane biomaterials were successfully designed and synthesized to resist cell adhesion, which makes them potential candidate for implanted biomedical device.

Bacterial Attachment and Biofilm Formation

Bacterial attachment studies were carried on the surfaces of DHD PU using *P. aeruginosa* POA1 as a model and PHG-50 as control. The fluorescence images for bacterial attachment of DHD PU surfaces were obtained. The bacterial density on the surface of control PHG-50 was $(22.09\pm2.18)\times10^5$ cells/cm$^2$. There was no bacterial cell observed on the surface of any of the DHD PU biomaterials. These results demonstrated an excellent antifouling surface of DHD PU.

To further confirm the ability of DHD PU surface to resist biofilm formation, the *P. aeruginosa* POA1 were incubated on the surfaces of DHD PU and control PHG-50 under 25° C. for two weeks. After two weeks, PHG-50 demonstrated a full coverage of biofilm, while there was not even bacterial attached to the surfaces of DHD PU over the same amount of time.

Combined with the protein adsorption and cell adhesion results, these data indicate the DHD PU containing CB moieties are capable of remarkably improving the antifouling properties, which makes these materials a promising candidate for implantable biomedical devices.

Accordingly, Example 3 demonstrates that a series of zwitterionic DHD PUs were synthesized with different CB feed ratio resulting in adjustable mechanical properties and swelling ratio. TGA and DSC studies indicated the polyurethanes were thermally stable. The DHD PUs with DEAEA and DEAHA components exhibited a dramatically reduction on protein adsorption, cell attachment, bacterial adhesion and biofilm formation. Therefore, the polyurethane with both tunable surface and bulk properties has been achieved in one single material and their excellent potential in tailoring polymer structures to achieve desired functions to suit a variety of applications.

Aspects—Set One

Aspect 1. A polymer, comprising:
a polymer backbone comprising a first monomeric unit and one or more second monomeric units, wherein the one or more second monomeric units comprise a zwitterionic precursor monomeric unit having a structure according to one or more of Formula (A1), (B1), (C1), (D1), and (E1):

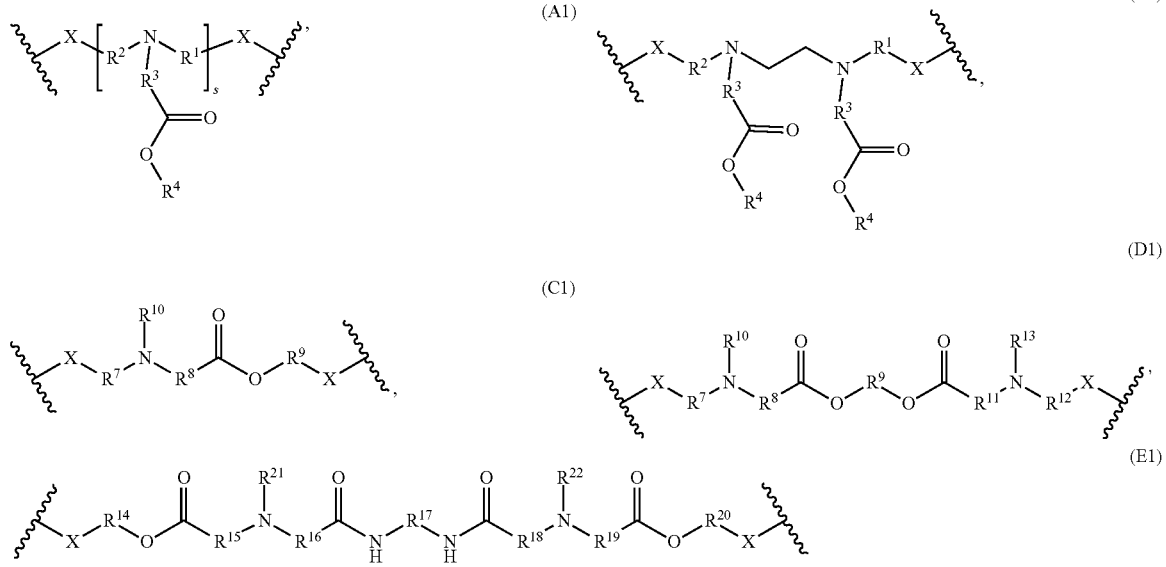

wherein in Formulas (A1) and (B1):
each X is independently O, NR$^a$, S or Se; and,
each R$^1$, R$^2$, and R$^3$ is independently selected from
—(CH$_2$)$_n$—, —(CH$_2$)$_n$O(CH$_2$)$_m$—,
—(CH$_2$CH$_2$OCH$_2$CH$_2$)$_n$—, —(CH$_2$CH$_2$O)$_n$CH$_2$CH$_2$—, —((CH$_2$)$_{1-8}$C(O)O)$_n$(CH$_2$)$_m$—,
—((CH$_2$)$_{1-8}$C(O)O)$_n$(CH$_2$CH$_2$O)$_m$(OC(O)(CH$_2$)$_{1-8}$)$_p$—, —((CH$_2$)$_{1-8}$C(O)O)$_n$(CH$_2$CH$_2$)$_m$(OC(O)(CH$_2$)$_{1-8}$)$_p$—, —(CH$_2$C(O)O)$_m$(CH$_2$CH$_2$)$_n$(OC(O)CH$_2$)$_m$—, —(CH(CH$_3$)C(O)O)$_m$(CH$_2$CH$_2$)$_n$(OC(O)CH(CH$_3$))$_m$—, —((CH$_2$)$_n$OC(O)O)(CH$_2$CH$_2$)$_m$,
—(CH$_2$)$_n$NHC(O)(CH$_2$)$_m$—, and —(CH$_2$)$_n$C(O)NH(CH$_2$)$_m$;
each R$^a$ and R$^4$ is independently selected from —H,
—(CH$_2$CH$_2$O)$_n$CH$_3$, —(CH$_2$CH$_2$O)$_n$(CH$_2$)$_m$CH$_3$,
—(CH$_2$CH$_2$O)$_n$(CH$_2$)$_m$OH, —((CH$_2$)$_n$O)$_m$((CH$_2$)$_p$O)$_q$(CH$_2$)$_r$OH, —(CH$_2$CH$_2$O)$_n$H, —(CH$_2$)$_n$OH,
—(CH$_2$)$_n$O(CH$_2$)$_m$OH, —(CH$_2$CH$_2$OCH$_2$CH$_2$)$_n$OH,
—(CH$_2$CH$_2$O)$_n$CH$_2$CH$_2$OH, —((CH$_2$)$_{1-8}$C(O)O)$_n$(CH$_2$)$_m$OH, —((CH$_2$)$_{1-8}$C(O)O)$_n$(CH$_2$CH$_2$O)$_m$(OC(O)(CH$_2$)$_{1-8}$)$_p$OH, —((CH$_2$)$_{1-8}$C(O)O)$_n$(CH$_2$CH$_2$)$_m$(OC(O)(CH$_2$)$_{1-8}$)$_m$OH, —(CH$_2$C(O)O)$_n$(CH$_2$CH$_2$)$_m$(OC(O)CH$_2$)$_p$OH, —(CH(CH$_3$)C(O)O)$_n$(CH$_2$CH$_2$)$_m$(OC(O)CH(CH$_3$))$_p$OH, —((CH$_2$)$_n$OC(O)O)(CH$_2$ $CH_2)_mOH$, $-(CH_2)_nNHC(O)(CH_2)_mOH$, and $-(CH_2)_nC(O)NH(CH_2)_mOH$, $C_{1-n}$ alkyl, $C_{1-n}$ alkenyl, $C_{1-n}$ alkynyl, $C_{6-10}$ aryl, and succinimidyl, wherein any one or more H atom of $R^a$ or $R^4$ can optionally be replaced with an F atom; and each n, m, p, q, r, and s is independently 1 to 10,000; wherein in Formulas (C1), (D1), and (E1)

each X is independently O, $NR^a$, S, or Se;

each $R^7$, $R^8$, $R^9$, $R^{11}$, $R^{12}$, $R^{14}$, $R^{15}$, $R^{16}$, $R^{17}$, $R^{18}$, $R^{19}$ and $R^{20}$ is independently selected from $-(CH_2)_n-$, $-((CH_2)_nO)_m((CH_2)_pO)_q(CH_2)_r$, $-(CH_2)_nO(CH_2)_m-$, $-(CH_2CH_2OCH_2CH_2)_n-$, $-(CH_2CH_2O)_nCH_2CH_2-$, $-((CH_2)_{1-8}C(O)O)_m(CH_2)_n$, $-((CH_2)_{1-8}C(O)O)_m(CH_2CH_2O)_n(OC(O)(CH_2)_{1-8})_p-$, $-((CH_2)_{1-8}C(O)O)_m(CH_2CH_2)_n(OC(O)(CH_2)_{1-8})_p-$, $-(CH_2C(O)O)_m(CH_2CH_2)_n(OC(O)CH_2)_p-$, $-(CH(CH_3)C(O)O)_m(CH_2CH_2)_n(OC(O)CH(CH_3))_p-$, $-(CH(CH_3)C(O)O)_m(CH_2CH_2)_n(OC(O)CH(CH_3))_p-$, $-((CH_2)_nOC(O)O)(CH_2CH_2)_m-$, $-(CH_2)_nNHC(O)(CH_2)_m-$, and $-(CH_2)_nC(O)NH(CH_2)_m-$;

each $R^a$, $R^{10}$, $R^{13}$, $R^{21}$, and $R^{22}$ is independently —H, $-(CH_2CH_2O)_nCH_3$, $-(CH_2CH_2O)_n(CH_2)_mCH_3$, $-(CH_2CH_2O)_n(CH_2)_mOH$, $-((CH_2)_nO)_m((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-(CH_2CH_2OCH_2CH_2)_nOH$, $-((CH_2)_{1-8}C(O)O)_n(CH2)_mOH$, $-((CH_2)_{1-8}C(O)O)_n(CH_2CH_2O)_m(OC(O)(CH_2)_{1-8})_pOH$, $-((CH_2)_{1-8}C(O)O)_n(CH_2CH_2)_m(OC(O)(CH_2)_{1-8})_pOH$, $-(CH_2C(O)O)_n(CH_2CH_2)_m(OC(O)CH_2)_pOH$, $-(CH(CH_3)C(O)O)_n(CH_2CH_2)_m(OC(O)CH(CH_3))_pOH$, $-(CH(CH_3)C(O)O)_n(CH_2CH_2)_m(OC(O)CH(CH_3))_pOH$, $-((CH_2)_nOC(O)O)(CH_2CH_2)_mOH$, $-(CH_2)_nNHC(O)(CH_2)_mOH$, $-(CH_2)_nC(O)NH(CH_2)_mOH$, $C_{1-n}$ alkyl, $C_{1-n}$ alkenyl, $C_{1-n}$ alkynyl, or $C_{6-10}$ aryl, wherein any one or more H atoms of $R^a$, $R^{10}$, $R^{13}$, $R^{21}$, or $R^{22}$ can optionally be replaced with an F atom; and, each n, m, p, q and r is independently 1 to 10,000.

Aspect 2. The polymer of aspect 1, wherein the polymer backbone comprises two or more second monomeric units, each of the second monomeric units being independently selected from Formulas (A1), (B1), (C1), (D1), and (E1) and are different than the second monomeric unit.

Aspect 3. The polymer of aspect 1, wherein the first monomeric unit is derived from a compound selected from the group consisting of an isocyanate, a diol, a polyol, and any combination thereof.

Aspect 4. A polymer comprising:
a polymer backbone comprising:
a first monomeric unit derived from a compound selected from the group consisting of an isocyanate, a diol, a polyol, and any combination thereof, and
one or more second monomeric units, the one or more second monomeric units comprising a zwitterionic precursor monomeric unit, wherein the zwitterionic precursor monomeric unit comprises a secondary or a tertiary amine within the polymer backbone.

Aspect 5. The polymer of aspect 3 or 4, wherein the isocyanate comprises a diisocyanate and/or a polyisocyanate.

Aspect 6. The polymer of any one of aspects 3-5, wherein the isocyanate is selected from the group consisting of isocyanate, isocyanate PEG, 4,4-methylenebis(phenyl isocyanate), 4,4-methylenebis(cyclohexyl isocyanate), 4,4'-oxybis(phenyl isocyanate), 3arm-PEG-isocyanate, 4arm-PEG-isocyanate, bis(4-isocyanatophenyl)methane, 4,4'-methylenebis(2-chlorophenyl isocyanate), 3,3'-dichloro-4, 4'-diisocyanato-1,1'-biphenyl, hexamethylene diisocyanate (HDI), 1,4-phenylene diisocyanate, 1,3-phenylene diisocyanate, m-xylylene diisocyanate, tolylene-2,4-diisocyanate, tolylene-2,6-diisocyanate, poly(hexamethylene diisocyanate), trans-1,4-cyclohexylene diisocyanate, 4-chloro-6-methyl-1,3-phenylene diisocyanate, 1,4-diisocyanatobutane, 1,8-diisocyanatooctane, 1,3-bis(1-isocyanato-1-methylethyl)benzene, 3,3'-dimethyl-4,4'-biphenylene diisocyanate, 1,12-diisocyanatododecane, polyisocyanate, and any combination thereof.

Aspect 7. The polymer of any one of aspects 3-6, wherein the isocyanate comprises hexamethylene diisocyanate (HDI).

Aspect 8. The polymer of any one of aspects 3-7, wherein the diol or polyol comprises poly(ethylene glycol) (PEG), ethylene glycol, diethylene glycol, triethylene glycol, tetraethylene glycol, propylene glycol, dipropylene glycol, tripropylene glycol, 1,3-propanediol, 1,3-butanediol, 1,4-butanediol, neopentyl glycol, 1,6-hexanediol, 1,4-cyclohexanedimethanol, trimethylolpropane, 1,2,6-hexanetriol, triethanolamine, pentaerythritol, glycerol, N,N,N',N'-tetrakis (2-hydroxypropyl)ethylenediamine, polytetrahydrofuran (PTHF) diol, polytetrahydrofuran (PTHF) triol, polycaprolactone (PCL) diol, polycaprolactone (PCL) triol, polycaprolactone (PCL) polyol, polydimethylsiloxane (PDMS) diol, polydimethylsiloxane (PDMS) triol, polydimethylsiloxane (PDMS) polyol, polyester diol, polyester triol, polylactide (PLA) diol, polylactide (PLA) triol, polypeptides, polyester, polyether, polyamide, octanediol, fluoroalkane polyol, fluoroalkene polyol, fluoroalkyne polyol, alkane polyol, alkene polyol, alkyne polyol, aromatic polyol, poly (vinyl alcohol), polysaccharide, poly(2-hydroxyethyl methacrylate) (pHEMA), poly(2-hydroxyethyl acrylate), poly (N—Hydroxyethyl acrylamide), poly(N-(Hydroxymethyl) acrylamide), poly(N-tris(hydroxymethyl) methylacrylamide), poly((methyl)acrylate) polyol, poly ((methyl)acrylamide) polyol, poly(polytetrahydrofuran carbonate) diol, polycarbonate diol, polycarbonate polyol, or any combination thereof.

Aspect 9. The polymer of aspect 8, wherein the poly (ethylene glycol) has a molecular weight ranging from about 200 Da to about 10,000 Da, about 200 Da to about 5000 Da, about 200 Da to about 1000 Da, or about 1000 Da to about 5000 Da.

Aspect 10. The polymer of anyone of the preceding aspects, wherein the polymer is non-degradable.

Aspect 11. The polymer of aspect 4, wherein the zwitterionic precursor monomeric unit has a structure according to Formula (A1) or (B1):

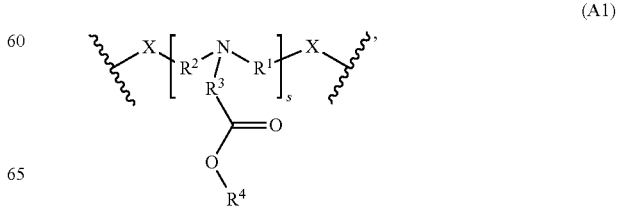

(A1)

-continued

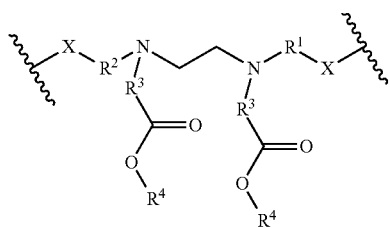
(B1)

wherein in Formula (A1) and (B1):
each X is independently O, NR$^a$, S or Se; and,
each R$^1$, R$^2$, and R$^3$ is independently selected from —(CH$_2$)$_n$—, —(CH$_2$)$_n$O(CH$_2$)$_m$—, —(CH$_2$CH$_2$OCH$_2$CH$_2$)$_n$—, —(CH$_2$CH$_2$O)$_n$CH$_2$CH$_2$—, —((CH$_2$)$_{1-8}$C(O)O)$_n$(CH$_2$)$_m$—, —((CH$_2$)$_{1-8}$C(O)O)$_n$(CH$_2$CH$_2$O)$_m$(OC(O)(CH$_2$)$_{1-8}$)$_p$—, —((CH$_2$)$_{1-8}$C(O)O)$_n$(CH$_2$CH$_2$)$_m$(OC(O)(CH$_2$)$_{1-8}$)$_p$—, —(CH$_2$C(O)O)$_m$(CH$_2$CH$_2$)$_n$(OC(O)CH$_2$)$_m$—, —(CH(CH$_3$)C(O)O)$_m$(CH$_2$CH$_2$)$_n$(OC(O)CH(CH$_3$))$_m$—, —(CH(CH$_3$)C(O)O)$_m$(CH$_2$CH$_2$)$_n$(OC(O)CH(CH$_3$))$_m$—, —((CH$_2$)$_n$OC(O)O)(CH$_2$CH$_2$)$_m$—, —(CH$_2$)$_n$NHC(O)(CH$_2$)$_m$—, and —(CH$_2$)$_n$C(O)NH(CH$_2$)$_m$—;
each R$^a$ and R$^4$ is independently selected from —H, —(CH$_2$CH$_2$O)$_n$CH$_3$, —(CH$_2$CH$_2$O)$_n$(CH$_2$)$_m$CH$_3$, —(CH$_2$CH$_2$O)$_n$(CH$_2$)$_m$OH, —((CH$_2$)$_n$O)$_m$((CH$_2$)$_p$O)$_q$(CH$_2$)$_r$OH, —(CH$_2$CH$_2$O)$_n$H, —(CH$_2$)$_n$OH, —(CH$_2$)$_n$O(CH$_2$)$_m$OH, —(CH$_2$CH$_2$OCH$_2$CH$_2$)$_n$OH, —(CH$_2$CH$_2$O)$_n$CH$_2$CH$_2$H, —((CH$_2$)$_{1-8}$C(O)O)$_n$(CH$_2$)$_m$OH, —((CH$_2$)$_{1-8}$C(O)O)$_n$(CH$_2$CH$_2$O)$_m$(OC(O)(CH$_2$)$_{1-8}$)$_p$OH, —((CH$_2$)$_{1-8}$C(O)O)$_n$(CH$_2$CH$_2$)$_m$(OC(O)(CH$_2$)$_{1-8}$)$_m$OH, —(CH$_2$C(O)O)$_n$(CH$_2$CH$_2$)$_m$(OC(O)CH$_2$)$_p$OH, —(CH(CH$_3$)C(O)O)$_n$(CH$_2$CH$_2$)$_m$(OC(O)CH(CH$_3$))$_p$OH, —((CH$_2$)$_n$OC(O)O)(CH$_2$CH$_2$)$_m$OH, —(CH$_2$)$_n$NHC(O)(CH$_2$)$_m$OH, and —(CH$_2$)$_n$C(O)NH(CH$_2$)$_m$OH, C$_{1-n}$ alkyl, C$_{1-n}$ alkenyl, C$_{1-n}$ alkynyl, C$_{6-10}$ aryl, and succinimidyl, wherein any one or more H atom of R$^a$ or R$^4$ can optionally be replaced with an F atom; and
each n, m, p, q, r, and s is independently 1 to 10,000.

Aspect 12. The polymer of any one of aspect 1 to 3 and 11, wherein the zwitterionic precursor monomeric unit has a structure:

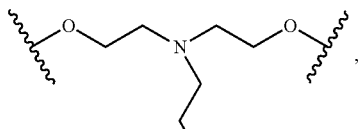

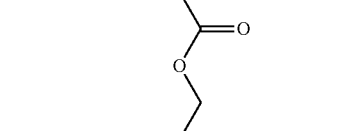

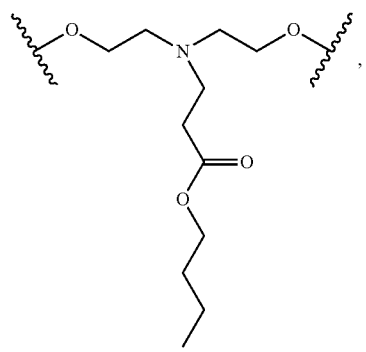

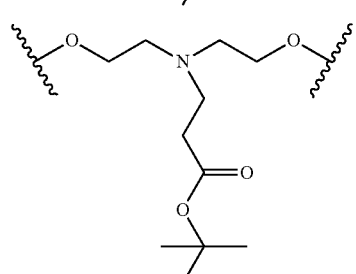

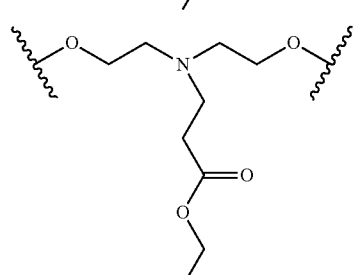

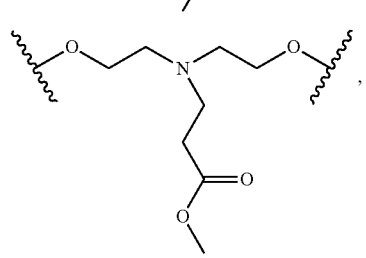

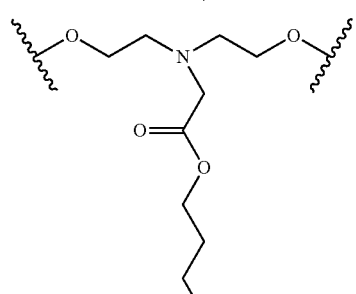

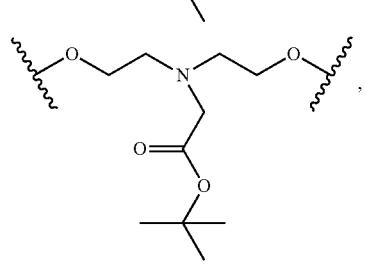

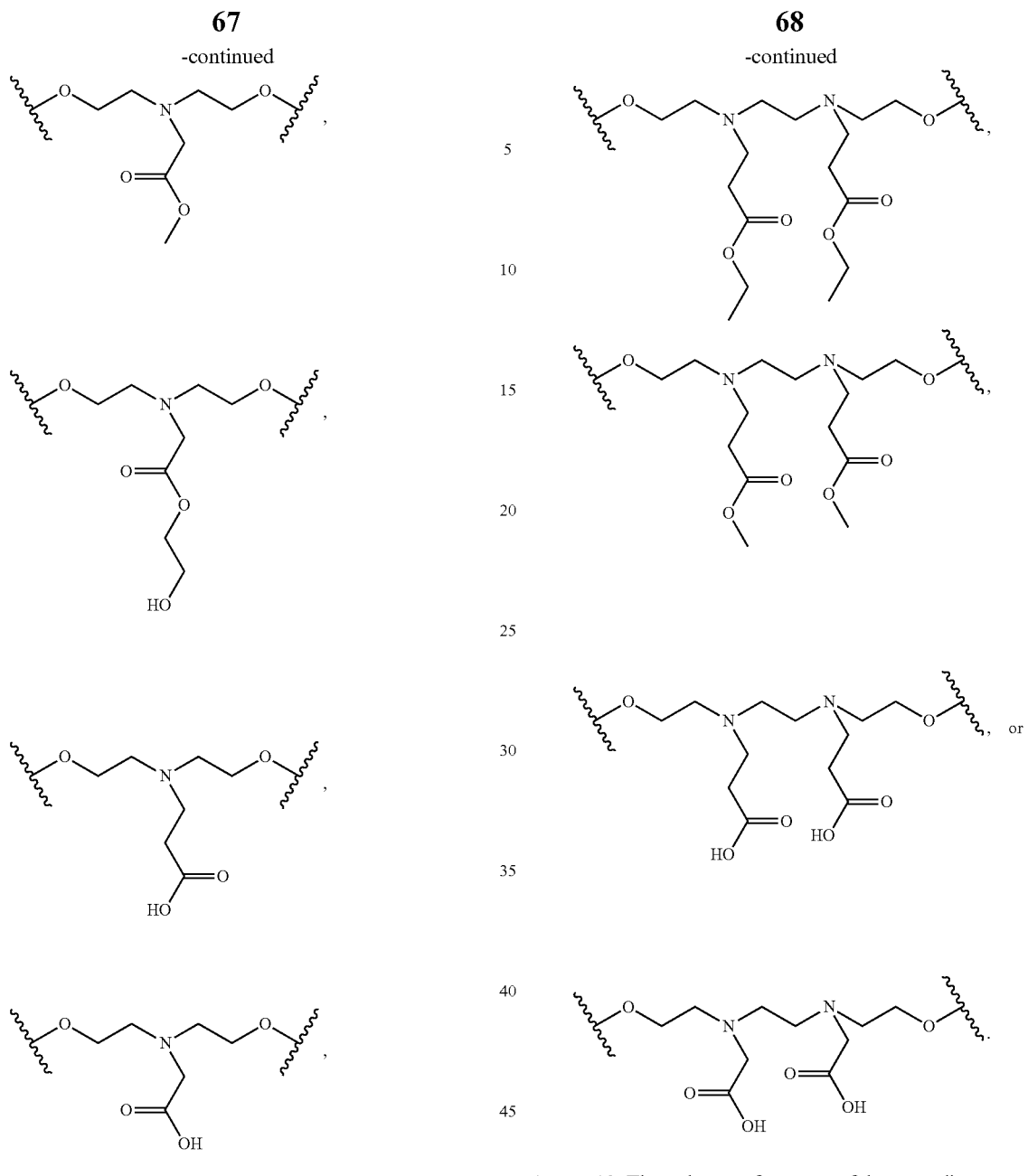
Aspect 13. The polymer of any one of the preceding aspects, wherein the polymer backbone comprises repeating units of Formula (I):
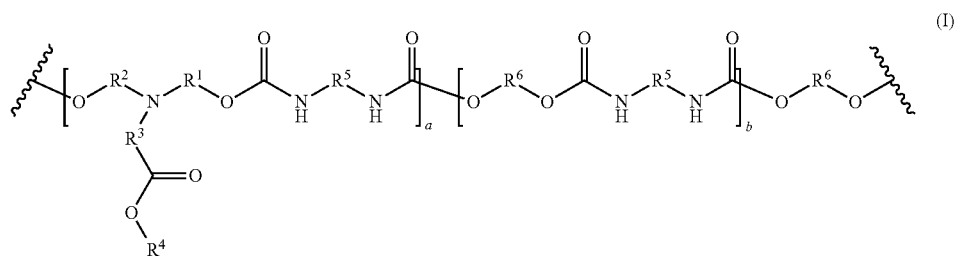

wherein $R^3$ is $—(CH_2)_{1-5}—$;

each of $R^5$ and $R^6$ is independently $—(CH_2)_n—$, $—(CH_2)_nO(CH_2)_m—$, $—(CH_2CH_2OCH_2CH_2)_n—$, $—(CH_2CH_2O)_nCH_2CH_2—$, $—(CH_2CH_2O)_n(CH_2)_m—$, $—(CH_2)_n(CH_2CH_2O)_n(CH_2)_p—$, $—((CH_2)_{1-8}C(O)O)_n(CH_2)_m—$, $—((CH_2)_{1-8}C(O)O)_n(CH_2CH_2O)_m(OC(O)(CH_2)_{1-8})_p—$, $—((CH_2)_{1-8}C(O)O)_n(CH_2CH_2)_m(OC(O)(CH_2)_{1-8})_p—$, $—(CH_2C(O)O)_n(CH_2CH_2)_m(OC(O)CH_2)_p—$, $—(CH(CH_3)C(O)O)_n(CH_2CH_2)_m(OC(O)CH(CH_3))_p—$, $—(CH(CH_3)C(O)O)_n(CH_2CH_2)_m(OC(O)CH(CH_3))_p—$, $—((CH_2)_nOC(O)O)(CH_2CH_2)_m—$, $—(CH_2)_nNHC(O)(CH_2)_m—$, $—(CH_2)_nC(O)NH(CH_2)_m—$, or $—(CH_2)_nCH(OH)(CH_2)_m—$;

a is 1 to 100,000; and, b is 0 to 100,000.

Aspect 14. The polymer of aspect 13, wherein $R^6$ is $—(CH_2CH_2O)_nCH_2CH_2—$.

Aspect 15. The polymer of aspect 13, wherein $R^6$ is $—(CH_2)_nCH(OH)(CH_2)_m—$.

Aspect 16. The polymer of aspect 15, wherein $R^6$ is $—(CH_2)CH(OH)(CH_2)—$.

Aspect 17. The polymer of any one of aspects 1-12, wherein the polymer backbone comprises repeating units of Formula (II):

(II)

[Chemical structure of Formula (II)]

wherein $R^5$ is $—(CH_2)_n—$, $—(CH_2)_nO(CH_2)_m—$, $—(CH_2CH_2OCH_2CH_2)_n—$, $—(CH_2CH_2O)_nCH_2CH_2—$, $—(CH_2CH_2)_n(CH_2)_m—$, $—(CH_2)_n(CH_2CH_2O)_n(CH_2)_p—$, $—((CH_2)_{1-8}C(O)O)_n(CH_2)_m—$, $—((CH_2)_{1-8}C(O)O)_n(CH_2CH_2O)_m(OC(O)(CH_2)_{1-8})_p—$, $—((CH_2)_{1-8}C(O)O)_n(CH_2CH_2)_m(OC(O)(CH_2)_{1-8})_p—$, $—(CH_2C(O)O)_n(CH_2CH_2)_m(OC(O)CH_2)_p—$, $—(CH(CH_3)C(O)O)_n(CH_2CH_2)_m(OC(O)CH(CH_3))_p—$, $—(CH(CH_3)C(O)O)_n(CH_2CH_2)_m(OC(O)CH(CH_3))_p—$, $—((CH_2)_nOC(O)O)(CH_2CH_2)_m—$, $—(CH_2)_nNHC(O)(CH_2)_m—$, $—(CH_2)_nC(O)NH(CH_2)_m—$, or $—(CH_2)_nCH(OH)(CH_2)_m—$.

Aspect 18. The polymer of any one of aspects 13-17, wherein $R^5$ is $—(CH_2)_6—$.

Aspect 19. The polymer of any one of aspects 13-18, wherein $R^4$ is $—(CH_2)_2OH$.

Aspect 20. The polymer of any one of aspects 13-18, wherein $R^4$ is $—CH_2CH_3$.

Aspect 21. The polymer of any one of aspects 1-13, wherein the polymer backbone comprises repeating units of Formula (III):

(III)

[Chemical structure of Formula (III)]

wherein x is 1 to 1,000,000.

Aspect 22. The polymer of aspect 21, wherein x is 1 to 100,000, 1 to 10,000, 1 to 1000, or 1 to 100.

Aspect 23. The polymer of any one of aspects 1-12, wherein the polymer backbone comprises repeating units of Formula (IV):

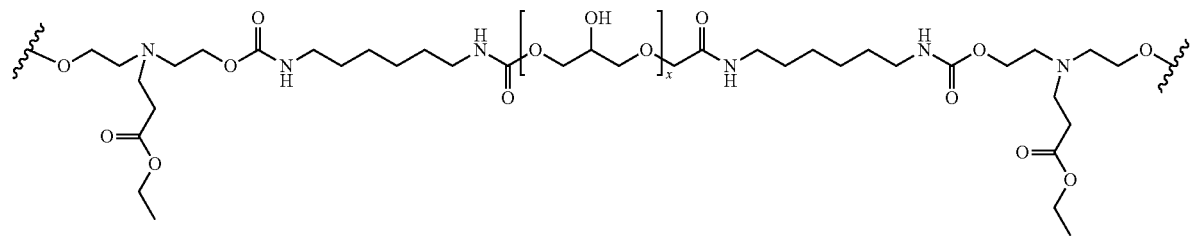

(IV)

wherein x is 1 to 1,000,000.

Aspect 24. The polymer of aspect 23, wherein x is 1 to 100,000, 1 to 10,000, 1 to 1000, or 1 to 100.

Aspect 25. The polymer of any one of aspects 1-12, wherein the polymer backbone comprises repeating units of Formula (V):

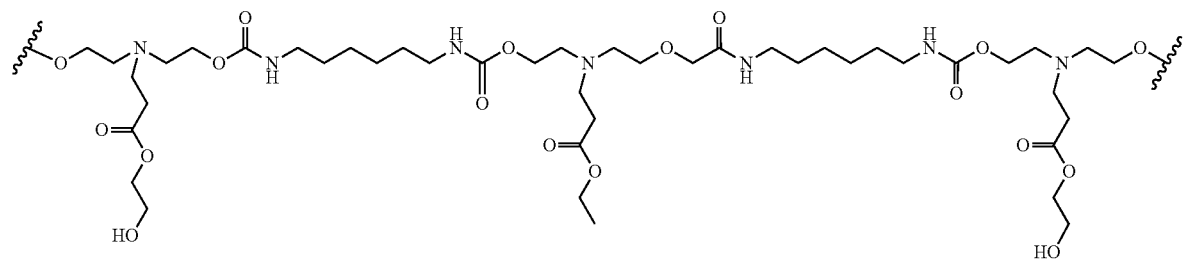

(V)

Aspect 26. The polymer of any one of aspects 1-12, wherein the polymer backbone comprises repeating units of Formula (VI):

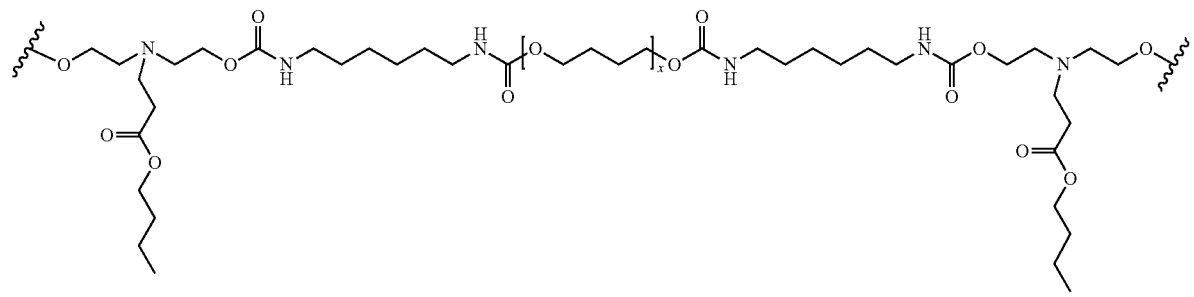

(VI)

wherein x is 1 to 1,000,000.

Aspect 27. The polymer of aspect 26, wherein x is 1 to 100,000, 1 to 10,000, 1 to 1000, or 1 to 100.

Aspect 28. The polymer of any one of aspects 1-12, wherein the polymer backbone comprises repeating units of Formula (VII):

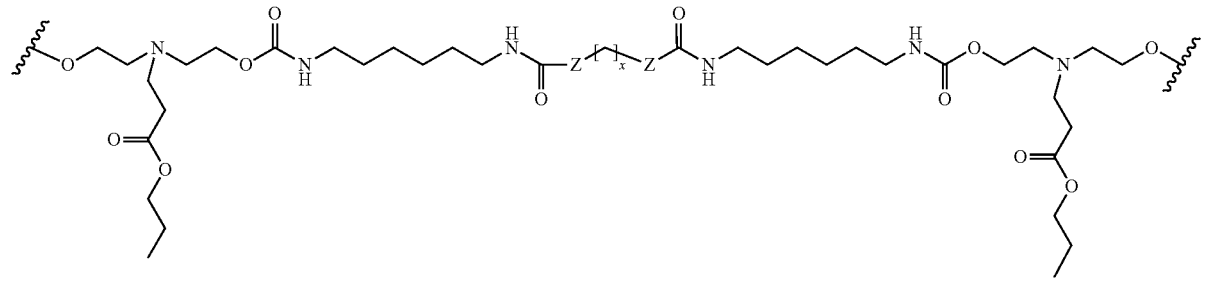

(VII)

wherein Z is O or NH, and x is 1 to 30.

Aspect 29. The polymer of any one of aspects 1-12, wherein the polymer backbone comprises repeating units of Formula Aspect 30. The polymer of any one of the preceding aspects, wherein the polymer is biodegradable.

Aspect 31. The polymer of any one of aspects 4 to 30, wherein the zwitterionic precursor monomeric unit has a structure according to Formula (C1), (D1), or (E1):

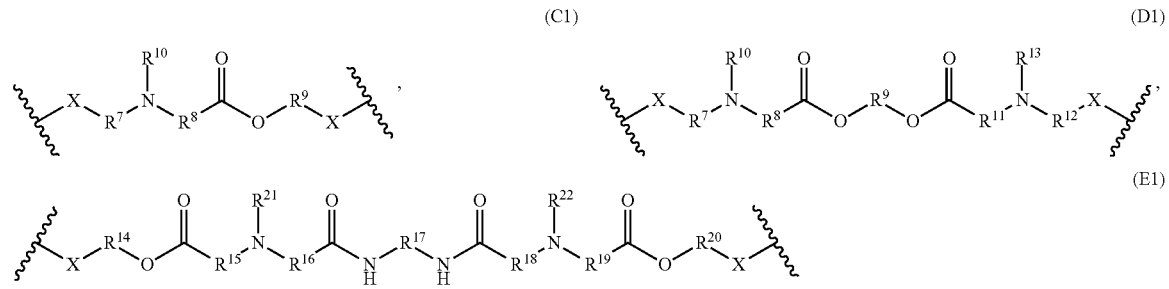

wherein:

each X is independently O, $NR^a$, S, or Se;

each $R^7$, $R^8$, $R^9$, $R^{11}$, $R^{12}$, $R^{14}$, $R^{15}$, $R^{16}$, $R^{17}$, $R^{18}$, $R^{19}$ and $R^{20}$ is independently selected from $-(CH_2)_n-$, $-((CH_2)_nO)_m((CH_2)_pO)_q(CH_2)_r-$, $-(CH_2)_nO(CH_2)_m-$, $-(CH_2CH_2OCH_2CH_2)_n-$, $-(CH_2CH_2O)_nCH_2CH_2-$, $-((CH_2)_{1-8}C(O)O)_m(CH_2)_n-$, $-((CH_2)_{1-8}C(O)O)_m$ $(CH_2CH_2)_n(OC(O)(CH_2)_{1-8})_p-$, $-((CH_2)_{1-8}C(O)O)_m$ $(CH_2CH_2)_n(OC(O)(CH_2)_{1-8})_p-$, $-(CH_2C(O)O)_m$ $(CH_2CH_2)_n(OC(O)CH_2)_p-$, $-(CH(CH_3)C(O)O)_m$ $(CH_2CH_2)_n(OC(O)CH(CH_3))_p-$, $-(CH(CH_3)C(O)O)_m$ $(CH_2CH_2)_n(OC(O)CH(CH_3))_p-$, $-((CH_2)_nOC(O)O)$ $(CH_2CH_2)_m-$, $-(CH_2)_nNHC(O)(CH_2)_m-$, and $-(CH_2)_nC(O)NH(CH_2)_m-$;

each $R^a$, $R^{10}$, $R^{13}$, $R^{21}$, and $R^{22}$ is independently —H, $-(CH_2CH_2O)_nCH_3$, $-(CH_2CH_2O)_n(CH_2)_mCH_3$, $-(CH_2CH_2O)_n(CH_2)_mOH$, $-((CH_2)_nO)_m((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-(CH_2CH_2OCH_2CH_2)_nOH$, $-((CH_2)_{1-8}C(O)O)_n(CH2)_mOH$, $-((CH_2)_{1-8}C(O)O)_n(CH_2CH_2O)_m(OC(O)(CH_2)_{1-8})_pOH$, $-((CH_2)_{1-8}C(O)O)_n(CH_2CH_2)_m(OC(O)(CH_2)_{1-8})_pOH$, $-(CH_2C(O)O)_n(CH_2CH_2)_m(OC(O)CH_2)_pOH$, $-(CH(CH_3)C(O)O)_n(CH_2CH_2)_m(OC(O)CH(CH_3))_pOH$, $-(CH(CH_3)C(O)O)_n(CH_2CH_2)_m(OC(O)CH(CH_3))_pOH$, $-((CH_2)_nOC(O)O)(CH_2CH_2)_mOH$, $-(CH_2)_nNHC(O)(CH_2)_mOH$, $-(CH_2)_nC(O)NH(CH_2)_mOH$, $C_{1-n}$ alkyl, $C_{1-n}$ alkenyl, $C_{1-n}$ alkynyl, or $C_{6-10}$ aryl, wherein any one or more H atoms of $R^a$, $R^{10}$, $R^{13}$, $R^{21}$, or $R^{22}$ can optionally be replaced with an F atom; and, each n, m, p, q and r is independently 1 to 10,000.

Aspect 32. The polymer of any one of aspects 1 to 3 and 31, wherein the zwitterionic precursor monomeric unit has a structure:

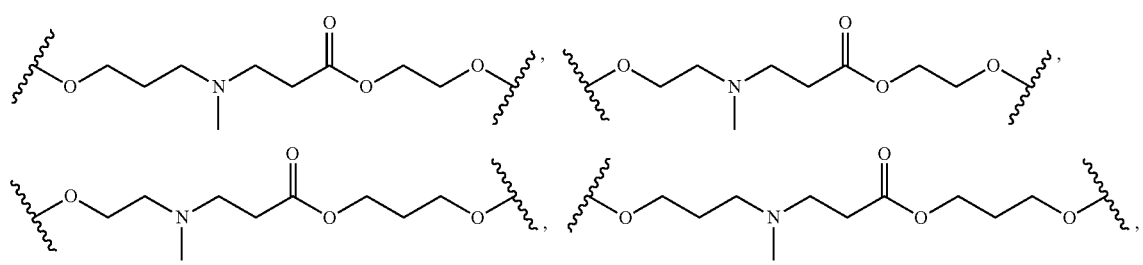

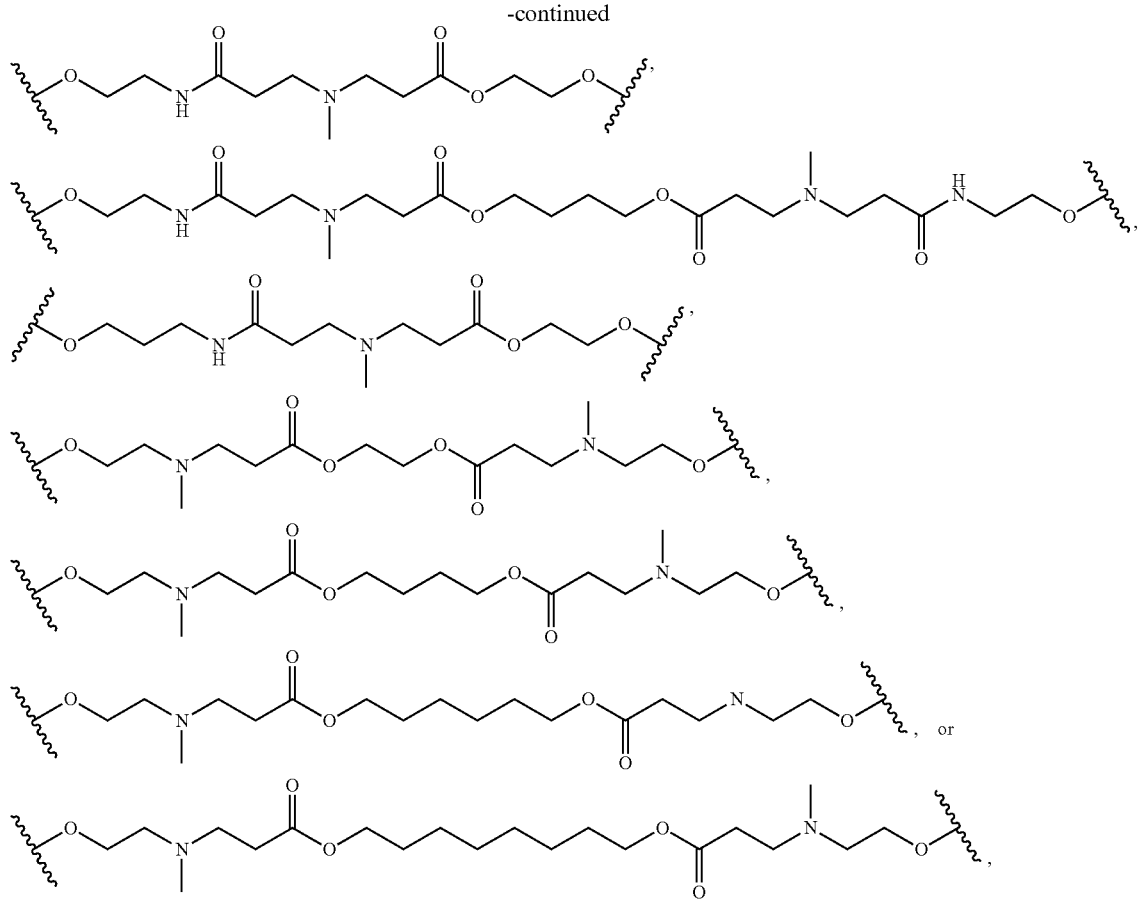

Aspect 33. The polymer of any one of the preceding aspects, wherein the polymer has a molecular weight ranging from about 1000 Da to about 10,000,000 Da, about 5000 Da to about 1,000,000 Da, about 10,000 to about 500,000, or about 100,000 Da to about 250,000 Da.

Aspect 34. The polymer of any one of aspects 1 to 3 and 11 to 31, wherein each n, m, p, q, r, and s is independently 1 to 5,000, 1 to 1000, 1 to 500, 1 to 100, or 1 to 10.

Aspect 35. The polymer of any one of the aspects 3 to 34, wherein the ratio of hydroxyl groups in the zwitterionic precursor monomeric unit:hydroxyl groups in the diol or polyol:isocyanate groups in the isocyanate ranges from about 1:9999:10,000 to about 10,000:0:10,000.

Aspect 36. The polymer of aspect 35, wherein the ratio is selected from the group consisting of 2:8:10, 4:6:10, 6:4:10, 8:2:10, and 10:0:10.

Aspect 37. The polymer of any one of the preceding aspects, wherein the polymer backbone further comprises a third monomeric unit derived from one or more of a urethane, urea, amide, ester, imide, and carbonate.

Aspect 38. The polymer of any one of the preceding aspects, wherein the polymer is hydrolyzed.

Aspect 39. An implantable medical device comprising the polymer of any one of the preceding aspects.

Aspect 40. A method of preparing a polymer, the method comprising:
admixing a diol or polyol with an isocyanate to form a prepolymer solution;
admixing the prepolymer solution with a zwitterionic precursor compound having a secondary or tertiary amine to form a modified prepolymer solution; and,
exposing the modified prepolymer solution to conditions sufficient to initiate polymerization, thereby forming a polymer having a polymer backbone,
wherein the secondary or tertiary amine of the zwitterionic precursor compound is within the polymer backbone.

Aspect 41. A method of preparing a polymer, the method comprising:
admixing a zwitterionic precursor compound having a secondary or tertiary amine with an isocyanate to form a prepolymer solution;
admixing the prepolymer solution with a diol, polyol, diamine, or polyamine to form a modified prepolymer solution; and,
exposing the modified prepolymer solution to conditions sufficient to initiate polymerization, thereby forming a polymer having a polymer backbone,
wherein the secondary or tertiary amine of the zwitterionic precursor compound is within the polymer backbone.

Aspect 42. A method of preparing a polymer, the method comprising:
admixing a zwitterionic precursor compound having a secondary or tertiary amine with an isocyanate and a diol or polyol to form a prepolymer solution;
exposing the prepolymer solution to conditions sufficient to initiate polymerization, thereby forming a polymer having a polymer backbone,
wherein the secondary or tertiary amine of the zwitterionic precursor compound is within the polymer backbone.

Aspect 43. The method of any one of aspects 40-42, wherein the isocyanate is selected from the group consisting of 4,4-methylenebis(phenyl isocyanate), 4,4-methylenebis(cyclohexyl isocyanate), 4,4'-oxybis(phenyl isocyanate), 4arm-PEG-isocyanate, bis(4-isocyanatophenyl)methane, 4,4'-methylenebis(2-chlorophenyl isocyanate), 3,3'-dichloro-4,4'-diisocyanato-1,1'-biphenyl, hexamethylene diisocyanate (HDI), 1,4-phenylene diisocyanate, 1,3-phenylene diisocyanate, m-xylylene diisocyanate, tolylene-2,4-diisocyanate, tolylene-2,6-diisocyanate, poly(hexamethylene diisocyanate), trans-1,4-cyclohexylene diisocyanate, 4-chloro-6-methyl-1,3-phenylene diisocyanate, 1,4-diisocyanatobutane, 1,8-diisocyanatooctane, 1,3-bis(1-isocyanato-1-methylethyl)benzene, 3,3'-dimethyl-4,4'-biphenylene diisocyanate, 1,12-diisocyanatododecane, and any combination thereof.

Aspect 44. The method of any one of aspects 40-43, wherein the isocyanate comprises hexamethylene diisocyanate (HDI).

Aspect 45. The method of any one of aspects 40-44, wherein the diol or polyol comprises poly(ethylene glycol) (PEG), ethylene glycol, diethylene glycol, triethylene glycol, tetraethylene glycol, propylene glycol, dipropylene glycol, tripropylene glycol, 1,3-propanediol, 1,3-butanediol, 1,4-butanediol, neopentyl glycol, 1,6-hexanediol, 1,4-cyclohexanedimethanol, trimethylolpropane, 1,2,6-hexanetriol, triethanolamine, pentaerythritol, glycerol, N,N,N',N'-tetrakis (2-hydroxypropyl)ethylenediamine, polytetrahydrofuran (PTHF) diol, polytetrahydrofuran (PTHF) triol, polycaprolactone (PCL) diol, polycaprolactone (PCL) triol, polycaprolactone (PCL) polyol, polydimethylsiloxane (PDMS) diol, polydimethylsiloxane (PDMS) triol, polydimethylsiloxane (PDMS) polyol, polyester diol, polyester triol, polylactide (PLA) diol, polylactide (PLA) triol, polypeptides, polyester, polyether, polyamide, octanediol, fluoroalkane polyol, alkane polyol, alkene polyol, alkyne polyol, aromatic polyol, poly(vinyl alcohol), polysaccharide, poly(2-hydroxyethyl methacrylate) (pHEMA), poly(2-hydroxyethyl acrylate), poly(N—Hydroxyethyl acrylamide), poly(N-(Hydroxymethyl)acrylamide), poly(N-tris(hydroxymethyl) methylacrylamide), poly((methyl)acrylate) polyol, poly((methyl)acrylamide) polyol, poly(polytetrahydrofuran carbonate) diol, polycarbonate diol, polycarbonate polyol, or any combination thereof.

Aspect 46. The method of any one of aspects 40-45, wherein the zwitterionic precursor compound has a structure according to Formula (A2) or (B2):

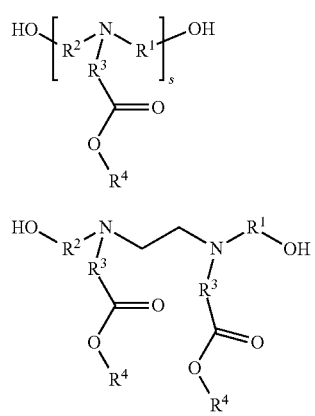

wherein:
each $R^1$, $R^2$, and $R^3$ is independently selected from —$(CH_2)_n$—, —$(CH_2)_nO(CH_2)_m$—, —$(CH_2CH_2OCH_2CH_2)_n$—, —$(CH_2CH_2O)_nCH_2CH_2$—, —$((CH_2)_{1-8}C(O)O)_n(CH_2)_m$—, —$((CH_2)_{1-8}C(O)O)_n(CH_2CH_2O)_m(OC(O)(CH_2)_{1-8})_p$—, —$((CH_2)_{1-8}C(O)O)_n(CH_2CH_2)_m(OC(O)(CH_2)_{1-8})_p$—, —$(CH_2C(O)O)_m(CH_2CH_2)_n(OC(O)CH_2)_m$—, —$(CH(CH_3)C(O)O)_m(CH_2CH_2)_n(OC(O)CH(CH_3))_m$—, —$(CH(CH_3)C(O)O)_m(CH_2CH_2)_n(OC(O)CH(CH_3))_m$—, —$((CH_2)_nOC(O)O)(CH_2CH_2)_m$—, —$(CH_2)_nNHC(O)(CH_2)_m$—, and —$(CH_2)_nC(O)NH(CH_2)_m$—;

each $R^4$ is independently selected from —H, —$(CH_2CH_2O)_nCH_3$, —$(CH_2CH_2O)_n(CH_2)_mCH_3$, —$(CH_2CH_2O)_n(CH_2)_mOH$, —$((CH_2)_nO)_m((CH_2)_pO)_q(CH_2)_rOH$, —$(CH_2CH_2O)_nH$, —$(CH_2)_nOH$, —$(CH_2)_nO(CH_2)_mOH$, —$(CH_2CH_2OCH_2CH_2)_nOH$, —$(CH_2CH_2O)_nCH_2CH_2OH$, —$((CH_2)_{1-8}C(O)O)_n(CH_2)_mOH$, —$((CH_2)_{1-8}C(O)O)_n(CH_2CH_2O)_m(OC(O)(CH_2)_{1-8})_pOH$, —$((CH_2)_{1-8}C(O)O)_n(CH_2CH_2)_m(OC(O)(CH_2)_{1-8})_mOH$, —$(CH_2C(O)O)_n(CH_2CH_2)_m(OC(O)CH_2)_pOH$, —$(CH(CH_3)C(O)O)_n(CH_2CH_2)_m(OC(O)CH(CH_3))_pOH$, —$((CH_2)_nOC(O)O)(CH_2CH_2)_mOH$, —$(CH_2)_nNHC(O)(CH_2)_mOH$, and —$(CH_2)_nC(O)NH(CH_2)_mOH$, $C_{1-n}$ alkyl, $C_{1-n}$ alkenyl, $C_{1-n}$ alkynyl, $C_{6-10}$ aryl, and succinimidyl, wherein any one or more H atoms of $R^4$ can optionally be replaced with an F atom; and, each n, m, p, q, r, and s is independently 1 to 10,000.

Aspect 47. The method of aspect 46, wherein the zwitterionic precursor compound is selected from the group consisting of:

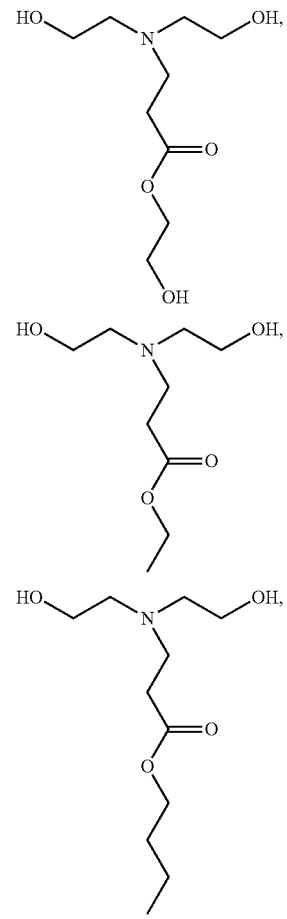

-continued
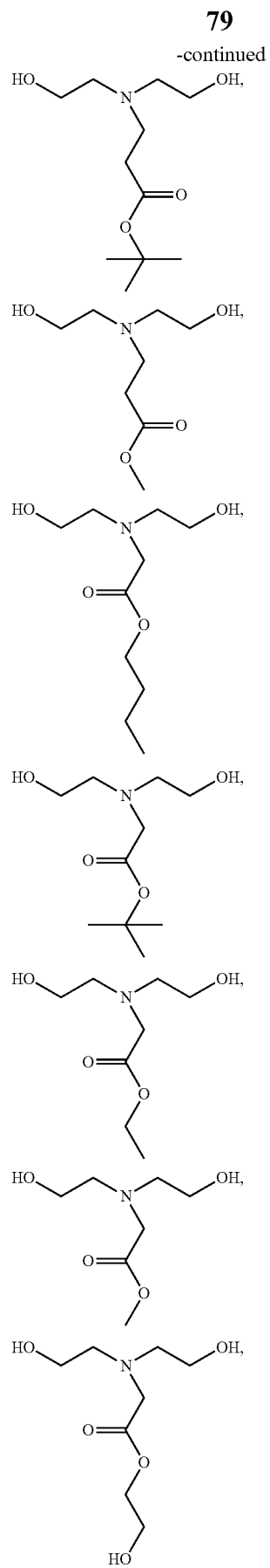
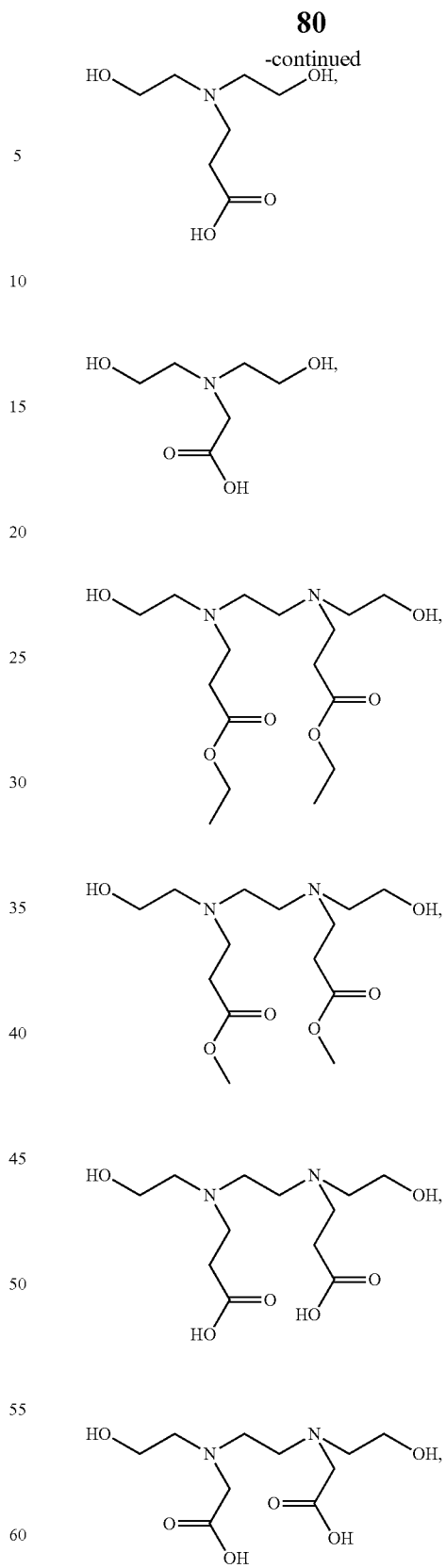
and combinations thereof.
Aspect 48. The method of any one of aspects 40-46, wherein the zwitterionic precursor compound has a structure according to Formula (B2), (C2), or (D2):

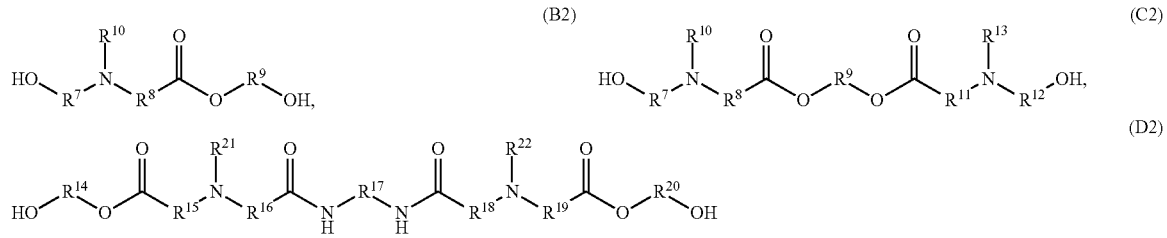

wherein:

each $R^7, R^8, R^9, R^{11}, R^{12}, R^{14}, R^{15}, R^{16}, R^{17}, R^{18}, R^{19}$ and $R^{20}$ is independently selected from —$(CH_2)_n$—, —$((CH_2)_nO)_m((CH_2)_pO)_q(CH_2)_r$, —$(CH_2)_nO(CH_2)_m$—, —$(CH_2CH_2OCH_2CH_2)_n$—, —$(CH_2CH_2O)_nCH_2CH_2$—, —$((CH_2)_{1-8}C(O)O)_m(CH_2)_n$—, —$((CH_2)_{1-8}C(O)O)_m(CH_2CH_2O)_n(OC(O)(CH_2)_{1-8})_p$—, —$((CH_2)_{1-8}C(O)O)_m(CH_2CH_2)_n(OC(O)(CH_2)_{1-8})_p$—, —$(CH_2C(O)O)_m(CH_2CH_2)_n(OC(O)CH_2)_p$—, —$(CH(CH_3)C(O)O)_m(CH_2CH_2)_n(OC(O)CH(CH_3))_p$—, —$(CH(CH_3)C(O)O)_m(CH_2CH_2)_n(OC(O)CH(CH_3))_p$—, —$((CH_2)_nOC(O)O)(CH_2CH_2)_m$—, —$(CH_2)_nNHC(O)(CH_2)_m$—, and —$(CH_2)_nC(O)NH(CH_2)_m$—;

each $R^{10}, R^{13}, R^{21},$ and $R^{22}$ is independently —H, —$(CH_2CH_2O)_nCH_3$, —$(CH_2CH_2O)_n(CH_2)_mCH_3$, —$(CH_2CH_2O)_n(CH_2)_mOH$, —$((CH_2)_nO)_m((CH_2)_pO)_q(CH_2)_rOH$, —$(CH_2CH_2O)_nH$, —$(CH_2)_nOH$, —$(CH_2)_nO(CH_2)_mOH$, —$(CH_2CH_2OCH_2CH_2)_nOH$, —$(CH_2CH_2O)_nCH_2CH_2OH$, —$(CH_2CH_2OCH_2CH_2)_nOH$, —$((CH_2)_{1-8}C(O)O)_n(CH2)_mOH$, —$((CH_2)_{1-8}C(O)O)_n(CH_2CH_2O)_m(OC(O)(CH_2)_{1-8})_pOH$, —$((CH_2)_{1-8}C(O)O)_n(CH_2CH_2)_m(OC(O)(CH_2)_{1-8})_pOH$, —$(CH_2C(O)O)_n(CH_2CH_2)_m(OC(O)CH_2)_pOH$, —$(CH(CH_3)C(O)O)_n(CH_2CH_2)_m(OC(O)CH(CH_3))_pOH$, —$(CH(CH_3)C(O)O)_n(CH_2CH_2)_m(OC(O)CH(CH_3))_pOH$, —$((CH_2)_nOC(O)O)(CH_2CH_2)_mOH$, —$(CH_2)_nNHC(O)(CH_2)_mOH$, —$(CH_2)_nC(O)NH(CH_2)_mOH$, $C_{1-n}$ alkyl, $C_{1-n}$ alkenyl, $C_{1-n}$ alkynyl, or $C_{6-10}$ aryl, wherein any one or more H atoms of $R^{10}, R^{13}, R^{21},$ or $R^{22}$ can optionally be replaced with an F atom; and, each n, m, p, q and r is independently 1 to 10,000.

Aspect 49. The method of aspect 48, wherein the zwitterionic precursor compound has a structure:

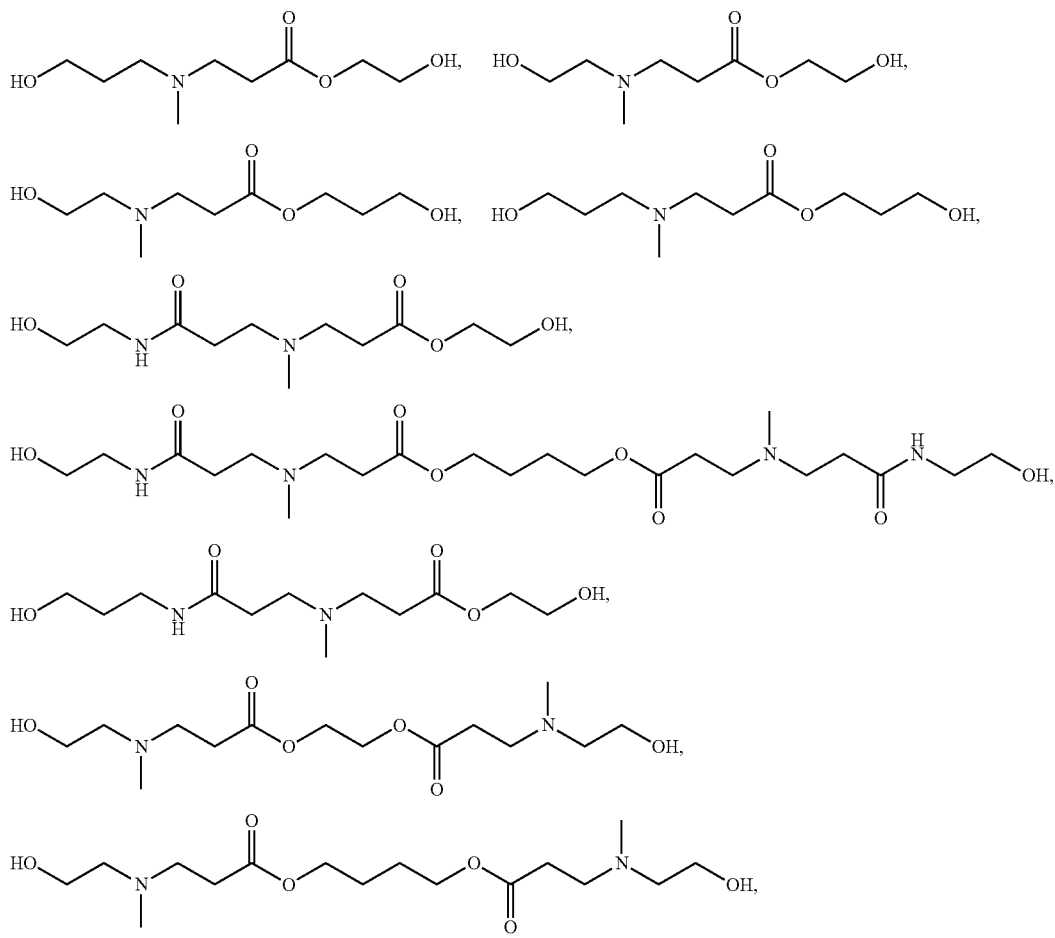

-continued

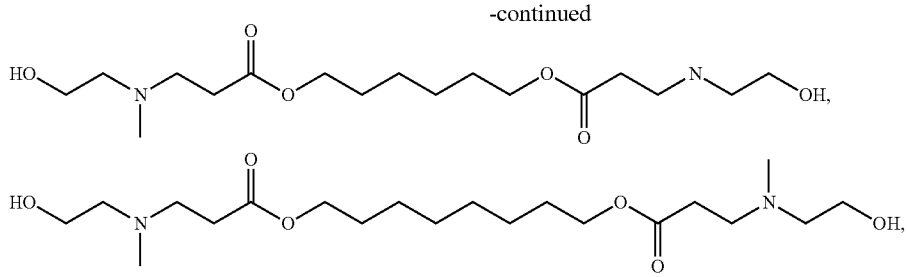

or any combination thereof.

Aspect 50. The method of any one of aspects 40-49, wherein each admixing step occurs at a temperature ranging from about 50° C. to about 100° C.

Aspect 51. The method of anyone of aspects 40-50, wherein the prepolymer solution and/or the modified prepolymer solution is substantially free of organic solvent.

Aspect 52. The method of any one of aspects 40-50, wherein the prepolymer solution and/or the modified prepolymer solution comprises an organic solvent.

Aspect 53. The method of aspect 52, wherein the organic solvent is selected from the group consisting of DMF, DMSO, DCM, chloroform, THF, and any combination thereof.

Aspect 54. The method of any one of aspects 40-53, wherein the diol or polyol comprises PEG, and the isocyanate comprises HDI.

Aspect 55. The method of any one of aspects 40-54, wherein the diol or polyol, the isocyanate, and the zwitterionic precursor compound are provided in amounts sufficient to provide a polymer having a ratio of hydroxyl groups in the zwitterionic precursor monomeric unit:hydroxyl groups in the diol or polyol:isocyanate groups in the isocyanate ranging from about 1:9999:10,000 to about 10,000:0:10,000.

Aspect 56. The method of aspect 55, wherein the ratio is selected from the group consisting of 2:8:10, 4:6:10, 6:4:10, 8:2:10, and 10:0:10.

Aspect 57. The method of any one of aspects 40, 41, and 43-56, wherein both admixing steps occur in the same reaction vessel.

Aspect 58. The method of any one of aspects 40-57, wherein the exposing step occurs at a temperature ranging from about 20° C. to about 200° C.

Aspect 59. The method of any one of aspects 40-58, wherein the exposing step occurs in the presence of a tertiary amine initiator.

Aspect 60. The method of aspect 59, wherein the tertiary amine initiator comprises 1,4-diazabicyclo[2.2.2]octane (DABCO).

Aspect 61. The method of any one of aspects 40-60, wherein the exposing step occurs in the presence of a metallic compound.

Aspect 62. The method of aspect 61, wherein the metallic compound comprises dibutyltin dilaurate or bismuth octanoate.

Aspect 63. The method of any one of aspects 40-62, wherein the exposing step occurs in the presence of ultraviolet (UV) light.

Aspect 64. The method of any one of aspects 40-63, further comprising hydrolyzing the polymer in an aqueous solution.

Aspect 65. The method of aspect 64, wherein the aqueous solution comprises deionized water.

Aspect 66. The method of aspect 64 or 65, wherein the hydrolyzing occurs at a temperature ranging from about 4° C. to about 99° C.

Aspect 67. The method of any one of aspects 64-66, wherein the hydrolyzing occurs at a pH value ranging from about 6 to about 14.

Aspect 68. The method of any one of aspects 64-67, wherein the aqueous solution is substantially free of added base.

Aspect 69. The method of aspect 68, wherein the aqueous solution is substantially free of NaOH and/or KOH.

Aspect 70. The method of any one of aspects 64-69, wherein the aqueous solution comprises an inorganic or tertiary amine organic base.

Aspects—Set Two

Aspect 1. A polyurethane composition having anti-fouling and antimicrobial properties comprising one or more zwitterionic precursor moieties chemically bonded to a polymer backbone, the polymer backbone comprising one or more monomers selected from the group consisting of polyisocyanates, diisocyanates, diols, polyols, and combinations thereof.

Aspect 2. The polyurethane composition of aspect 1, wherein the polyurethane has a molecular weight of about 1,000 to about 10,000,000 Dalton.

Aspect 3. The polyurethane composition of aspect 1, wherein said composition comprises a hydrogel.

Aspect 4. The polyurethane composition of aspect 1, wherein said composition comprises an elastomer.

Aspect 5. The polyurethane composition of aspect 1, wherein the zwitterionic compound precursor has the formula

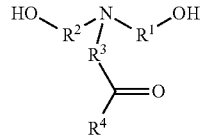

wherein $R^1$ is —$CH_2$—, —$CH_2CH_2$—, —$CH_2CH_2CH_2$—, —$CH_2CH_2CH_2CH_2$—, —$CH_2CH_2CH_2CH_2CH_2$—, —$(CH_2)_i$—, —$CH_2CH_2OCH_2CH_2$—, —$(CH_2)_jO(CH_2)_k$—, —$(CH_2CH_2OCH_2CH_2)_l$—, or —$(CH_2CH_2O)_fCH_2CH_2$—;
$R^2$—$CH_2$—, —$CH_2CH_2$—, —$CH_2CH_2CH_2$—, —$CH_2CH_2CH_2CH_2$—, —$CH_2CH_2CH_2CH_2CH_2$—, —$(CH_2)_m$—, —$CH_2CH_2OCH_2CH_2$—, —$(CH_2)_nO(CH_2)_o$—, or —$(CH_2CH_2OCH_2CH_2)_p$;
$R^3$ is —$CH_2$—, —$CH_2CH_2$—, —$CH_2CH_2CH_2$—, —$CH_2CH_2CH_2CH_2$—, —$CH_2CH_2CH_2CH_2CH_2$—, —$(CH_2)_q$—, —$CH_2CH_2OCH_2CH_2$—, —$(CH_2)_rO(CH_2)_s$—, —$(CH_2CH_2OCH_2CH_2)_t$, or —$(CH_2CH_2O)_uCH_2CH_2$—;

R4 is —CH₃, —CH₂CH₃, —CH₂CH₂CH₃, —CH₂CH₂CH₂CH₃, —CH₂CH₂CH₂CH₂CH₃, —(CH₂)ᵢCH₃, —CH₂CH₂OH, —CH₂CH₂CH₂OH, —CH₂CH₂CH₂CH₂OH, —CH₂CH₂CH₂CH₂CH₂OH, (CH₂)ᵥOH, —CH₂CH₂OCH₂CH₂OH, (CH₂)ᵥO(CH₂)ₓOH, —(CH₂CH₂OCH₂CH₂)ᵧOH, or —(CH₂CH₂O)ⱼCH₂CH₂OH; and i, j, k, l, m, n, o, p, q, r, s, t, u, v, w, x, y and z are independently an integer from 1 to 10,000.

Aspect 6. The polyurethane composition of aspect 1 wherein the polyisocyanates and diisocyanates are selected from 4,4-methylenebis(phenyl isocyanate), 4,4-methylenebis(cyclohexyl isocyanate), 4,4'-oxybis(phenyl isocyanate), 4arm-PEG-Isocyanate, bis(4-isocyanatophenyl)methane, 4,4'-methylenebis(2-chlorophenyl isocyanate), 3,3'-dichloro-4,4'-diisocyanato-1,1'-biphenyl, hexamethylene diisocyanate, 1,4-phenylene diisocyanate, 1,3-phenylene diisocyanate, m-xylylene diisocyanate, tolylene-2,4-diisocyanate, tolylene-2,6-diisocyanate, poly(hexamethylene diisocyanate), trans-1,4-cyclohexylene diisocyanate, 4-chloro-6-methyl-1,3-phenylene diisocyanate, hexamethylene diisocyanate, toluylene diisocyanate, 1,4-diisocyanatobutane, 1,8-di isocyanatooctane, 1,3-bis(1-isocyanato-1-methylethyl)benzene, 3,3'-dimethyl-4,4'-biphenylene diisocyanate, 4,4'-methylenebis(phenyl isocyanate), 1,12-diisocyanatododecane, 1,4-diisocyanatobutane, and 1,12-diisocyanatododecane.

Aspect 7. The polyurethane composition of aspect 1, comprising repeating units of Formula I:

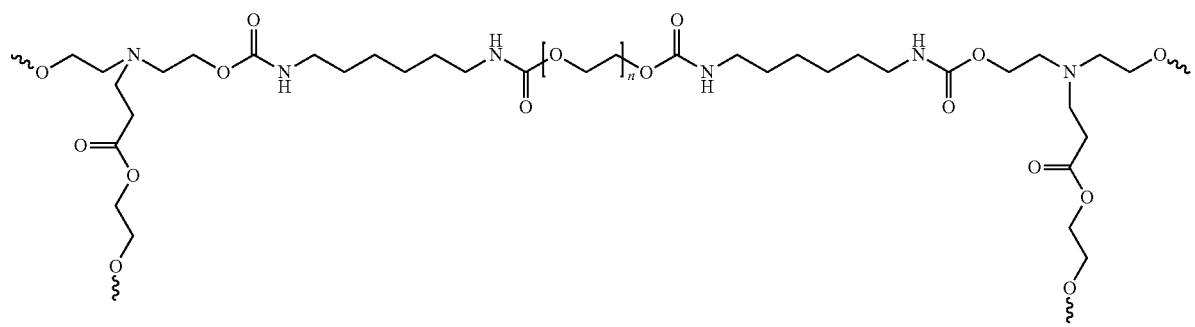

wherein the polymer has a molecular weight of about 1,000 to about 10,000,000 Dalton.

Aspect 8. The polyurethane composition of aspect 7, wherein n is 1 to about 1,000,000.

Aspect 9. The polyurethane composition of aspect 7, wherein n is 1 to about 100,000.

Aspect 10. The polyurethane composition of aspect 7, wherein n is 1 to about 10,000.

Aspect 11. The polyurethane composition of aspect 7, wherein n is 1 to about 1,000.

Aspect 12. The polyurethane composition of aspect 7, wherein n is 1 to about 100.

Aspect 13. The polyurethane composition of aspect 1, comprising repeating units of formula J:

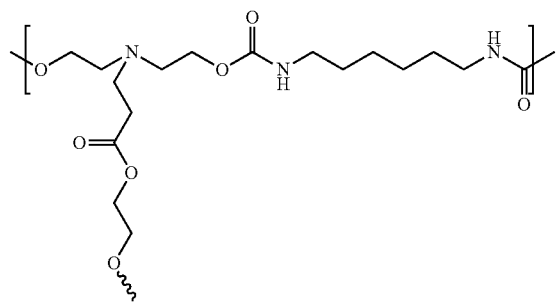

wherein the polymer has a molecular weight of about 1,000 to about 10,000,000 Dalton.

Aspect 14. The polyurethane composition of aspect 1, comprising repeating units of formula K:

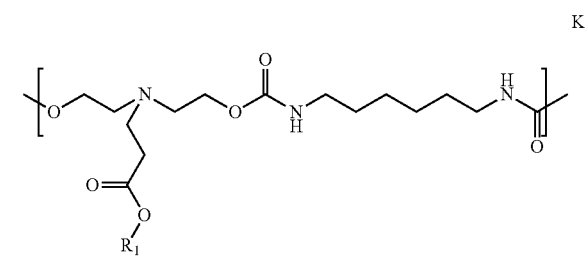

wherein the polymer has a molecular weight of about 1,000 to about 10,000,000 Dalton;

R₁ is —CH₃, —CH₂CH₃, —CH₂CH₂CH₃, —CH₂CH₂CH₂CH₃, —CH₂CH₂CH₂CH₂CH₃, —(CH₂)ᵢCH₃, —CH₂CH₂OH, —CH₂CH₂CH₂OH, —CH₂CH₂CH₂CH₂OH, —CH₂CH₂CH₂CH₂CH₂OH, (CH₂)ᵥOH, —CH₂CH₂OCH₂CH₂OH, (CH₂)ᵥO(CH₂)ₓOH, —(CH₂CH₂OCH₂CH₂)ᵧOH, or —(CH₂CH₂O)ₐCH₂CH₂OH; and a, v, w, x, y and z are independently an integer from 1 to 10,000.

Aspect 15. The polyurethane composition of aspect 1, comprising repeating units of formula L:

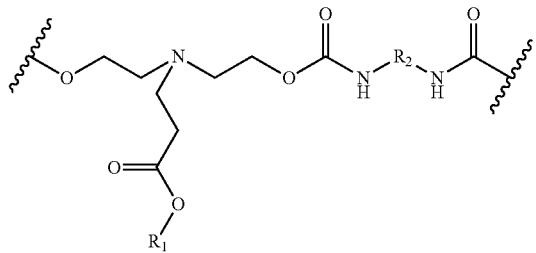

wherein the polymer has a molecular weight of about 1,000 to about 10,000,000 Dalton;
$R_1$ is —$CH_3$, —$CH_2CH_3$, —$CH_2CH_2CH_3$, —$CH_2CH_2CH_2CH_3$, —$CH_2CH_2CH_2CH_2CH_3$, —$(CH_2)_zCH_3$, —$CH_2CH_2OH$, —$CH_2CH_2CH_2OH$, —$CH_2CH_2CH_2CH_2OH$, —$CH_2CH_2CH_2CH_2CH_2OH$, —$(CH_2)_vOH$, —$CH_2CH_2OCH_2CH_2OH$, —$(CH_2)_wO(CH_2)_xOH$, —$(CH_2CH_2OCH_2CH_2)_yOH$, or —$(CH_2CH_2O)_aCH_2CH_2OH$;

$R_1$ is —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$(CH_2)_m$-, —$CH_2CH_2OCH_2CH_2$—, —$(CH_2)_nO(CH_2)_o$—, or —$(CH_2CH_2OCH_2CH_2)_p$; and a, m, n, o, p, v, w, x, y and z are independently an integer from 1 to 10,000

Aspect 16. The polyurethane composition according to claim 1, comprising repeating units of formula L:

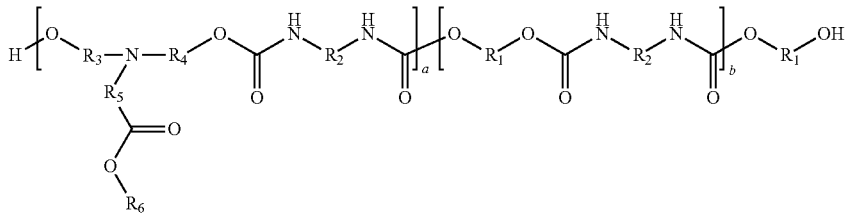

wherein $R_1$ is —$CH_2$—, —$CH_2CH_2$—, —$CH_2CH_2CH_2$—, —$CH_2CH_2CH_2CH_2$—, —$CH_2CH_2CH_2CH_2CH_2$—, —$(CH_2)_c$—, —$CH_2CH_2OCH_2CH_2$—, —$(CH_2)_dO(CH_2)_e$—, —$(CH_2CH_2OCH_2CH_2)_f$, —$(CH_2CH_2O)_gCH_2CH_2$—;
$R_2$—$CH_2$—, —$CH_2CH_2$—, —$CH_2CH_2CH_2$—, —$CH_2CH_2CH_2CH_2$—, —$CH_2CH_2CH_2CH_2CH_2$—, —$(CH_2)_h$—, —$CH_2CH_2OCH_2CH_2$—, —$(CH_2)_iO(CH_2)_o$—, —$(CH_2CH_2OCH_2CH_2)_j$;
$R_3$ and $R_4$ are independently selected from —$CH_2$—, —$CH_2CH_2$—, —$CH_2CH_2CH_2$—, —$CH_2CH_2CH_2CH_2$—, —$CH_2CH_2CH_2CH_2CH_2$—, —$(CH_2)_k$—, —$CH_2CH_2OCH_2CH_2$—, —$(CH_2)_lO(CH_2)_m$—, —$(CH_2CH_2OCH_2CH_2)_n$, and —$(CH_2CH_2O)_oCH_2CH_2$—;
$R_5$ is —$CH_2$—, —$CH_2CH_2$—, —$CH_2CH_2CH_2$—, —$CH_2CH_2CH_2CH_2$—, or —$CH_2CH_2CH_2CH_2CH_2$—;
$R_6$ is —$CH_3$, —$CH_2CH_3$, —$CH_2CH_2CH_3$, —$CH_2CH_2CH_2CH_3$, —$CH_2CH_2CH_2CH_2CH_3$, —$(CH_2)_pCH_3$, —$CH_2CH_2OH$, —$CH_2CH_2CH_2OH$, —$CH_2CH_2CH_2CH_2OH$, —$CH_2CH_2CH_2CH_2CH_2OH$, —$(CH_2)_qOH$, —$CH_2CH_2OCH_2CH_2OH$, —$(CH_2)_rO(CH_2)_sOH$, —$(CH_2CH_2OCH_2CH_2)_tOH$, or —$(CH_2CH_2O)_uCH_2CH_2OH$; and
a and b are an integer from 1 to 100,000; c, d, e, f, g, h, i, j, k, l, m, n, o, p, q, r, s, and t are an integer from 1 to 10,000.

Aspect 17. A method of preparing a polymer of formula I

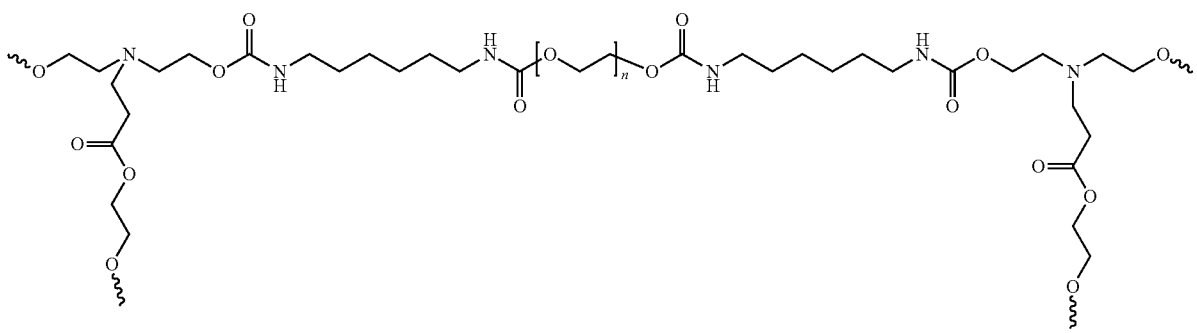

comprising i) reacting a poly(ethylene glycol) of formula 2

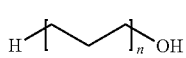

wherein n is 1 to about 1,000,000 with hexyldiisocyanate (HDI) of formula 3

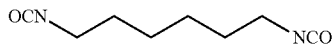

to form a compound of formula 4

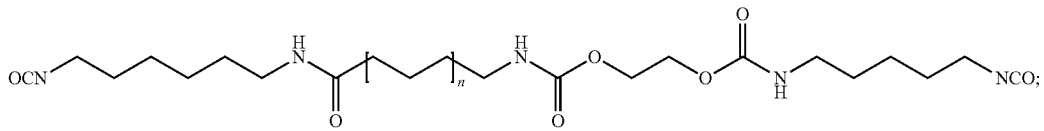

and ii) reacting the compound of formula 4 with DEAHA

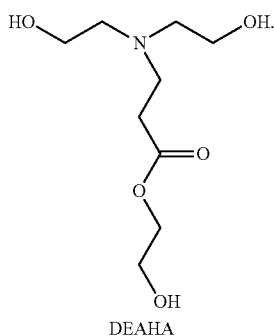 [SMILES: O=C(CCN(CCO)CCO)OCCO]

DEAHA

Aspect 18. The method of aspect 17 wherein the ratios of hydroxyl groups in DEAHA:hydroxyl groups of PEG 2:isocyanate groups in HDI 3 is from about 2:8:10 to about 8:2:10 and 10:0:10 of DEAHA:PEG:HDI.

Aspect 19. The method of aspect 17, wherein the ratios of hydroxyl groups in DEAHA:hydroxyl groups of PEG 2:isocyanate groups in HDI 3 are selected from 2:8:10, 4:6:10, 6:4:10.8:2:10 and 10:0:10.

Aspect 20. The method of aspect 17 conducted in a single reaction vessel.

What is claimed is:

1. A polymer, comprising:

a polymer backbone:

comprising a first monomeric unit, wherein the first monomeric unit is derived from a combination consisting of an isocyanate and a diol or polyol; and one or more second monomeric units, wherein the one or more second monomeric units comprise a zwitterionic precursor monomeric unit having a structure according to one or more of Formula (A1) and (B1):

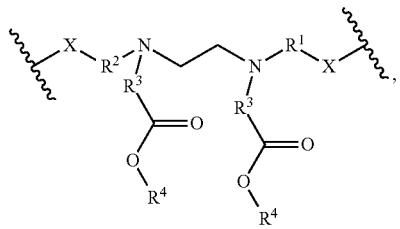

-continued (B1)

wherein in Formulas (A1) and (B1):

each X is independently O, $NR^a$, S or Se; and, each $R^1$, $R^2$, and $R^3$ is independently selected from $-(CH_2)_n-$, $-(CH_2)_nO(CH_2)_m-$, $-(CH_2CH_2OCH_2CH_2)_n-$, $-(CH_2CH_2O)_n CH_2CH_2-$, $-((CH_2)_{1-8}C(O)O)_n(CH_2)_m-$, $-((CH_2)_{1-8}C(O)O)_n(CH_2CH_2O)_m(OC(O)(CH_2)_{1-8})_p-$, $-((CH_2)_{1-8}C(O)O)_n(CH_2CH_2)_m(OC(O)(CH_2)_{1-8})_p-$, $-(CH_2C(O)O)_m(CH_2CH_2)_n(OC(O)CH_2)_m-$, $-(CH(CH_3)C(O)O)_m(CH_2CH_2)_n(OC(O)CH(CH_3))_m-$, $-(CH(CH_3)C(O)O)_m(CH_2CH_2)_n(OC(O)CH(CH_3))_m-$, $-((CH_2)_nOC(O)O)(CH_2CH_2)_m-$, $-(CH_2)_nNHC(O)(CH_2)_m-$, and $-(CH_2)_nC(O)NH(CH_2)_m$;

each $R^a$ and $R^4$ is independently selected from $-H$, $-(CH_2CH_2O)_nCH_3$, $-(CH_2CH_2O)_n(CH_2)_mCH_3$, $-(CH_2CH_2O)_n(CH_2)_mOH$, $-((CH_2)_nO)_m((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-((CH_2)_{1-8}C(O)O)_n(CH_2)_mOH$, $-((CH_2)_{1-8}C(O)O)_n(CH_2CH_2O)_m(OC(O)(CH_2)_{1-8})_pOH$, $-((CH_2)_{1-8}C(O)O)_n(CH_2CH_2)_m(OC(O)(CH_2)_{1-8})_mOH$, $-(CH_2C(O)O)_n(CH_2CH_2)_m(OC(O)CH_2)_pOH$, $-(CH(CH_3)C(O)O)_n(CH_2CH_2)_m(OC(O)CH(CH_3))_pOH$, $-((CH_2)_nOC(O)O)(CH_2CH_2)_mOH$, $-(CH_2)_nNHC(O)(CH_2)_mOH$, and $-(CH_2)_nC(O)NH(CH_2)_mOH$, $C_{1-n}$ alkyl, $C_{1-n}$ alkenyl, $C_{1-n}$ alkynyl, $C_{6-10}$ aryl, and succinimidyl, wherein any one or more H atoms of $R^a$ or $R^4$ can optionally be replaced with an F atom; and each n, m, p, q, r, and s is independently 1 to 10,000.

2. A polymer comprising:
a polymer backbone comprising:
a first monomeric unit derived from a compound consisting of an isocyanate and a diol or a polyol, and
one or more second monomeric units, the one or more second monomeric units comprising a zwitterionic precursor monomeric unit, wherein the zwitterionic precursor monomeric unit comprises a secondary or a tertiary amine within the polymer backbone; and wherein the polymer backbone comprises repeating units of Formula (I):

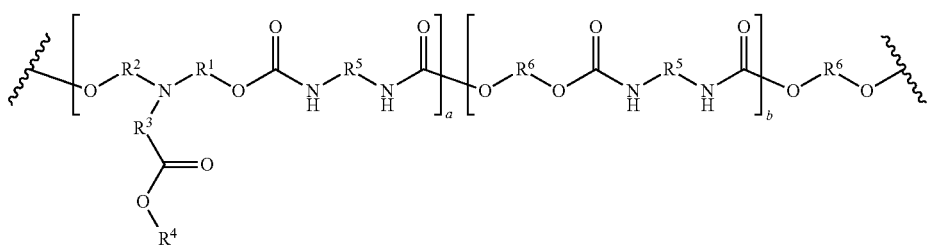

wherein
each $R^1$ and $R^2$ is independently selected from —$(CH_2)_n$—, —$(CH_2)_nO(CH_2)_m$—, —$(CH_2CH_2OCH_2CH_2)_n$—, —$(CH_2CH_2O)_nCH_2CH_2$—, —$((CH_2)_{1-8}C(O)O)_n(CH_2)_m$—, —$((CH_2)_{1-8}C(O)O)_n(CH_2CH_2O)_m(OC(O)(CH_2)_{1-8})_p$—, —$((CH_2)_{1-8}C(O)O)_n(CH_2CH_2)_m(OC(O)(CH_2)_{1-8})_p$—, —$(CH_2C(O)O)_m(CH_2CH_2)_n(OC(O)CH_2)_m$—, —$(CH(CH_3)C(O)O)_m(CH_2CH_2)_n(OC(O)CH(CH_3))_m$—, —$(CH(CH_3)C(O)O)_m(CH_2CH_2)_n(OC(O)CH(CH_3))_m$—, —$((CH_2)_nOC(O)O)(CH_2CH_2)_m$, —$(CH_2)_nNHC(O)(CH_2)_m$—, and —$(CH_2)_nC(O)NH(CH_2)_m$;
$R^3$ is —$(CH_2)_{1-5}$—;
each $R^4$ is independently selected from —H, —$(CH_2CH_2O)_nCH_3$, —$(CH_2CH_2O)_n(CH_2)_mCH_3$, —$(CH_2CH_2O)_n(CH_2)_mOH$, —$((CH_2)_nO)_m((CH_2)_pO)_q(CH_2)_rOH$, —$(CH_2CH_2O)_nH$, —$(CH_2)_nOH$, —$(CH_2)_nO(CH_2)_mOH$, —$(CH_2CH_2OCH_2CH_2)_nOH$, —$(CH_2CH_2O)_nCH_2CH_2OH$, —$((CH_2)_{1-8}C(O)O)_n(CH_2)_mOH$, —$((CH_2)_{1-8}C(O)O)_n(CH_2CH_2O)_m(OC(O)(CH_2)_{1-8})_pOH$, —$((CH_2)_{1-8}C(O)O)_n(CH_2CH_2)_m(OC(O)(CH_2)_{1-8})_mOH$, —$(CH_2C(O)O)_n(CH_2CH_2)_m(OC(O)CH_2)_pOH$, —$(CH(CH_3)C(O)O)_n(CH_2CH_2)_m(OC(O)CH(CH_3))_pOH$, —$((CH_2)_nOC(O)O)(CH_2CH_2)_mOH$, —$(CH_2)_nNHC(O)(CH_2)_mOH$, and —$(CH_2)_nC(O)NH(CH_2)_mOH$, $C_{1-n}$ alkyl, $C_{1-n}$ alkenyl, $C_{1-n}$ alkynyl, $C_{6-10}$ aryl, and succinimidyl, wherein any one or more H atoms of $R^a$ or $R^4$ can optionally be replaced with an F atom;
each of $R^5$ and $R^6$ is independently —$(CH_2)_n$—, —$(CH_2)_nO(CH_2)_m$—, —$(CH_2CH_2O)_nCH_2CH_2$—, —$(CH_2CH_2)_n(CH_2)_m$—, —$(CH_2)_n(CH_2CH_2O))_n(CH_2)_p$—, —$((CH_2)_{1-8}C(O)O)_n(CH_2)_m$—, —$((CH_2)_{1-8}C(O)O)_n(CH_2CH_2O)_m(OC(O)(CH_2)_{1-8})_p$—, —$((CH_2)_{1-8}C(O)O)_n(CH_2CH_2)_m(OC(O)(CH_2)_{1-8})_p$—, —$(CH_2C(O)O)_n(CH_2CH_2)_m(OC(O)CH_2)_p$—, —$(CH(CH_3)C(O)O)_n(CH_2CH_2)_m(OC(O)CH(CH_3))_p$—, —$(CH(CH_3)C(O)O)_n(CH_2CH_2)_m(OC(O)CH(CH_3))_p$—, —$((CH_2)_nOC(O)O)(CH_2CH_2)_m$—, —$(CH_2)_nNHC(O)(CH_2)_m$—, or —$(CH_2)_nC(O)NH(CH_2)_m$, or —$(CH_2)_nCH(OH)(CH_2)_m$—
each n, m, p, q, and r is independently 1 to 10,000;
a is 1 to 100,000; and,
b is 0 to 100,000.

3. The polymer of claim 2, wherein the isocyanate comprises hexamethylene diisocyanate (HDI).

4. The polymer of claim 1, wherein the zwitterionic precursor monomeric unit has a structure:

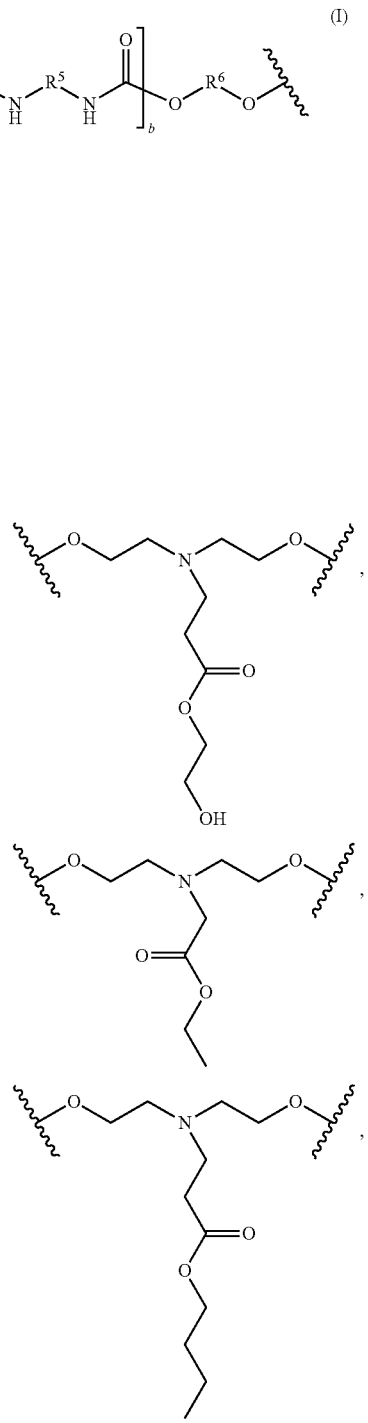

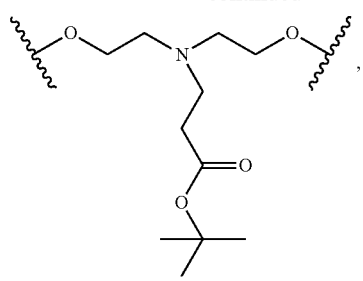
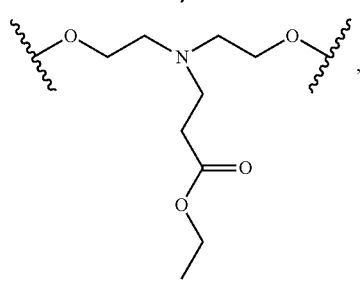
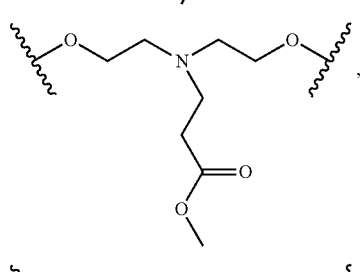
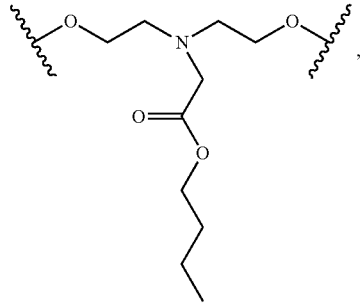
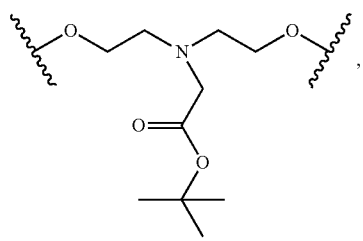
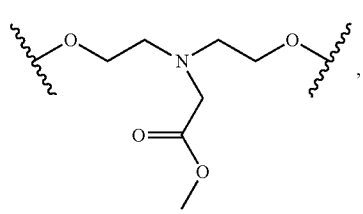
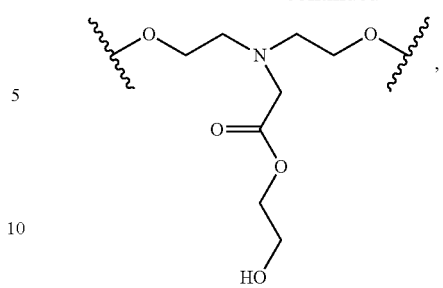
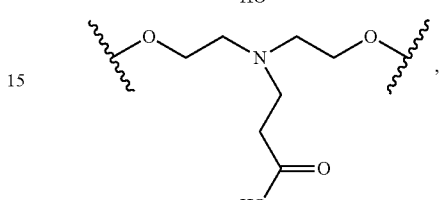
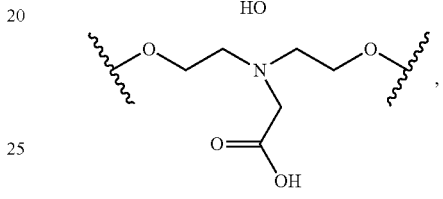
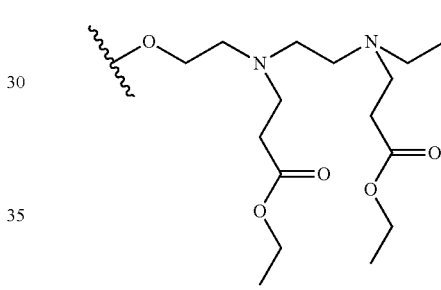
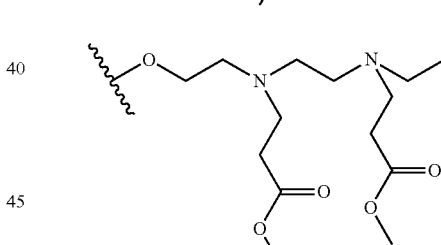
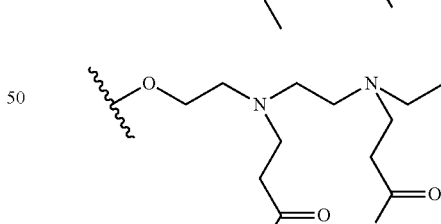
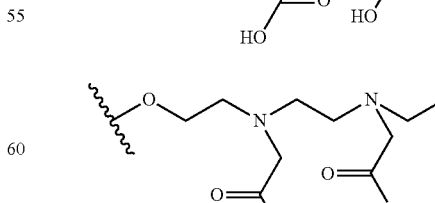
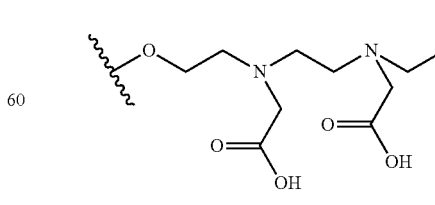
5. The polymer of claim 2, wherein $R^6$ is —$(CH_2)CH(OH)(CH_2)$—.

6. A polymer comprising:
a polymer backbone comprising:
a first monomeric unit derived from a compound consisting of an isocyanate and a diol or a polyol, and
one or more second monomeric units, the one or more second monomeric units comprising a zwitterionic precursor monomeric unit, wherein the zwitterionic precursor monomeric unit comprises a secondary or a tertiary amine within the polymer backbone; and
wherein the polymer backbone comprises repeating units of Formula (II):

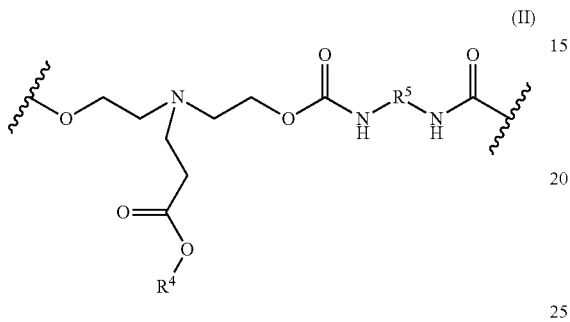

wherein each $R^4$ is independently selected from —H, —($CH_2CH_2O)_nCH_3$, —($CH_2CH_2O)_n(CH_2)_mCH_3$, —($CH_2CH_2O)_n(CH_2)_mOH$, —$((CH_2)_nO)_m((CH_2)_pO)_q$ $(CH_2)_rOH$, —$(CH_2CH_2O)_nH$, —$(CH_2)_nOH$, —$(CH_2)_nO(CH_2)_mOH$, —$(CH_2CH_2OCH_2CH_2)_nOH$, —$(CH_2CH_2O)_nCH_2CH_2OH$, —$((CH_2)_{1-8}C(O)O)_n$ $(CH_2)_mOH$, —$((CH_2)_{1-8}—C(O)O)_n(CH_2CH_2O)_m(OC(O)(CH_2)_{1-8})_pOH$, —$((CH_2)_{1-8}C(O)O)_n(CH_2CH_2)_m(OC(O)(CH_2)_{1-8})_mOH$, —$(CH_2C(O)O)_n(CH_2CH_2)_m(OC(O)CH_2)_pOH$, —$(CH(CH_3)C(O)O)_n(CH_2CH_2)_m(OC(O)CH(CH_3))_pOH$, —$((CH_2)_nOC(O)O)(CH_2CH_2)_mOH$, —$(CH_2)_nNHC(O)(CH_2)_mOH$, and —$(CH_2)_n(C(O)NH(CH_2)_mOH$, $C_{1-n}$ alkyl, $C_{1-n}$ alkenyl, $C_{1-n}$ alkynyl, $C_{6-10}$ aryl, and succinimidyl, wherein any one or more H atom of $R^4$ can optionally be replaced with an F atom;

$R^5$ is —$(CH_2)_n$—, —$(CH_2)_nO(CH_2)_m$—, —$(CH_2CH_2OCH_2CH_2)_n$—, —$(CH_2CH_2O)_nCH_2CH_2$—, —$(CH_2CH_2)_n(CH_2)_m$—, —$(CH_2)_n(CH_2CH_2O)_n(CH_2)_p$—, —$((CH_2)_{1-8}C(O)O)_n(CH_2)_m$—, —$((CH_2)_{1-8}C(O)O)_n(CH_2CH_2O)_m(OC(O)(CH_2)_{1-8})_p$—, —$((CH_2)_{1-8}C(O)O)_n(CH_2CH_2)_m(OC(O)(CH_2)_{1-8})_p$—, —$(CH_2C(O)O)_n(CH_2CH_2)_m(OC(O)CH_2)_p$—, —$(CH(CH_3)C(O)O)_n(CH_2CH_2)_m(OC(O)CH(CH_3))_p$—, —$(CH(CH_3)C(O)O)_n(CH_2CH_2)_m(OC(O)CH(CH_3))_p$—, —$((CH_2)_nOC(O)O)(CH_2CH_2)$ m, —$(CH_2)_nNHC(O)(CH_2)_m$—, —$(CH_2)_nC(O)NH(CH_2)_m$—, or —$(CH_2)_nCH(OH)(CH_2)_m$—; and each n, m, p, q, and r is independently 1 to 10,000;
or wherein the polymer backbone comprises repeating units of Formula (III), (IV), or (VI):

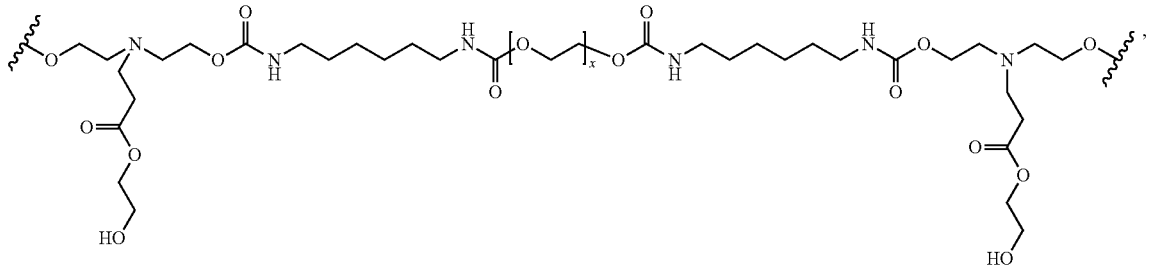

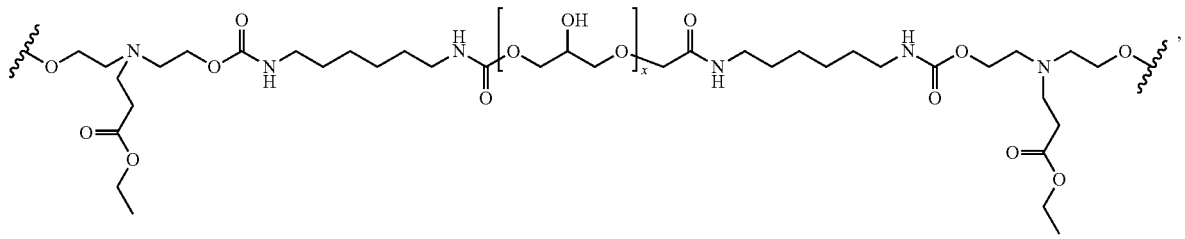

or

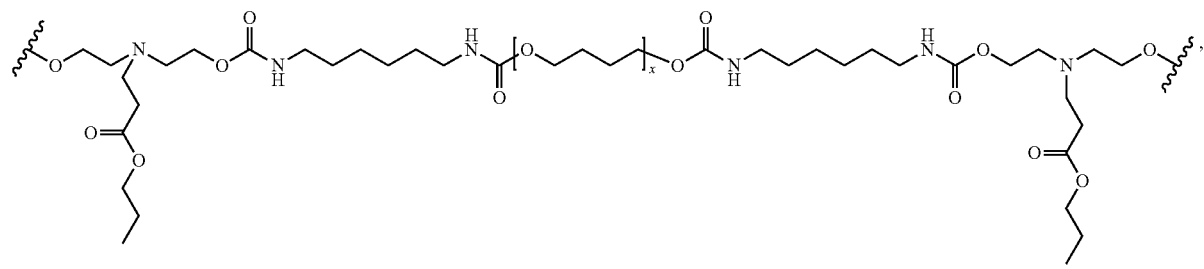

(VI)

wherein x is 1 to 1,000,000;
or wherein the polymer backbone comprises repeating units of Formula (V):

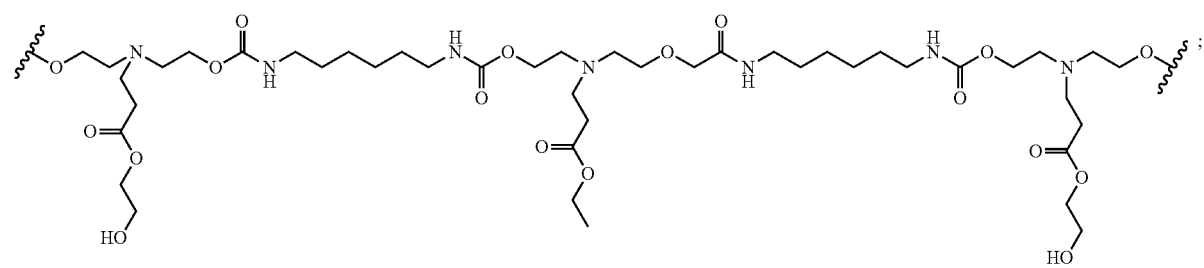

(V)

or wherein the polymer backbone comprises repeating units of Formula (VII):

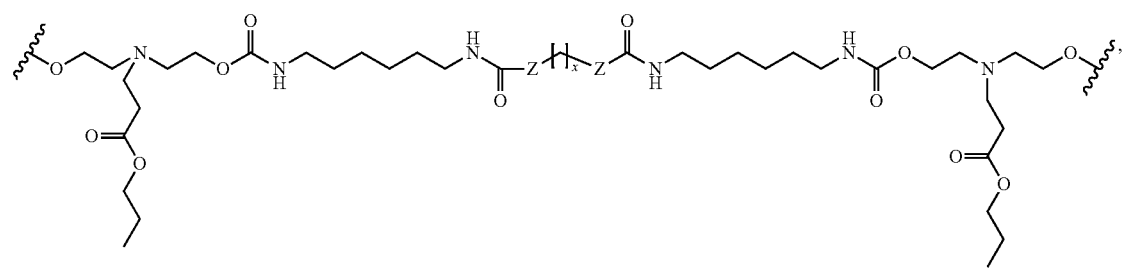

(VII)

wherein Z is O or NH, and x is 1 to 30.

7. The polymer of claim 2, wherein:
R⁵ is —(CH₂)₆—; and,
each R⁴ is —(CH₂)₂OH or —CH₂CH₃.

8. The polymer of claim 2, wherein the zwitterionic precursor monomeric unit has a structure according to Formula (C1), (D1), or (E1):

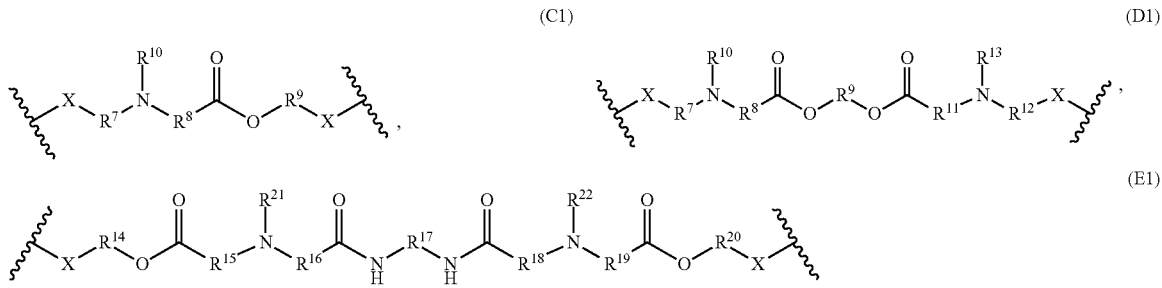

wherein:

each X is independently O, NR$^a$, S, or Se;

each R$^7$, R$^8$, R$^9$, R$^{11}$, R$^{12}$, R$^{14}$, R$^{15}$, R$^{16}$, R$^{17}$, R$^{18}$, R$^{19}$ and R$^{20}$ is independently selected from —(CH$_2$)$_n$—, —((CH$_2$)$_n$O)$_m$((CH$_2$)$_p$O)$_q$(CH$_2$)$_r$—, —(CH$_2$)$_n$O(CH$_2$)$_m$—, —(CH$_2$CH$_2$OCH$_2$CH$_2$)$_n$—, —(CH$_2$CH$_2$O)$_n$CH$_2$CH$_2$—, —((CH$_2$)$_{1-8}$C(O)O)$_m$(CH$_2$)$_n$—, —((CH$_2$)$_{1-8}$C(O)O)$_m$(CH$_2$CH$_2$O)(OC(O)(CH$_2$)$_{1-8}$)$_p$—, —((CH$_2$)$_{1-8}$C(O)O)$_m$(CH$_2$CH$_2$)$_n$(OC(O)(CH$_2$)$_{1-8}$)$_p$—, —(CH$_2$C(O)O)$_m$(CH$_2$CH$_2$)$_n$(OC(O)CH$_2$)$_p$—, —(CH(CH$_3$)C(O)O)$_m$(CH$_2$CH$_2$)$_n$(OC(O)CH(CH$_3$))$_p$—, —(CH(CH$_3$)C(O)O)$_m$(CH$_2$CH$_2$)$_n$(OC(O)CH(CH$_3$))$_p$—, —((CH$_2$)$_n$OC(O)O)(CH$_2$CH$_2$)$_m$, —(CH$_2$)$_n$NHC(O)(CH$_2$)$_m$—, and —(CH$_2$)$_n$C(O)NH(CH$_2$)$_m$;

each R$^a$, R$^{10}$, R$^{13}$, R$^{21}$, and R$^{22}$ is independently —H, —(CH$_2$CH$_2$O)$_n$CH$_3$, —(CH$_2$CH$_2$O)$_n$(CH$_2$)$_m$CH$_3$, —(CH$_2$CH$_2$O)$_n$(CH$_2$)$_m$OH, —((CH$_2$)$_n$O)$_m$((CH$_2$)$_p$O)$_q$(CH$_2$)$_r$OH, —(CH$_2$CH$_2$O)$_n$H, —(CH$_2$)$_n$OH, —(CH$_2$)$_n$O(CH$_2$)$_m$OH, —(CH$_2$CH$_2$OCH$_2$CH$_2$)$_n$OH, —(CH$_2$CH$_2$O)$_n$CH$_2$CH$_2$OH, —(CH$_2$CH$_2$OCH$_2$CH$_2$)$_n$OH, —((CH$_2$)$_{1-8}$C(O)O)$_n$(CH2)$_m$OH, —((CH$_2$)$_{1-8}$C(O)O)$_n$(CH$_2$CH$_2$O)$_m$(OC(O)(CH$_2$)$_{1-8}$)$_p$OH, —((CH$_2$)$_{1-8}$C(O)O)$_n$(CH$_2$CH$_2$)$_m$(OC(O)(CH$_2$)$_{1-8}$)$_p$OH, —(CH$_2$C(O)O)$_n$(CH$_2$CH$_2$)$_m$(OC(O)CH$_2$)$_p$OH, —(CH(CH$_3$)C(O)O)$_n$(CH$_2$CH$_2$)$_m$(OC(O)CH(CH$_3$))$_p$OH, —(CH(CH$_3$)C(O)O)$_n$(CH$_2$CH$_2$)$_m$(OC(O)CH(CH$_3$))$_p$OH, —((CH$_2$)$_n$OC(O)O)(CH$_2$CH$_2$)$_m$OH, —(CH$_2$)$_n$NHC(O)(CH$_2$)$_m$OH, —(CH$_2$)$_n$C(O)NH(CH$_2$)$_m$OH, C$_{1-n}$ alkyl, C$_{1-n}$ alkenyl, C$_{1-n}$ alkynyl, or C$_{6-10}$ aryl, wherein any one or more H atoms of R$^a$, R$^{10}$, R$^{13}$, R$^{21}$, or R$^{22}$ can optionally be replaced with an F atom; and, each n, m, p, q and r is independently 1 to 10,000.

9. The polymer of claim 8, wherein the zwitterionic precursor monomeric unit has a structure:

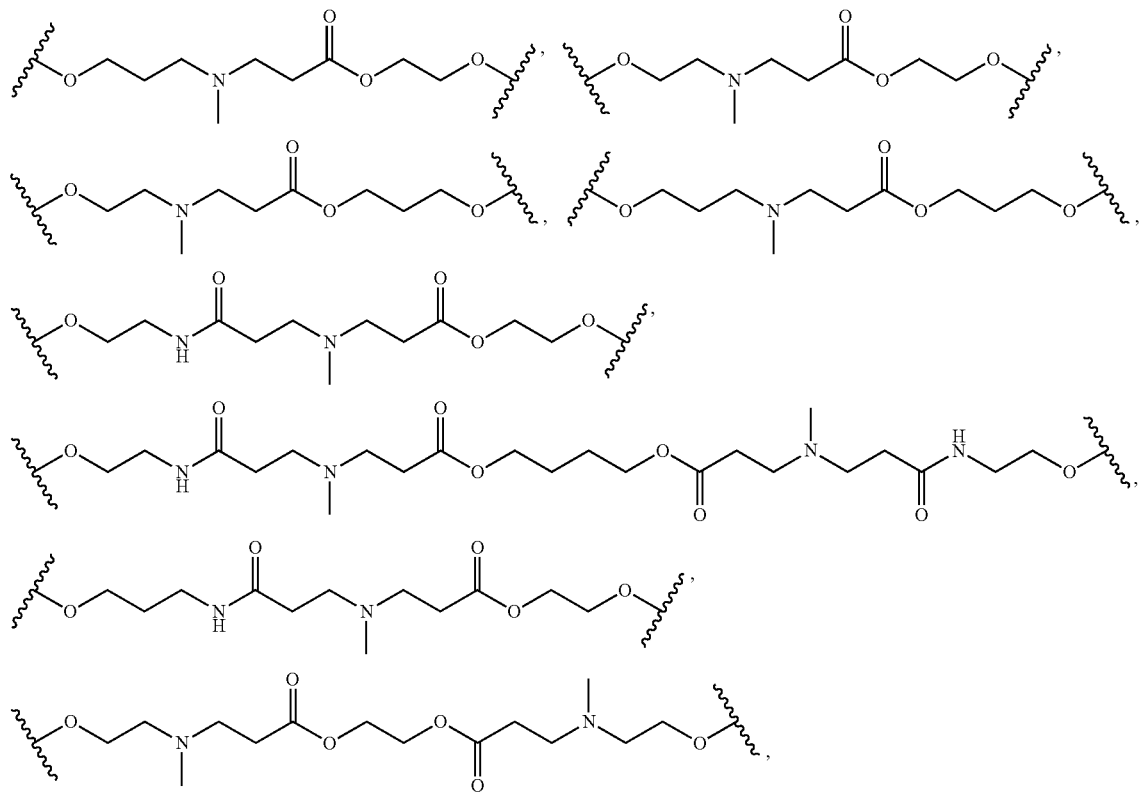

-continued

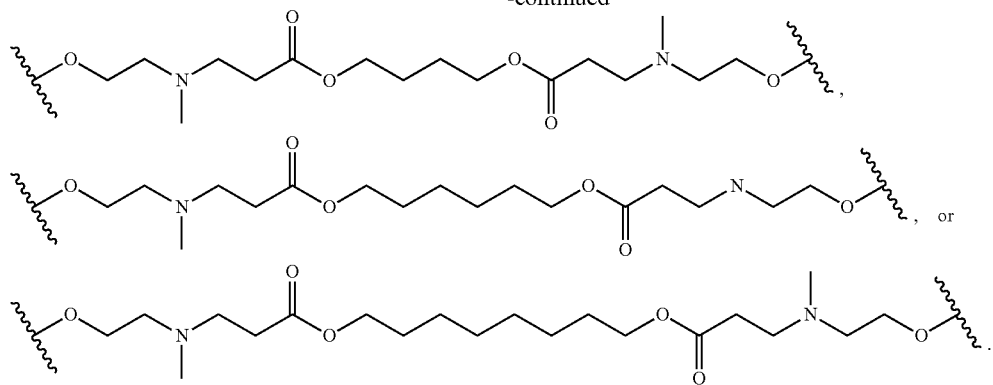

10. The polymer of claim 2, wherein the ratio of hydroxyl groups in the zwitterionic precursor monomeric unit:hydroxyl groups in the diol or polyol:isocyanate groups in the isocyanate is selected from the group of 2:8:10, 4:6:10, 6:4:10, 8:2:10, 75:25:100, 50:50:100, and 25:75:100.

11. The polymer of claim 10, wherein the ratio is selected from the group consisting of 2:8:10, 4:6:10, 6:4:10, and 8:2:10.

12. The polymer of claim 2, wherein the polymer is hydrolyzed.

* * * * *

UNITED STATES PATENT AND TRADEMARK OFFICE
CERTIFICATE OF CORRECTION

PATENT NO. : 12,234,314 B2  
APPLICATION NO. : 17/047716  
DATED : February 25, 2025  
INVENTOR(S) : Gang Cheng et al.

Page 1 of 1

It is certified that error appears in the above-identified patent and that said Letters Patent is hereby corrected as shown below:

In the Claims

At Column 91, Line 57, "$R^a$ or $R^4$" should be -- $R^4$ --.

At Column 91, Line 60, "—$(CH_2)_nO(CH_2)_m$—," should be -- —$(CH_2)_nO(CH_2)_m$—, —$(CH_2CH_2OCH_2CH_2)_n$—, --.

At Column 91, Line 61, "—$(CH_2)_n(CH_2CH_2O))_n$" should be -- —$(CH_2)_n(CH_2CH_2O)_n$ --.

At Column 92, Line 3, "$(CH_2)_m$—" should be -- $(CH_2)_m$—; --.

At Column 96, Line 4, "—$((CH_2)_{1-8}$—$C(O)O)_n$" should be -- —$((CH_2)_{1-8}C(O)O)_n$ --.

At Column 96, Line 10, "—$(CH_2)_n(C(O)NH(CH_2)_mOH$," should be -- —$(CH_2)_nC(O)NH(CH_2)_mOH$, --.

At Column 96, Line 23, "—$((CH_2)_nOC(O)O)(CH_2CH_2)$ m," should be -- —$((CH_2)_nOC(O)O)(CH_2CH_2)_m$, --.

At Column 96, Line 25, "$NH(CH_2)_m$—," should be -- $NH(CH_2)_m$, --.

At Column 100, Line 18, "—$((CH_2)_{1-8}C(O)O)_n(CH2)_mOH$," should be -- —$((CH_2)_{1-8}C(O)O)_n(CH_2)_mOH$, --.

At Column 100, Lines 22-24, "—$(CH(CH_3)C(O)O)_n(CH_2CH_2)_m(OC(O)CH(CH_3)_pOH$, —$(CH(CH_3)C(O)O)_n(CH_2CH_2)_m(OC(O)CH(CH_3))_pOH$," should be -- —$(CH(CH_3)C(O)O)_n(CH_2CH_2)_m(OC(O)CH(CH_3))_pOH$, --.

At Column 101, Lines 20-21, "unit:hydroxyl" should be -- unit: hydroxyl --.

Signed and Sealed this  
Twenty-ninth Day of July, 2025

Coke Morgan Stewart  
*Acting Director of the United States Patent and Trademark Office*